（12）United States Patent
Chono et al.

(10) Patent No.: US 9,913,625 B2
(45) Date of Patent: Mar. 13, 2018

(54) MEDICAL DIAGNOSIS DEVICE AND MEASUREMENT METHOD THEREOF

(71) Applicant: HITACHI ALOKA MEDICAL, LTD., Mitaka-shi, Tokyo (JP)

(72) Inventors: Tomoaki Chono, Mitaka (JP); Takahiro Kashiyama, Mitaka (JP); Tomofumi Nishiura, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 75 days.

(21) Appl. No.: 14/651,971

(22) PCT Filed: Nov. 20, 2013

(86) PCT No.: PCT/JP2013/081313
§ 371 (c)(1),
(2) Date: Jun. 12, 2015

(87) PCT Pub. No.: WO2014/155825
PCT Pub. Date: Oct. 2, 2014

(65) Prior Publication Data
US 2015/0320399 A1    Nov. 12, 2015

(30) Foreign Application Priority Data
Mar. 29, 2013  (JP) .................................. 2013-072104

(51) Int. Cl.
*G06K 9/00*  (2006.01)
*A61B 8/08*  (2006.01)
(Continued)

(52) U.S. Cl.
CPC .......... *A61B 8/5223* (2013.01); *A61B 8/0883* (2013.01); *A61B 8/463* (2013.01);
(Continued)

(58) Field of Classification Search
None
See application file for complete search history.

(56) References Cited

U.S. PATENT DOCUMENTS 5,644,765 A * 7/1997 Shimura ............ G06F 17/30256
8,094,899 B2 * 1/2012 Chouno ................. A61B 5/055
382/128

(Continued)

FOREIGN PATENT DOCUMENTS

CN    101522107 A    9/2009
JP    2007-222325 A   9/2007
(Continued)

OTHER PUBLICATIONS

Second and Supplementary Notice (Form PCT/IB/308) issued in counterpart International Application No. PCT/JP2013/081313 dated Jul. 30, 2015.
(Continued)

*Primary Examiner* — Avinash Yentrapati
(74) *Attorney, Agent, or Firm* — Westerman, Hattori, Daniels & Adrian, LLP

(57) ABSTRACT

Provided is a medical diagnosis device that further increases the reliability of measurement results on the basis of an image of a subject. The medical diagnosis device is characterized by being provided with: an image generation unit that generates an image of a subject; an auxiliary information generation unit that generates auxiliary information on the basis of input from an operation unit; a measurement computation unit that computes a measurement position using the image generated by the image generation unit, the auxiliary information, and measurement conditions, and computes measurement values using the image generated by the image generation unit and the computed measurement position; and a display unit that displays the image generated
(Continued)

by the image generation unit, the input position information, and the measurement value computed by the measurement computation unit.

13 Claims, 30 Drawing Sheets

(51) Int. Cl.
    *G06T 11/60*     (2006.01)
    *A61B 8/00*     (2006.01)
    *G06F 3/0484*     (2013.01)
    *G06T 7/12*     (2017.01)
    *G06T 7/62*     (2017.01)

(52) U.S. Cl.
    CPC .............. *A61B 8/465* (2013.01); *A61B 8/469* (2013.01); *A61B 8/486* (2013.01); *A61B 8/5207* (2013.01); *A61B 8/5284* (2013.01); *G06F 3/04845* (2013.01); *G06T 7/12* (2017.01); *G06T 7/62* (2017.01); *G06T 11/60* (2013.01); *G06T 2207/10132* (2013.01); *G06T 2207/20221* (2013.01); *G06T 2207/30048* (2013.01)

(56) References Cited

U.S. PATENT DOCUMENTS

| | | | | |
|---|---|---|---|---|
| 8,394,024 B2* | 3/2013 | Miyama | ................... | A61B 8/06 600/437 |
| 2009/0163812 A1* | 6/2009 | Chouno | ................... | A61B 8/08 600/443 |
| 2010/0036248 A1* | 2/2010 | Chouno | ................. | A61B 6/563 600/443 |
| 2010/0074475 A1* | 3/2010 | Chouno | ................. | A61B 5/055 382/107 |
| 2012/0065499 A1* | 3/2012 | Chono | .................... | A61B 8/00 600/425 |
| 2012/0083698 A1* | 4/2012 | Chono | ............... | A61B 5/02007 600/443 |
| 2012/0308109 A1* | 12/2012 | Yoshida | ............... | A61B 5/1075 382/131 |
| 2013/0012835 A1* | 1/2013 | Chono | ................... | A61B 8/463 600/587 |

FOREIGN PATENT DOCUMENTS

| | | |
|---|---|---|
| JP | 2012-081177 A | 4/2012 |
| WO | 2008/044441 A1 | 4/2008 |
| WO | 2011/065414 A1 | 6/2011 |

OTHER PUBLICATIONS

Notification Concerning Transmittal of International Preliminary Report on Patentability (Form PCT/IB/326) issued in counterpart International Application No. PCT/JP2013/081313 dated Oct. 8, 2015 with Forms PCT/IB/373 and PCT/ISA/237. (6 pages).

Notification of Transmittal of Translation of the International Preliminary Report on a Patentability (Form PCT/IB/338) issued in counterpart International Application No. PCT/JP2013/081313 dated Oct. 8, 2015 with Forms PCT/IB/373 and PCT/ISA/237. (9 pages).

International Search Report dated Feb. 4, 2014, issued in corresponding application No. PCT/JP2013/081313 (1 page).

Office Action dated Dec. 30, 2016, issued in counterpart Chinese Patent Application No. 201380073788.2, with English translation. (21 pages).

Office Action dated Jul. 13, 2017, issued in counterpart Chinese Application No. 201380073788.2, with English translation. (22 pages).

* cited by examiner

| 1510 | 1520 | 1530 | | 1540 | 1550 |
|---|---|---|---|---|---|
| PART | MEASUREMENT ITEM | MEASUREMENT POSITION | | NUMBER OF MEASUREMENT | MEASUREMENT COMPUTATION |
| HEART | LEFT VENTRICLE VOLUME | ANNULUS PORTION | KEY TISSUE (KEY POSITION) | ANNULUS PORTION 2 | COMPUTATION OF POSITIONS OF ANNULUS PORTION AND CARDIAC APEX PORTION |
| | | CARDIAC APEX PORTION | KEY TISSUE (KEY POSITION) | CARDIAC APEX PORTION 2 | |
| | | CONTOUR LINE | POSITION INDICATED BY INDICATION POINT 363 IS KEY TISSUE (KEY POSITION) | CONTOUR LINE 1 | |
| | PERIMETER (CONTOUR LENGTH) | CONTOUR LINE | POSITION INDICATED BY INDICATION POINT 363 IS KEY TISSUE (KEY POSITION) | CONTOUR LINE 1 | CONTOUR EXTRACTION COMPUTATION |
| MAMMARY GLAND | ... | ... | ... | ... | ... |

FIG. 30

MEDICAL DIAGNOSIS DEVICE AND MEASUREMENT METHOD THEREOF

TECHNICAL FIELD

The present invention relates to a medical diagnosis device, such as an ultrasonic diagnostic device, having an image display function of displaying a diagnostic image of a subject, and to a control method thereof.

BACKGROUND ART

Medical diagnosis devices having an image display function of displaying a diagnostic image of a subject, such as an ultrasound diagnostic device, X-ray equipment, and nuclear magnetic resonance imaging (MRI) equipment, not only generate and display an image of a target part, but also further measure a state of the part based on the image to obtain information useful for diagnosis. For example, an ultrasonic diagnostic device measures a state of a part of a subject, e.g., a tissue such as a heart; for example, the volume of a heart chamber, to obtain information useful for diagnosis.

Medical diagnosis devices which display a diagnostic image of a subject compute and set a measurement position of a tissue to be measured, such as a contour of a heart chamber, based on a generated image of a part of the subject, and perform measurement based on the set measurement position to obtain information about the tissue of the part used for diagnosis. Such a technology has been disclosed in Patent Document 1.

Patent Document 1: International Publication No. WO2008/044441

SUMMARY OF INVENTION

Technical Problem

The technology described in Patent Document 1 is a very useful technology for measuring a state of a part of a subject or a tissue of the part, and is considered very important in medical practice. Since this technology serves to provide important information which is very useful in medical practice, there is an increasing need for improved accuracy of the technology. To perform accurate measurement about a part of a subject or a tissue of the part, it is important to more accurately obtain a measurement position of the part or the tissue thereof; for example, a contour.

In some subjects to be examined by a medical diagnosis device, a target part with a clinical history or a tissue constituting the target part may have a different shape from that of a healthy person. Desirably, a more accurate measurement position can be obtained even about such a subject having a different shape of a part or a tissue from that of the healthy person, and accordingly, the reliability of measurement results based on an image of the subject is further improved.

It is an advantage of the present invention to provide a medical diagnosis device that further increases the reliability of measurement results based on an image of a subject, or a control method thereof.

Solution to Problem

A medical diagnosis device according to the present invention for achieving the above-described object includes: an image generation unit that generates an image of a subject; an auxiliary information generation unit that generates auxiliary information on the basis of input; a measurement computation unit that computes a measurement position using the image generated by the image generation unit, the auxiliary information, and a measurement condition, and computes a measurement value using the image and the computed measurement position; and a display unit that displays the image generated by the image generation unit, and the measurement value computed by the measurement computation unit. In the present invention, a measurement position is a concept for computing a measurement value. The measurement position may be represented as a shape such as a point or a line. For example, the measurement position may be a contour line of a part or a tissue within a subject. This contour line may represent a portion of the part or tissue within the subject, or may represent the whole of the part or tissue. In a case where the heart of a subject is a measurement target, the measurement position is, for example, the contour line of a cardiac ventricle. Further, in the present invention, auxiliary information is information for facilitating computation for obtaining a measurement position. The auxiliary information is, for example, information which gives a refinement condition for identifying the measurement position by computation, and may be information represented as a point, a line, a region, or the like on the image.

Advantageous Effect of Invention

The present invention can provide a medical diagnosis device that further increases the reliability of measurement results based on an image of a subject, or a control method thereof.

BRIEF DESCRIPTION OF DRAWINGS

FIG. 30 is an illustrative diagram illustrating one example of a measurement condition database.

DESCRIPTION OF EMBODIMENTS

Figure 1:
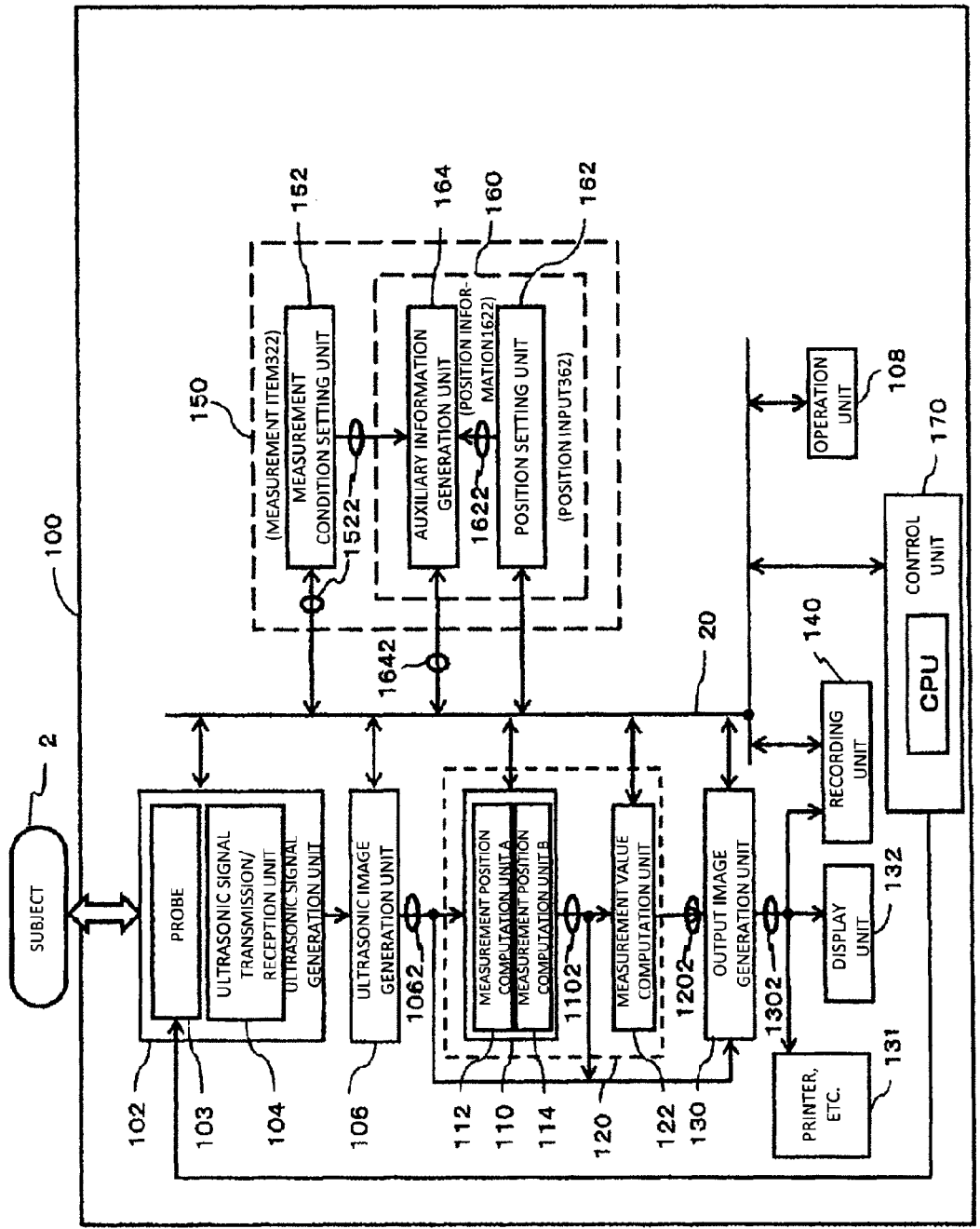
FIG. 1 is a configuration diagram of an ultrasonic diagnostic device to which the present invention is applied.

Embodiments for carrying out the present invention (hereinafter referred to as embodiments) will be described with reference to the drawings. In the following drawings, substantially the same operations, functions, and procedures are given the same reference numerals, and overlapping descriptions are omitted in order to avoid complexity. Further, in the present application, the term "computation" is used to mean not only algebraic calculation, but also a process in which a value defined as a function of a parameter is previously determined and stored in a storage means, and the value of the function is determined by searching based on the parameter. Further, the term "set" means a state where information, a condition, or a method inputted by an examiner is settled, or information, a condition, or a method captured from a different configuration, system, or device is settled. For example, as a method for settlement, an examiner inputs an instruction to perform settlement, or a predetermined time elapses.

Figure 2:
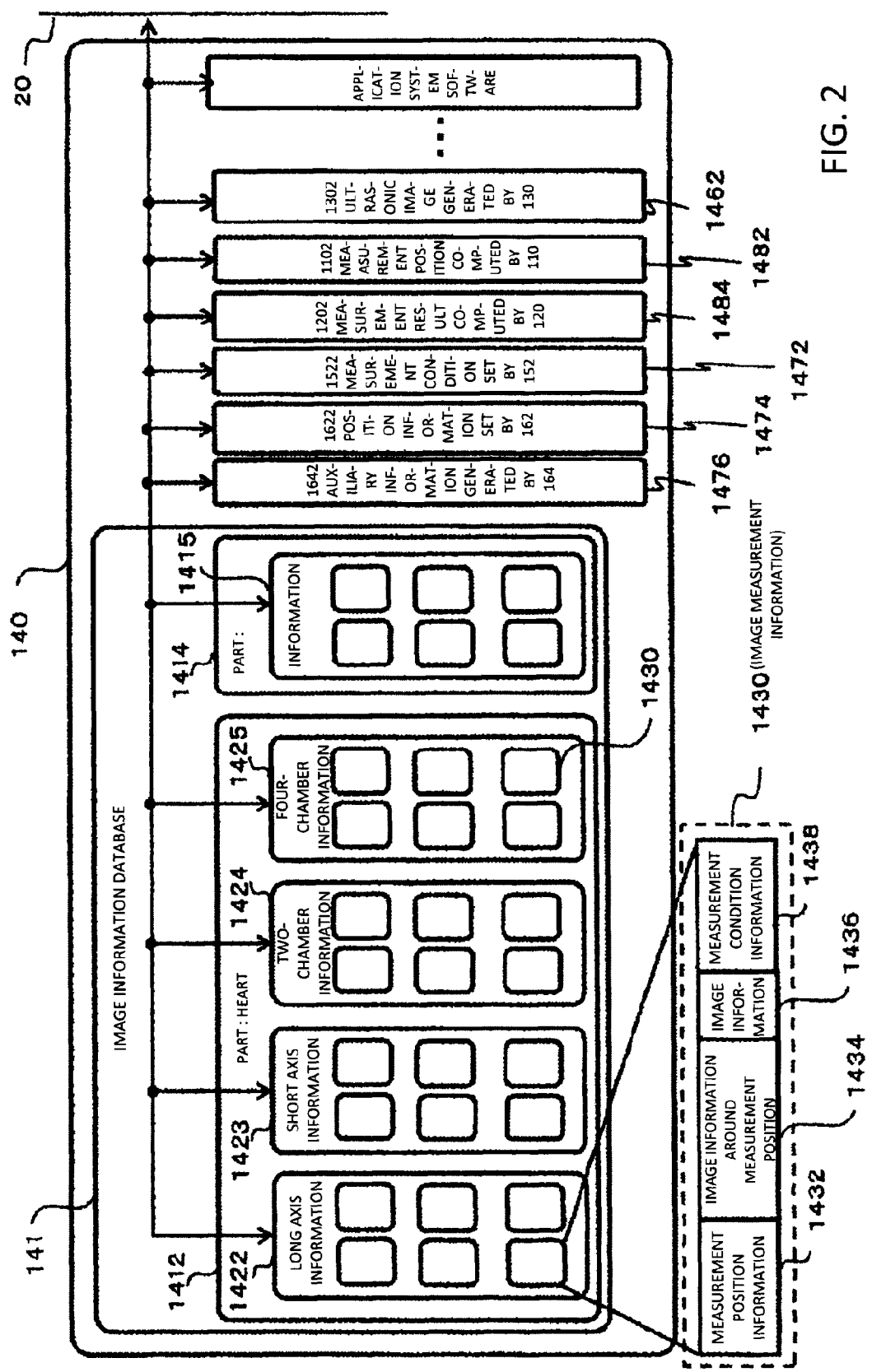
FIG. 2 is an illustrative diagram illustrating storage contents stored in a recording unit.

FIG. 1 is a block diagram of an ultrasonic diagnostic device 100 representative of one embodiment to which the present invention is applied. In addition, FIG. 2 is an illustrative diagram illustrating storage contents, storage areas, and database components stored in a recording unit 140 shown in FIG. 1. In the following embodiments, an ultrasonic diagnostic device is referred to as a representative example of a medical diagnosis device having an image display unit, and one embodiment of the present invention will be described below using the ultrasonic diagnostic device as a representative example.

[Description of Overall Configuration]

The ultrasonic diagnostic device 100 shown in FIG. 1 includes an ultrasonic signal generation unit 102, an ultrasonic image generation unit 106, a measurement computation unit 120, an output image generation unit 130, a display unit 132, a measurement setting unit 150, an operation unit 108, the recording unit 140, and a control unit 170. The measurement computation unit 120 includes a measurement position computation unit 110 and a measurement value computation unit 122. The measurement position computation unit 110 and the measurement value computation unit 122 may be constructed in different pieces of hardware or in the same piece of hardware. For example, a computing unit able to perform high-speed computation processing may be used to execute processing performed by the measurement position computation unit 110 and processing performed by the measurement value computation unit 122 at appropriate timing.

The measurement position computation unit 110 includes a measurement position computation unit A 112 and a measurement position computation unit B 114. These units may be constructed in different pieces of hardware or in the same piece of hardware in the same manner as described above. Even if the units are constructed in the same piece of hardware, the hardware operates as the measurement position computation unit A 112 at timing when the measurement position computation unit A 112 needs to perform processing, and as the measurement position computation unit B 114 at timing when the measurement position computation unit B 114 needs to perform processing. In this manner of operation, the measurement position computation unit A 112 and the measurement position computation unit B 114 can be constructed in the same piece of hardware. The same also applies to an auxiliary information setting unit 160 and the measurement setting unit 150.

The measurement setting unit 150 includes a measurement condition setting unit 152 and the auxiliary information setting unit 160. Further, the auxiliary information setting unit 160 includes a position setting unit 162 and an auxiliary information generation unit 164. While these components are represented on the basis of their respective functions, each function may be implemented as hardware, software, or a combination of hardware and software. While the components are connected through a connection line 20, the connection line 20 is not limited to hardware, which means that each of the components has a function of exchanging information with the other components. The same also applies to each of components described below.

The ultrasonic signal generation unit 102 includes a probe 103 having a transducer, and an ultrasonic signal transmission/reception unit 104. The probe 103 is a device which applies ultrasonic waves from the transducer to a target tissue of a subject 2 and receives reflected waves of the ultrasonic waves from the target tissue of the subject 2. The probe 103 may be of a linear type, a convex type, or a sector type, depending on objectives, target parts, and the like. The ultrasonic signal transmission/reception unit 104 transmits and receives an electrically converted ultrasonic signal to and from the probe 103. It receives information about power and timing of transmission/reception from the control unit 170 to control transmission/reception such that a desired ultrasonic signal is achieved. Then, the signal from the ultrasonic signal transmission/reception unit 104 is subjected to signal processing through a phasing circuit or an amplifier circuit (not shown) according to imaging setting contents, and sent to the ultrasonic image generation unit 106.

The ultrasonic image generation unit 106 generates an ultrasonic image on the basis of imaging setting contents, such as a scanning area of an ultrasonic beam or a gain setting value, from the ultrasonic signal sent through the phasing circuit or the amplifier circuit from the ultrasonic signal transmission/reception unit 104. In addition to imaging signal amplitude information, the ultrasonic image generation unit 106 has a function of imaging speed information measured from the ultrasonic signal by an unillustrated Doppler measurement unit. Such an ultrasonic image is constantly updated according to a frame rate determined by the imaging setting, and is stored through the output image generation unit 130 into a storage area 1462 of the recording unit 140, and displayed as an image by the display unit 142.

Although it is obvious that flows of information from the ultrasonic signal generation unit 102 through the ultrasonic image generation unit 106 and the output image generation unit 130 to the display unit 142 and the recording unit 140 may be considered to be via the connection line 20, these flows are represented as arrows separate from the connection line 20 so as to be easily recognized.

The measurement computation unit 120 includes the measurement position computation unit 110 which computes a measurement position, and the measurement value computation unit 122 which computes a measurement value from the computed measurement position. While the measurement position computation unit 110 and the measurement value computation unit 122 are shown in the block diagram on the basis of processing function, the measurement position computation unit 110 and the measurement value computation unit 122 may perform processing using the same computing unit, or may have their respective processing units. However, processing using the same processing unit has more and various advantages as a system. In the case where the common computing unit performs processing of both units, the common computing unit performs processing of the measurement position computation unit 110 at timing when it should operate as the measurement position computation unit 110, and the common computing unit operates as the measurement value computation unit 122 at timing when it should operate as the measurement value computation unit 122. This control may be performed by an OS program of the system or by the control unit 170.

The measurement position computation unit 110 includes the measurement position computation unit A 112 and the measurement position computation unit B 114. Each the measurement position computation unit A 112 and the measurement position computation unit B 114 has a function of computing measurement position information 1102 which indicates the measurement position, on the basis of an image of a database 141 held in the recording unit 140 based on a tissue image 1062 generated by the ultrasonic image generation unit 106. The measurement position computation unit A 112 computes a measurement position using the database 141 held in the recording unit 140 based on the tissue image 1062 generated by the ultrasonic image generation unit 106, and sends the measurement position, which is obtained as the measurement position information 1102, to the measurement value computation unit 122. If the measurement position information 1102 computed by the measurement position computation unit A 112 is not appropriate, then, on the instruction of an examiner, the measurement position computation unit B 114 further uses auxiliary information 1642 from the measurement setting unit 150 to compute a measurement position, and sends the computed measurement position as the measurement position information 1102 to the measurement value computation unit 122. The measurement position computation unit A 112 and the measurement position computation unit B 114 are not required to be completely separate components, and may share a section that performs common processing. This holds whether the measurement position computation unit A 112 and the measurement position computation unit B 114 are constructed as hardware or software. It has been described that a measurement position is computed and sent to the measurement value computation unit 122, but in practice, the computed measurement position is stored, and at timing when it is required in the processing operation, the measurement value computation unit 122 reads out and uses the stored measurement position from a storage device. This also applies to description of operation in the other blocks.

The measurement position computation unit B 114 computes an optimal measurement position based on the auxiliary information 1642 set by the measurement setting unit 150. For example, the measurement position computation unit B 114 compares an image region based on the auxiliary information 1642 within the tissue image 1062 generated by the ultrasonic image generation unit 106 to portions especially related to the auxiliary information 1642 within images in the database 141 held in the recording unit 140, to select an image having a higher similarity, and computes the optimal measurement position based on the selected image.

As a computing scheme performed by the measurement position computation unit A 112 and the measurement position computation unit B 114 of the measurement position computation unit 110 to obtain a measurement position, a method of measurement position detection using image recognition computation is used. Examples of image recognition computation include a statistical estimation method, image edge detection processing, and a pattern matching method.

In this context, the auxiliary information 1642 as described above is used as information to indicate a measurement position candidate region in a region that indicates a rough position of a measurement position, by the measurement position computation unit B 114. Accordingly, processing is performed to search this measurement position candidate region on an ultrasonic image generated by the ultrasonic image generation unit 106, to detect as the measurement position a position having characteristics closest to those of a target measurement position. The characteristics are quantified to be an index of the likelihood of the measurement position. Timing when measurement position computation is performed by the measurement position computation unit A 112 and the measurement position computation unit B 114 of the measurement position computation unit 110 may be, for example, a characteristic time phase such as end-diastole or end-systole in the case of a heart's moving image. In a case where measurement of a still image is targeted, the timing may be after the image is made static. When the measurement position is determined by the measurement position computation unit 110, the determined measurement position information 1102 is sent to the output image generation unit 130, and an image 1302 where the measurement position information 1102 is superimposed on the tissue image 1062 from the ultrasonic image generation unit 106 is created by the output image generation unit 130 and displayed on the display unit 132. Further, the measurement position information 1102 is sent from the measurement position computation unit 110 to the measurement value computation unit 122. If the measurement position computed by the measurement position computation unit A 112 is not proper, the examiner inputs an indication that it is not proper, along with an auxiliary position serving as a hint (hereinafter referred to as an auxiliary position). On the basis of these inputs, the measurement position computation unit B 114 of the measurement position computation unit 110 performs operation.

The measurement value computation unit 122 performs measurement computation on the basis of the measurement position computed by the measurement position computation unit 110. Types of measurement computation performed by the measurement value computation unit 122 are previously set by the measurement condition setting unit 152, and held in a storage area 1472 of the recording unit 140. The above-described types of measurement computation may be, for example, the speed of a measurement position, the distance between a plurality of measurement positions, the area or volume surrounded by a plurality of measurement positions, the flow rate of blood at a measurement position, the distortion in a measurement position, etc., and are items of measurement performed by the ultrasonic diagnostic device 100. On the basis of the measurement position information 1102, the measurement value computation unit 122 performs measurement computation, among the above-described types of measurement computation, according to a measurement condition 1522 which has been set by the measurement condition setting unit 152 and held in the storage area 1472 of the recording unit 140. Then, the result of the measurement computation is sent to the output image generation unit 130 and displayed on the display unit 132.

As described above, the output image generation unit 130 generates the image 1302 from only one or a combination of various kinds of information as required, such as the tissue image 1062 generated by the ultrasonic image generation unit 106, the measurement position information 1102 computed by the measurement position computation unit A 112 or the measurement position computation unit B 114 of the measurement position computation unit 110, a measurement value 1202 calculated by the measurement value computation unit 122, and a position input 362 inputted in the position setting unit 162, in such a way to be easily understood by the examiner, and displays the image 1302 on the display unit 132. In addition, the image 1302 can be printed by a printer 131 as required.

The measurement setting unit 150 includes the measurement condition setting unit 152 and the auxiliary information setting unit 160 that generates and outputs the auxiliary information 1642, such as a measurement position candidate region, which serves as a refinement condition for identifying a measurement position by computation. The auxiliary information 1642 is a hint for or helps the measurement position computation unit B 114 of the measurement position computation unit 110 to perform computation for identifying the measurement position, such as candidates including the region of the measurement position. A measurement condition inputted by the examiner through the operation unit 108 is set by the measurement condition setting unit 152, and stored in the storage area 1472 of the recording unit 140. In addition, the position setting unit 162 receives and sets as position information 1622 position information inputted by the examiner through the operation unit 108, which is a hint for or helps the measurement position computation unit B 114 to perform computation for identifying the measurement position, and the position setting unit 162 stores the position information in a storage area 1474 of the recording unit 140. The auxiliary information generation unit 164 generates the auxiliary information 1642 on the basis of the measurement condition 1522 stored in the storage area 1472 and the position information 1622 stored in the storage area 1474, and stores the auxiliary information 1642 in a storage area 1476.

The measurement position computation unit B 114 of the measurement position computation unit 110 receives the tissue image 1062 generated by the ultrasonic image generation unit 106, reads out the measurement condition 1522 from the storage area 1472, reads out the auxiliary information 1642 from the storage area 1476, and compares the image with the image information database 141 based on these pieces of information, thereby computing the measurement position information 1102. The computed measurement position information 1102 is stored in a storage area 1482 of the recording unit 140, for use by the measurement value computation unit 122.

Input timing for the examiner to provide an input through the operation unit 108 to the above-described position setting unit 162 or measurement condition setting unit 152 may be when an image is being captured or made static. An input operation is acceptable as needed, and detected by the control unit 170, and then the position setting unit 162 which utilizes input information and/or the measurement condition setting unit 152 operates to set the position information 1622 and/or the measurement condition 1522, and on the basis of this setting, the auxiliary information generation unit 164 operates to output the auxiliary information 1642. Further, the measurement position computation unit B 114 of the measurement position computation unit 110 operates on the basis of the operation of the auxiliary information generation unit 164. In addition, the measurement value computation unit 122 operates on the basis of the operation of the measurement position computation unit 110.

The measurement condition setting unit 152 displays a list of measurement items on the display unit 132. Then, when the examiner inputs a measurement item such as a type of measurement value desired to be obtained through the operation unit 108 using, for example, a method of making a selection from the list, and further inputs the number of measurement positions and a measurement position computation scheme required for measurement position setting using, for example, a method of making a selection from displayed items, the measurement condition setting unit 152 sets the inputted information as the measurement condition 1522. The set measurement condition 1522 is stored in the storage area 1472 of the recording unit 140 for use by the measurement position computation unit A 112 or the measurement position computation unit B 114 of the measurement position computation unit 110 or the auxiliary information generation unit 164.

The above-described measurement items may include various kinds of items of measurement, such as of distance, speed, area, volume, and distortion, performed in ultrasound examination by the ultrasonic diagnostic device 100. The above-described computation scheme is, for example, image recognition computation, which includes, for example, a statistical estimation method, image edge detection processing, and a pattern matching method. Further, the computation scheme includes a computation scheme which sets a relatively rough area used by the auxiliary information generation unit 164, such as a computation scheme for setting a measurement position candidate region, and a computation scheme for setting a specific position used by the measurement position computation unit 110; that is, a measurement position for computing a measurement value.

The auxiliary information setting unit 160 includes the position setting unit 162 and the auxiliary information generation unit 164 as described above. The position setting unit 162 receives position information used for the auxiliary information generation unit 164 to compute, for example, a measurement position candidate region, on the basis of an input operation of the examiner; sets the position information 1622 on the basis of, for example, a decision operation; and stores it in the storage area 1474. The position information 1622 has a function of specifying a position in relation to a displayed image, such as being able to define it using a shape including a point, a line, a plane, and the like. Although the position information 1622 may include information directly specifying a measurement position obtained by the measurement position computation unit B 114 of the measurement position computation unit 110, it is rather information which covers a broader area, and indicates an area including the above measurement position, a neighborhood of the above measurement position, or a characteristic position of a body tissue. The position information 1622 inputted by the examiner and set by the position setting unit 162 is displayed as an image on the display unit 132 by the output image generation unit 130. The examiner inputs and sets the position information 1622 while viewing the displayed tissue image 1062, which has been generated by the ultrasonic image generation unit 106 and displayed on the display unit 132, or while viewing a combined image, which is the tissue image 1062 combined with the measurement position information 1102 computed by the measurement position computation unit 110, displayed on the display unit 132, and accordingly the position information 1622 has a function of indicating a positional relationship with respect to the tissue image 1062 or the measurement position information 1102.

The auxiliary information generation unit 164 generates the auxiliary information 1642 on the basis of the position information 1622 from the position setting unit 162 and the measurement condition 1522 from the measurement condition setting unit 152, and passes the auxiliary information 1642 to the measurement position computation unit B 114 of the measurement position computation unit 110. The measurement condition 1522 from the measurement condition setting unit 152 contains information about the number of measurement positions and a measurement position computation scheme, and the auxiliary information 1642 from the auxiliary information generation unit 164 contains the position information 1622 set by the position setting unit 162. The auxiliary information generation unit 164 sets a measurement position candidate region in which a measurement position may exist, on the basis of the above-described number of measurement positions and measurement position computation scheme, and also of the position information 1622.

As described above, the auxiliary information generation unit 164 calculates the measurement position candidate region by the computation scheme which sets the relatively rough position at which a measurement position may exist using the position information 1622 set by the position setting unit 162. This information is passed as the auxiliary information 1642 to the measurement position computation unit B 114 of the measurement position computation unit 110. In a specific example, the above-described computation performed by the auxiliary information generation unit 164 detects a position having a characteristic of the measurement position by pattern matching processing or edge detection processing, around a position indicated by the position information 1622 set by the position setting unit 162, and sets a region around the detected position, as a measurement position candidate region. In another scheme, a past pattern of measurement positions is statistically analyzed, a measurement position is estimated from the position information 1622 using this analysis result, and a region around this estimated position is set as a measurement position candidate region.

The operation unit 108 is an interface on which various kinds of operations are performed for control of the ultrasonic diagnostic device 100, and is used for, for example, inputting position information to the position setting unit 162, inputting a measurement condition to the measurement condition setting unit 152, and the like. The operation unit 108 has a keyboard, a pointing device, a voice input device, etc. The pointing device may be a mouse, a track ball, a touch panel provided on a display screen of the display unit 132, or the like.

The control unit 170 includes a CPU (Central Processing Unit) for various kinds of processing of the ultrasonic diagnostic device 100, and controls the whole system of the ultrasonic diagnostic device 100, as well as performing processing of the measurement setting unit 150, such as performing processing of the auxiliary information generation unit 164 on the basis of the measurement condition 1522 and the position information 1622 set by the operation unit 108. The function of each of the components illustrated as respective blocks in FIG. 1 is achieved by the control unit 170 executing application software for implementing the respective blocks. Many pieces of application software are stored for this purpose, and activation and execution of these pieces of application software are managed by an operating system (OS), which is one type of system software, so that a necessary piece of application software is executed at timing when it is required.

Accordingly, in the present embodiment, an operation performed on the operation unit 108 by the examiner is constantly detected by the control unit 170, and a necessary piece of application software is activated on the basis of the detection and then executed. Therefore, an operation on the operation unit 108 by the examiner can be accepted at any time, so that required application software is activated and executed based on the examiner's operation on the operation unit 108 even when, for example, a moving image is being captured or an image is static. For example, when input to the position setting unit 162 or input of a measurement condition to the measurement condition setting unit 152 through the operation unit 108 is performed, processing of the position setting unit 162 or the measurement condition setting unit 152 is executed on the basis of the input operation, and processing of the auxiliary information generation unit 164 is executed, and furthermore, processing of the measurement position computation unit B 114 of the measurement position computation unit 110 and the measurement value computation unit 122 are executed. For example, an execution condition of processing of the measurement position computation unit 110 may be defined so that the measurement position computation unit A 112 or the measurement position computation unit B 114 of the measurement position computation unit 110 operates at each characteristic time phase according to a measurement condition, or the measurement position computation unit may be configured to operate constantly so as to update a measurement value for each frame.

The recording unit 140 stores data such as a signal, an image, setting data, and a measurement value generated by the above described components, and also stores a program for operating various systems constituting the ultrasonic diagnostic device 100, details of computation such as measurement computation, a database used for measurement computation, a database of history information, etc. The recording unit 140 is a storage medium, such as a semiconductor memory, an optical disk, a magnetic disk, or the like. The storage medium may include not only a storage medium provided inside the ultrasonic diagnostic device 100, but also an external storage medium connected via a network.

[Description of Database]

Next, with reference to FIG. 2, there will be described typical storage contents stored in the recording unit 140; particularly, the image information database 141 which is used by the measurement position computation unit A 112 and the measurement position computation unit B 114 of the measurement position computation unit 110. As described above, in the recording unit 140, many pieces of application software and system software for performing processing of the blocks; i.e., the components illustrated in FIG. 1, are stored, and furthermore, for data transfer between these blocks, the image 1302 generated by the output image generation unit 130, the measurement position information 1102 computed by the measurement position computation unit A 112 and the measurement position computation unit B 114 of the measurement position computation unit 110, the measurement value 1202 computed by the measurement value computation unit 122, the measurement condition 1522 set by the measurement condition setting unit 152, the position information 1622 set by the position setting unit 162, and the auxiliary information 1642 generated by the auxiliary information generation unit 164 are held in the storage area 1462, the storage area 1482, a storage area 1484, the storage area 1472, the storage area 1474, and the storage area 1476, respectively. In these areas, update is performed each time a new setting or computation result is outputted, or old data is erased each time a predetermined number of pieces of data are accumulated.

The image information database 141 used for obtaining a measurement position by the measurement position computation unit A 112 and the measurement position computation unit B 114 of the measurement position computation unit 110 is stored in the recording unit 140. The image information database 141 is stored such that a search is possible for each part, and data about the heart is stored in a large category 1412, and data about other parts, for example, a fetus, is stored in a large category 1414. In this way, pieces of data categorized into many large categories are stored corresponding to parts.

Each large category has many categories, and as an example, the large category 1412 has a category 1422 as the heart's long axis information, a category 1423 as the heart's short axis information, a category 1424 as two-chamber information, a category 1425 as four-chamber information, etc. The large category 1414 has a category 1415, etc. Each category has a plurality of or a large number of pieces of image measurement information 1430. In FIG. 2, since it is complicated to show all of reference numerals 1430, just one is shown as a representation, and the others are omitted. Each piece of image measurement information 1430 includes measurement position information 1432, image information around a measurement position 1434, image information 1436, and measurement condition information 1438.

Figure 4:
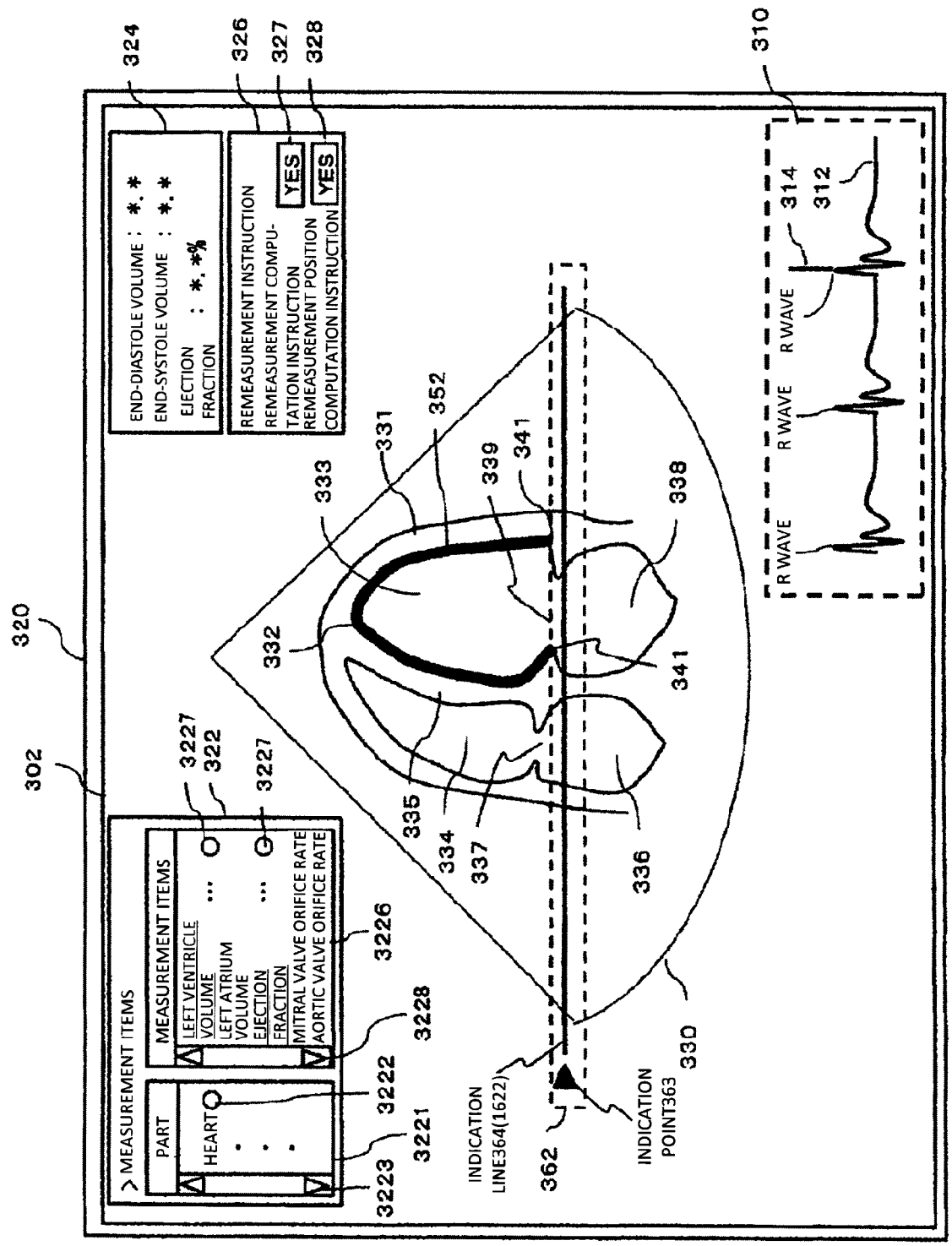
FIG. 4 is an illustrative diagram illustrating an image displayed on a display unit.

FIG. 30 shows one example of a database 1500 about measurement conditions which are inputted through the operation unit 108 on the basis of operation of the measurement condition setting unit 152 and set by the measurement condition setting unit 152 (hereinafter referred to as a measurement condition database 1500). The measurement condition database 1500 has as items a part 1510, a measurement item 1520, a measurement position 1530, the number of measurement 1540, a measurement computation 1550 which indicates details of computation processing, and the like. To obtain a measurement value specified by the measurement item, the measurement condition database 1500 is searched using the part 1510 or the measurement item 1520 as a search parameter on the basis of contents described in measurement items 322 shown in FIG. 4 and other figures, and the measurement position of a target to be computed is read out and identified. The contents described in measurement the items 322 are contents inputted through the operation unit 108 on the basis of operation of the measurement setting unit 150, and objects marked with a setting mark 3222 and a setting mark 3227 in FIG. 4 are set contents, and the measurement condition database 1500 is searched using, as a search parameter, a part or a measurement item marked with the setting mark 3222 or the setting mark 3227.

For example, in an example where the volume of a cardiac ventricle of a heart is obtained as a measurement value, when an annulus portion and a cardiac apex portion are key tissues, and a contour line is to be determined for computing the volume as the measurement value, it is very important to identify the annulus portion and the cardiac apex portion as described below in detail with reference to some drawings. As used herein, a tissue which is important for computing a measurement value as described above is referred to as a key tissue, and a measurement position of a key tissue which is a position at which the key tissue exists is referred to as a key position. Even if a key tissue has not been identified in the measurement condition database 1500, and has been identified just as a contour line as described below, a position inputted by the examiner using an indication point 363 or the like is an important position for correctly computing a measurement value, and is used in computation as a key position for determining the measurement position.

[Description of Overview of Processing Procedure]

Figure 3:
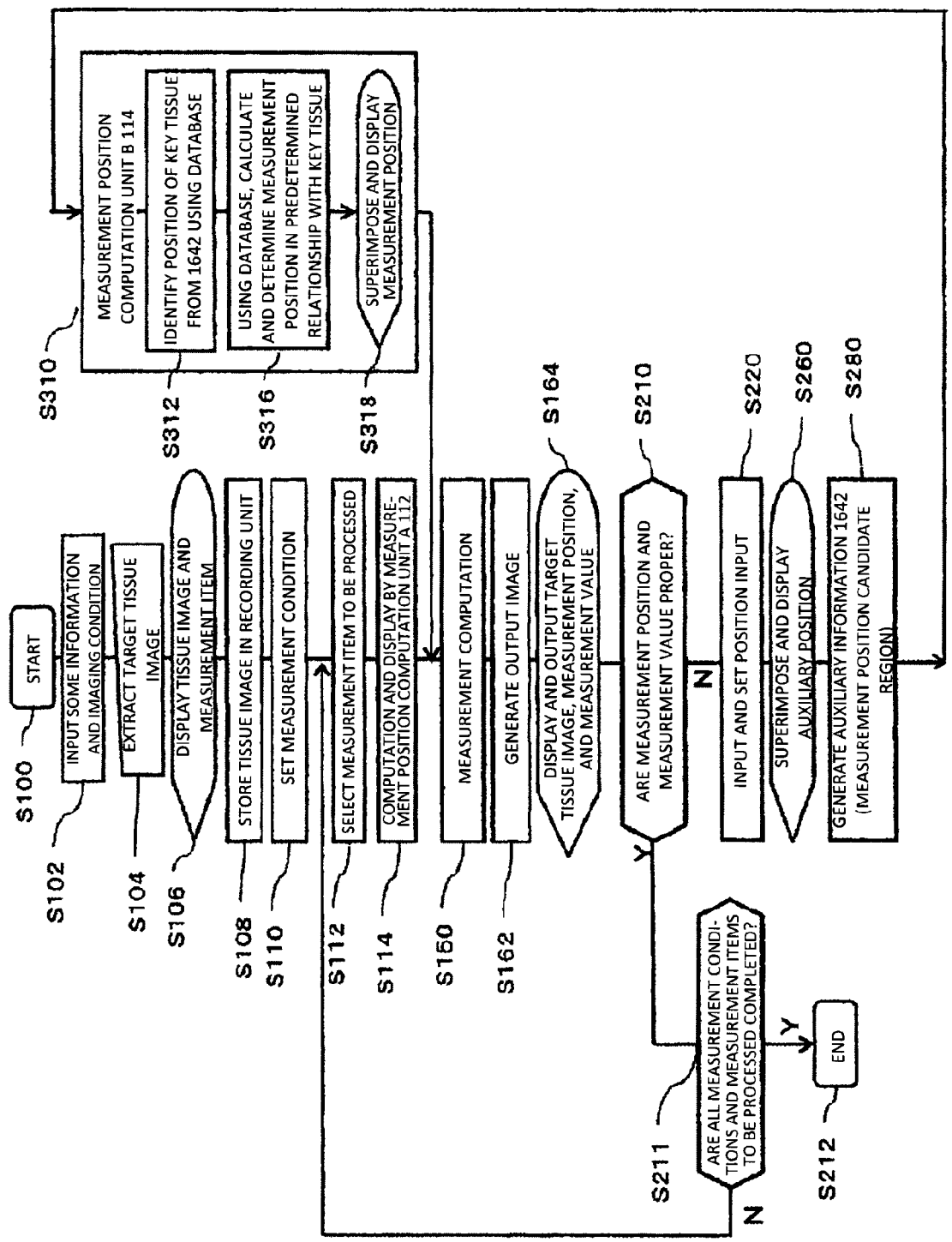
FIG. 3 is a flowchart illustrating an overview of operation of the ultrasonic diagnostic device.

Next, an overview of operation of the ultrasonic diagnostic device 100 will be described using the flowchart shown in FIG. 3. The flowchart of FIG. 3 illustrates a procedure of processing performed by operations of the control unit 170 and the components shown in FIG. 1. First, operation of the ultrasonic diagnostic device 100 starts in step S100, then in step S102, some information about the subject 2 is inputted, and furthermore some input necessary for generating and displaying an ultrasonic image is inputted, and an imaging condition and the like are also inputted. The examiner brings the probe 103 into contact with the subject 2, the ultrasonic signal generation unit 102 having the probe 103 sends and receives an ultrasonic signal to and from a body tissue, and processes the ultrasonic signal based on the received ultrasonic waves. This ultrasonic signal is sent to the ultrasonic image generation unit 106, and the ultrasonic image generation unit 106 generates an ultrasonic image that is a tissue image according to an inputted imaging condition. In other words, a target tissue image is extracted (step S104). The generated ultrasonic image is combined with other data by the output image generation unit 130 and displayed on the display unit 132 (step S106), and further stored in the storage area 1462 of the recording unit 140 (step S108).

The present embodiment will be described using a heart as an example of a measured part. FIG. 4 illustrates an image which is generated by the ultrasonic image generation unit 106 and displayed on the display unit 132 by the output image generation unit 130 in step S106. On a display screen 320 of the display unit 132, an image 302 generated by the output image generation unit 130 is displayed, and on the image 302, an ultrasonic image 330 generated by the ultrasonic image generation unit 106 and an electrocardiogram 310 are displayed. As described further below, the measurement items 322 represented in a tabular form and measurement values 324 represented in a tabular form are displayed, and an indication of position input 362 used for creating the position information 1622 is displayed.

As described later, a remeasurement instruction field 326 is provided for an instruction in a case where the measurement values 324 is desired to be recomputed by remeasurement when the measurement values 324 is computed by the measurement value computation unit 122 and displayed. In order to give an instruction to perform remeasurement and computation by the measurement value computation unit 122, a remeasurement computation instruction 327 is selected, and in order to give an instruction to perform measurement position computation by the measurement position computation unit B 114 and processing of the measurement value computation unit 122 based on its result, a remeasurement position computation instruction 328 is selected. When the remeasurement computation instruction 327 is given, the measurement value computation unit 122 operates so that the measurement result is displayed again in the measurement values 324. In addition, when the remeasurement instruction field 326 is selected, position information input by the position input 362 to the position setting unit 162 is allowed. When the remeasurement computation instruction 327 or the remeasurement position computation instruction 328 is selected, a remeasurement state occurs, and an indication of the remeasurement state is displayed. For example, the display of the selected item "remeasurement computation instruction" or "remeasurement position computation instruction" is changed in color, comes into a blinking state, or the like, so as to notify the examiner that a remeasurement mode is in effect.

For example, on the ultrasonic diagnostic device, the examiner needs to use both hands for operation, and it is desirable to avoid complexity of operation. Even if an instruction is given with respect to the remeasurement instruction field 326, by simply inputting the position input 362, the measurement position computation unit B 114 operates so that a mode for recomputing a measurement position is entered as if an operation for the remeasurement position computation instruction 328 is performed. In this mode, an indication for notifying the examiner that a remeasurement position computation mode is in effect is displayed; for example, the display of the item of the remeasurement position computation instruction 328 is changed in color, blinking, or the like.

The ultrasonic image 330 represents an image of an apical four-chamber view of the heart as an example in this description, and the displayed ultrasonic image of the heart 331 has a cardiac apex portion 332, a left ventricle 333, a right ventricle 334, an interventricular septum 335, a right atrium 336, a tricuspid valve 337, a left atrium 338, a mitral valve 339, an annulus portion 341, and the like. The displayed electrocardiogram 310 has an electrocardiographic waveform 312 and a time phase marker 314. The heart 331 changes periodically, and a changing image of the heart 331 may be displayed in the ultrasonic image 330, and alternatively, an image of the heart 331 in synchronization with the electrocardiographic waveform 312 may be displayed so that an image in a certain state in synchronization with the periodic change of the heart 331 is displayed. Synchronization timing to generate a tissue image can be identified by selecting a position of the time phase marker 314 with respect to the electrocardiographic waveform 312, and if the position of the time phase marker 314 with respect to the electrocardiographic waveform 312 is changed, the synchronization timing to generate a tissue image is changed.

Further, various measurements can be performed using the ultrasonic image 330 displayed on the display screen 320, and for performing such measurement, the examiner operates the operation unit 108 to input a measurement condition to the measurement condition setting unit 152 in step S110 of the flowchart of FIG. 3. For example, when the tissue image 1062 generated by the ultrasonic image generation unit 106 is displayed on the display screen 320 by the output image generation unit 130, the measurement items 322 are displayed in a measurement item display field. Since there are many items to be displayed as the measurement items 322, measurement items are categorized for each part, and when a part is selected in a part display field 3221, a measurement item related to the selected part is displayed in a measurement item display field 3226. When a part is selected, the setting mark 3222 is displayed corresponding to the selected part. Further, in a case where there are many types of parts, the display contents can be changed by manipulating a display content change mark 3223. Similarly, in the measurement item display field 3226, when a measurement item is selected, the setting mark 3227 is displayed corresponding to the selected measurement item. Further, in a case where there are many measurement items, the display of the measurement items can be changed using a display content change mark 3228.

In the description of the example shown in FIG. 4, it is assumed that measurement of the volume of a left ventricle and measurement of an ejection fraction which can be calculated from the volume are selected as measurement items desired to be measured by the examiner. In a method for selecting a measurement item, a selection may be performed from a displayed list as described above, or the measurement item may be previously assigned to an input key of the operation unit 108 so that the measurement item is selected by operating the input key. The measurement items may include various kinds of items of measurement, such as distance, speed, area, volume, and distortion, performed in, for example, ultrasound examination. Once a measurement item is set, the database is searched to read out and determine the number of measurement positions required for the measurement and details of processing such as a computation scheme (hereinafter referred to as a measurement condition). These pieces of information have been stored in the recording unit 140, and each time a measurement item is set, the measurement condition is read out and set.

In the example shown in FIG. 4, a plurality of types of measurement conditions have been selected. One is measurement of the volume of a left ventricle, and the other is measurement of an ejection fraction. In this way, a plurality of types of measurement conditions can be selected. The plurality of measurement items are sequentially processed. In step S112, a measurement item to be processed is selected. For example, measurement of the area of the left ventricle is selected, and subsequently processing for measuring the area of the left ventricle is performed first. After the measurement of the left ventricle area is completed, whether all the measurements are completed is determined in step S211, the execution of the control unit 170 proceeds from step S211 to step S112, and a measurement item to be processed next is selected in step S112. In this way, measurement of a plurality of items is sequentially performed.

In step S114, the measurement position computation unit A 112 of the measurement position computation unit 110 computes a measurement position using the ultrasonic tissue image 1062 on the basis of the set measurement conditions. For example, in a case where the left ventricle volume of the heart is selected as a measurement item as shown in FIG. 4, a contour line 352 of the heart 331 needs to be computed. To this end, details of computation for obtaining heart contour information is read out by searching in step S110, and given as a measurement condition to the measurement position computation unit 110. The measurement position computation unit A 112 of the measurement position computation unit 110 performs computation for extracting the contour of the heart based on the given measurement condition. This computation would obtain the heart contour information including the contour line 352 if successful.

For computation of contour extraction performed by the measurement position computation unit A 112 of the measurement position computation unit 110, for example, an image recognition technique may be used, or a technique for edge detection of a cardiac wall, contour detection using a dynamic contour module, or the like may be used. The contour line 352 computed by the measurement position computation unit A 112 of the measurement position computation unit 110 is superimposed on the ultrasonic image 330 and displayed as a line. The above-described measurement position computation such as contour extraction computation is executed at a time phase suited to a measurement item given from a measurement condition. For example, when an end-diastole volume is computationally calculated, the ultrasonic image 330 obtained at an R-wave time phase of the electrocardiographic waveform 312 is used. A time phase of the electrocardiographic waveform 312 is specified using the time phase marker 314 such as a bar, and if the position of the time phase marker 314 with respect to the electrocardiographic waveform 312 is changed, the time phase is changed. Further, to obtain the volume of cardiac ventricle or atrium in synchronization with each time phase, the processing performs measurement computation for each frame. Further, all contours between heartbeats may be extracted by automatically extracting a contour at an R wave and tracking positions of contour points for each frame until the next R wave. If the contour line for each frame has been extracted, an ejection fraction can be calculated using the end-diastole volume and end-systole volume.

Next, in step S150, computation for calculating a selected measurement item is performed on the basis of the above-described measurement condition. Computation of the left ventricle volume of the heart is performed by applying a disk method or Area Length method thereto using coordinate information of the contour line. The measurement value is superimposed on the ultrasonic image and displayed as the measurement value 324. In addition, as another measurement computation item, computation of a distance, a flow rate, or a distortion may be performed.

As shown in FIG. 4, the output image generation unit 130 generates the image 302 in step S162, which is the ultrasonic image 330 generated by the ultrasonic image generation unit 106 on which the contour line 352 computed by the measurement position computation unit A 112 in step S114 is superimposed, and further the measurement items 322 and the measurement values 324 are superimposed, and displays the image 302 on the display screen 320 of the display unit 132 (step S164). In addition, in a case where an auxiliary position is inputted in step S220 as described later or the auxiliary information 1642 is generated in step S280, the image 302 on which such information is also superimposed is displayed in step S164.

In step S210, the examiner views the image 302 displayed on the display screen 320 to determine whether or not the measurement position such as the contour line 352 computed by the measurement position computation unit A 112 in step S114 is proper, and further, whether or not the measurement values 324 measured by the measurement value computation unit 122 in step S150 are proper. For example, whether or not the contour line 352 properly fits the wall surface of the left ventricle 333 of the heart via the annulus portion 341 and the cardiac apex portion 332 is checked. Further, whether or not the measurement value deviates from a medically expected area is checked. If the examiner is satisfied with the processing result of step S114 and step S150, the processing proceeds from step S210 to step S211 in response to an instruction of the examiner, and whether measurement with respect to all the measurement items is completed or not is determined in step S211. If it is not completed, step S112 is executed, and the above-described operation is repeated. If it is determined to be completed in step S211, step S212 is executed, and a series of measurement processing operations started from step S100 is terminated. On the other hand, if this result is not satisfactory, and the measurement value or the measurement position is determined to be improper, the processing proceeds from step S210 to step S220. For example, a determination that the measurement value or the measurement position is improper may be based on a selection being made from the remeasurement instruction field 326 shown in FIG. 4 or the examiner starting an operation for position input performed in step S220.

The image 302 created in step S162 has the remeasurement instruction field 326 displayed therein, and if, for example, the remeasurement computation instruction 327 or the remeasurement position computation instruction 328, which is an item of the remeasurement instruction field 326, is selected, the processing proceeds from step S210 to step S220. Alternatively, an input operation of the position input 362 is performed for the image 302 displayed in step S164, and the processing proceeds from step S210 to step S220. In step S220, if there is inputted position information with auxiliary function which helps the measurement position computation unit B 114 accurately compute a measurement position, for example, the contour line 352 (hereinafter referred to as auxiliary information), the measurement position computation unit B 114 is allowed to more accurately identify a measurement position, such as the contour line 352 of a cardiac ventricle of the heart using the auxiliary information as described below.

Using an example especially about the annulus portion 341 as a specific example, step S210 and step S220 will be described. Shapes of hearts vary depending on the individual and on pathological change, and the position of an annulus portion may be deviated from its normal position. In this case, the position of the annulus portion in an ultrasonic image also deviates from the normal position. Therefore, in computation by the measurement position computation unit A 112 using the image information database 141, there may be a case where the annulus portion 341 cannot be correctly detected. However, correct detection of a position of the annulus portion 341 is important for performing various types of measurement about hearts such as measurement of a left ventricle volume. In this embodiment, the position input 362 is inputted, which functions to specify a position in the depth direction of right and left annulus portions. In the embodiment, an indication line 364 is set and displayed by the position input 362.

If the examiner inputs and sets the indication point 363 to the position setting unit 162 through the operation unit 108 in step S220, the indication line 364 is created as the position information 1622 by the position setting unit 162, and the position information 1622 is superimposed and displayed on the ultrasonic image 330 by the output image generation unit 130. For example, the examiner operates a pointing device such as a track ball or a mouse to input the indication point 363, and accordingly the position setting unit 162 creates the indication line 364 on the basis of the indication point 363, and superimposes it on the ultrasonic image 330 as the position information 1622 so as to display the position input 362 (step S260).

In the position setting unit 162, for example, when the indication point 363 is specified through the operation unit 108, a horizontal or vertical line is created based on the indication point 363 to create the indication line 364 so that the position input 362 is created as the position information 1622. If the indication point 363 is positioned to the left of the ultrasonic image 330, the indication line 364 from the indication point 363 as the starting point is created toward the right side of FIG. 4; that is, in the direction toward the ultrasonic image 330 from the indication point 363 as shown in FIG. 4. On the other hand, if the indication point 363 is positioned to the right of the ultrasonic image 330, the indication line 364 from the indication point 363 as the starting point is created toward the left side; that is, in the direction toward the ultrasonic image 330 from the indication point 363. Further, if the indication point 363 is positioned under the ultrasonic image 330, the indication line 364 is created upward; that is, in the direction toward the ultrasonic image 330, and if the indication point 363 is positioned above the ultrasonic image 330, the indication line 364 is created downward; that is, in the direction toward the ultrasonic image 330. Although a relationship between the indication point 363 and the ultrasonic image 330 is used in the above description, the indication line 364 may be created in a similar way according to a positional relationship of the indication point 363 with respect to a display position of a target tissue of a measurement item.

Since the ultrasonic image 330 becomes difficult to see due to the position input 362 superimposed on the ultrasonic image 330, it is desirable that the display of the position input 362 disappears after the elapse of a certain period of time. After being created by the position setting unit 162, the position information 1622 based on display of the position input 362 is stored and held, and even after its display disappears from the image 302, the position information 1622 continues to be held in the storage area 1474 of the recording unit 140. As described below with reference to a flowchart, by selecting the displayed indication line 364 by the pointing device of the operation unit 108 and shifting parallel or rotating the selected indication line 364, the indication contents indicated by the position input 362; that is, contents of the position input and the position information 1622, can be changed. There may be a case where the examiner performs some operations simultaneously and therefore cannot specify an optimal position properly from the beginning. Even in this case, fine adjustment can be performed by, for example, moving a cursor closer to the position input 362 to select the position input 362 and shifting parallel or rotating the position input 362.

In step S280, the auxiliary information generation unit 164 acquires the position information 1622 displayed as the indication line 364 created by the position setting unit 162, from the storage area 1474 of the recording unit 140, and further acquires the measurement condition set by the measurement condition setting unit 152 and stored in the storage area 1472, thereby generating the auxiliary information 1642.

Figure 5:
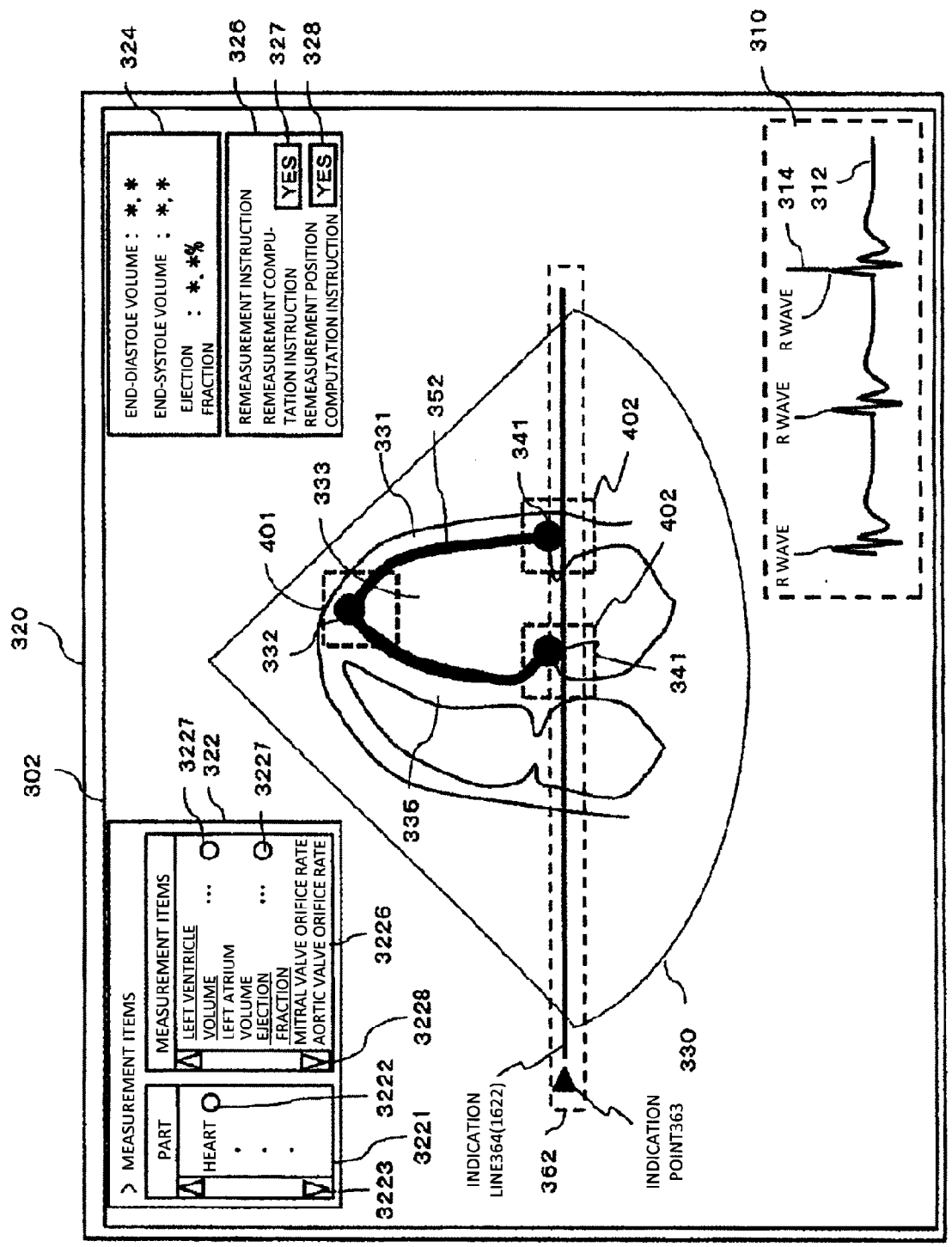
FIG. 5 is an illustrative diagram illustrating an image in which a measurement position candidate region, which is auxiliary information, is displayed on the basis of a position input.

FIG. 5 is an illustrative diagram illustrating a method for generating the auxiliary information 1642 on the basis of the position input 362 by the auxiliary information generation unit 164. Assuming that the annulus portion 341 exists in the vicinity of or in proximity to the position input 362, a positional relationship between the annulus portion 341 and the cardiac apex portion 332 is calculated. In the measurement condition setting unit 152, a computation scheme is set for computationally calculating a measurement position candidate region when the position input 362 is provided near the annulus portion 341 in a case where the volume of the heart is to be measured. FIG. 30 illustrates the measurement condition database 1500 from which a measurement position to be computed, a measurement computation which consists of details of computation used for measurement, and the number of measurements can be retrieved by using as a search parameter a part or measurement item set by the measurement condition setting unit 152.

In a case where the volume of the left ventricle of a heart is measured, as a result of a search of the measurement condition database 1500 using the heart displayed as a part set by the part display field 3221 or the left ventricle volume displayed as an item set by the measurement item display field 3226 in FIG. 5, a contour line, an annulus portion, and a cardiac apex portion are read out as measurement positions 1530. The contour line is necessary for determining the left ventricle volume, but the annulus portion and the cardiac apex portion are also read out as key tissues. The auxiliary information generation unit 164 computes regions in which the annulus portion 341 and the cardiac apex portion 332 are estimated to exist, on the basis of a key tissue which is a measurement condition further retrieved on the basis of an input from the examiner, and outputs a measurement position candidate region 401 and measurement position candidate regions 402, which are the computation results, as the auxiliary information 1642. This auxiliary information 1642 is used for processing of the measurement position computation unit B 114. An operational expression; that is, a computation scheme, is read out from the measurement computation 1550 item of the measurement condition database 1500.

For example, when a y-coordinate of the position input 362 is input into the computation scheme, x and y coordinates of the annulus portion 341 and the cardiac apex portion 332 are calculated in the case where the annulus exists in the position of the y-coordinate. The x and y coordinates are a function of the y-coordinate from the position input 362, and this function is set as the computation scheme. In an alternative method, x and y coordinates of the position input 362 are inputted into the computation scheme. Thus, the computation scheme may be operated to calculate the x and y coordinates of the annulus portion 341 and the cardiac apex portion 332 using a function of the x and y coordinates of the position input 362. When the position input 362 is inputted, both x and y coordinates of the position input 362 may be used as an instruction from the examiner, or only a y-coordinate indicated by the position input 362 may be used as an instruction from the examiner. On the basis of information of the position input 362, computation is performed using a computation scheme stored in the measurement computation 1550 item of the measurement condition database 1500. The measurement computation 1550 item of the measurement condition database 1500 holds not only a computation scheme to be used by the auxiliary information generation unit 164, but also a computation scheme to be used by the measurement position computation unit B 114. In the case of processing of the auxiliary information generation unit 164, a computation scheme for the auxiliary information generation unit 164 is selected to be used from computation schemes stored in the measurement computation 1550 item of the measurement condition database 1500.

The auxiliary information generation unit 164 computes the measurement position candidate regions 401 and 402 of the annulus portion 341 and the cardiac apex portion 332 according to the computation scheme. The measurement position candidate regions 401 and 402 may be superimposed and displayed on the ultrasonic image 330 to cause the examiner to recognize the areas of the measurement position candidate regions 401 and 402, or may be held just as internal data without being displayed. Each measurement position candidate region 402 is a computationally calculated result indicating that each includes the annulus portion 341. The measurement position candidate region 401 is a computationally calculated result indicating that it includes the cardiac apex portion 332.

In step S310, the measurement position computation unit B 114 computes a measurement position using the auxiliary information 1642 obtained in step S280. In the case of the measurement position computation performed by the measurement position computation unit A 112 in step S114, the contour of the left ventricle 333 is extracted simply by using the image information database 141. In step S310, the annulus portion 341 and the cardiac apex portion 332 are detected, and then the contour 305 via these portions is extracted. First, in step S312, positions of key tissues, which in this case are the annulus portion 341 and the cardiac apex portion 332; i.e., key positions, are searched for based on the auxiliary information 1642 obtained by the auxiliary information generation unit 164 in step S280. The auxiliary information 1642 represents measurement position candidate regions in this case, and positions in which characteristics of the annulus portion 341 and the cardiac apex portion 332 appear most, as a result of searching within the measurement position candidate regions, are newly determined as the annulus portion 341 and the cardiac apex portion 332 in step S312.

Processing contents of the measurement position computation unit B 114 in this case may also be read out from the measurement computation 1550 of the measurement condition database 1500. For example, while basic processing contents of the measurement position computation unit B 114 are held as a common processing program, a non-common computation section in a case where details of computation are different depending on computation processing contents, e.g., a key tissue, may be read out and used as a special computation scheme from the measurement computation 1550.

In the above-described identification of positions of the annulus portion 341 and the cardiac apex portion 332, searching is performed within the measurement position candidate regions 402 and 401 to calculate values of characteristics of the annulus portion 341 and the cardiac apex portion 332. At this time, indexes that quantify a likelihood of annulus portion and a likelihood of cardiac apex portion are provided, the likelihood of annulus portion and the likelihood of cardiac apex portion are computed within the measurement position candidate regions 402 and 401, and it is determined through comparison whether their characteristics match the indexes. Positions having a high degree of matching between the computed index and the position index held in advance are defined as positions of the annulus portion 341 and the cardiac apex portion 332; that is, key positions of key tissues. Position display of the position input 362 is performed on the basis of an index having a high degree of matching based on the computed characteristic matching degree. This position display may be performed by highlighting, such as coloring a position having a high degree of matching on the indication line 364. For example, if the position input 362 has been set in a position having a high index value of the likelihood of annulus portion, the position display of the position input 362 is emphasized by coloring in operation so that the examiner can operate it easily.

In step S312, a key tissue is identified, and in this example, the annulus portion 341 and the cardiac apex portion 332, and key positions of these key tissues are identified using the image information database 141. Next, in step S316, a measurement position is computationally calculated such that the measurement position has a predetermined relationship with respect to the annulus portion 341 and the cardiac apex portion 332, which are key tissues whose position has been identified. In this embodiment, the contour line 352 which is the measurement position is computed and determined such that it passes through the key tissues; i.e., the annulus portion 341 and the cardiac apex portion 332. The contour line 352 which is the determined measurement position is superimposed and displayed on the ultrasonic image 330 in step S318. In step S150 the measurement value computation unit 122 calculates a measurement value according to the contour line 352 which is the measurement position computationally calculated by the measurement position computation unit B 114 in step S310, and new measurement values are displayed as the measurement values 324 on the image 302 in step S162 and in step S164.

Next, in step S210 the examiner again determines whether or not these measurement position and measurement values are proper. If it is determined to be proper, the execution of the control unit 170 proceeds from step S210 to step S211, and whether or not there is an unprocessed measurement item is determined. If there is any unprocessed measurement item, step S112 is executed again, and the above described operation is repeated. If measurement with respect to all the measurement items is determined to be completed in step S211, the processing proceeds from step S211 to step S212, and a series of processing from step S100 of the flowchart is terminated. By the way, if the examiner further modifies the position input 362 in the image 302 shown in FIG. 4 or FIG. 5, the processing of step S220 then starts, and the series of processing procedures from step S220 to step S330 are performed based on the modification of the position input 362, and the operations of step S150, step S162, and step S164 are further repeated. Also in a case where the position input 362 is newly performed, the processing from step S220 to step S310 and the operations of step S150, step S162, and step S164 are repeated.

[Description of a Method which Uses the Position Input 362 from the Start of Computation of a Measurement Position]

In the above-described embodiment, measurement is automatically performed according to a measurement condition of step S110 in a situation where a position input of step S220 is not yet performed by the examiner at the beginning, and then, the examiner determines the properness of a measurement value, a measurement position, or the like in step S210, and if it is not proper, the position input 362 is inputted in step S220, and modification of the measurement position is performed on the basis of the input. Since in this method, the properness of a measurement value, a measurement position, or the like is determined, and a further input operation is performed if it is not proper, this method has a large effect of reducing the amount of operation by the examiner. Because a measurement item is automatically measured depending on the measurement item or depending on the subject 2, an accurate measurement value is obtained in many cases, and there is a large effect of reducing the burden on the examiner.

However, depending on the measurement item or the state of a subject, a possibility of requiring the examiner to operate the position input 362 may be higher. In this case, it may be desirable that the examiner's operation for the position input 362 is performed first, and the position input 362 is used for computation of all the measurement positions. A particular processing procedure will be described by reference to the flowchart shown in FIG. 6. The basic processing procedure has been described above by reference to the flowchart shown in FIG. 3, and steps given the same reference numerals perform the same processing as in steps in FIG. 3, and a description thereof will be omitted. Step S113 in the flowchart of FIG. 6 is a different step from the flowchart of FIG. 3.

Figure 6:
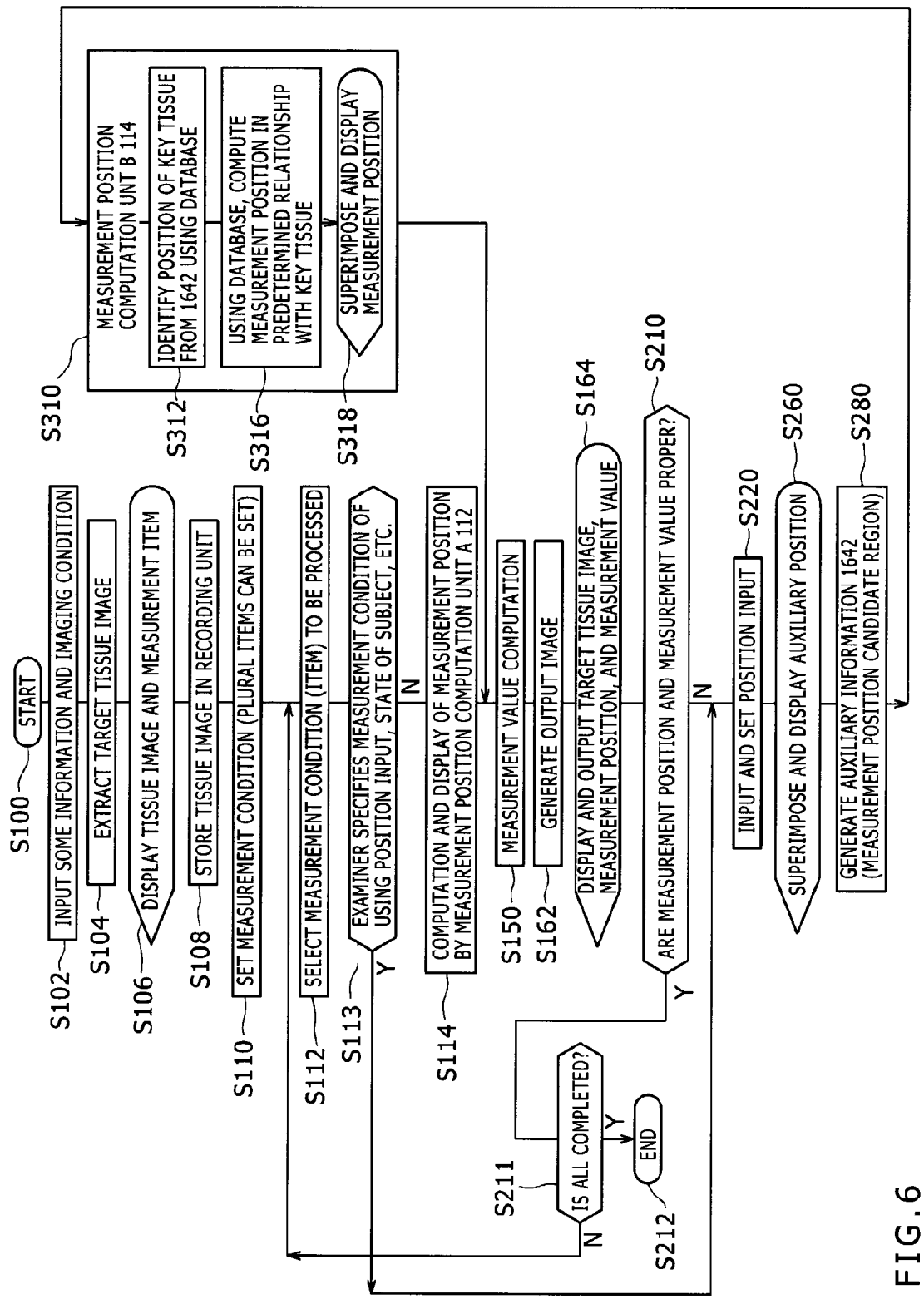
FIG. 6 is a flowchart illustrating another scheme different from the scheme illustrated in FIG. 3.

With reference to FIG. 6, the ultrasonic image 330 which is a tissue image is displayed in step S106, and in step S110 a measurement condition is inputted using the measurement items 322 displayed in the image 302. Display of the measurement items 322 and processing of input of measurement conditions based thereon are performed by the measurement condition setting unit 152 of FIG. 1. When measurement conditions are set by operation of the measurement condition setting unit 152, a measurement condition to be processed is selected in step S112. For example, if two measurement items are inputted and set as a measurement condition as shown in the measurement item display field 3226 of FIG. 4 or FIG. 5, measurement of one of the two measurement items; for example, measurement of a left ventricle volume, is selected first.

In the next step S113, a determination is made as to whether to perform processing of step S220 to step S280 first to obtain the auxiliary information 1642 such as a measurement position candidate region and compute a measurement position using the auxiliary information 1642 by the measurement position computation unit B 114, or to obtain a measurement position by the measurement position computation unit A 112 first without using the auxiliary information 1642 such as the measurement position candidate region. Of course, without the determination of step S113, position input in step S220 may be performed first with respect to computation of all the measurement positions.

In normal measurement processing, in many cases measurement with satisfactory accuracy can be achieved without position input in step S220, and therefore, it may be preferable that position input in step S220 is performed only for a certain measurement condition or for some persons who are the subject 2. In this case, in step S113 a determination is made as to whether position input in step S220 is to be performed first; i.e., whether measurement position computation by the measurement position computation unit B 114 is to be performed from the beginning. For example, as for a measurement item of a predetermined measurement condition, the execution of the control unit 170 proceeds from step S113 to step S220, and step S114 is not performed. Further, if there is a possibility that, for example, the state of a tissue which is a key for a measurement item differs from that of a normal person as determined on the basis of the state of the subject 2, the execution of the control unit 170 proceeds from step S113 to step S220. Further, if the examiner determines to give an instruction to perform position input of step S220 from the beginning, the execution of the control unit 170 also proceeds from step S113 to step S220. This instruction may be given to, for example, the measurement condition setting unit 152 in step S110. To this measurement condition setting unit 152, a measurement item from the measurement items 322 shown in FIG. 4 or FIG. 5 can be inputted as the measurement condition. For each examination item, when input to the examination item is performed, an instruction may be given as to whether or not to perform position input of step S220 from the beginning as described above. Further, because the examiner knows the clinical history, body shape, and the like of the subject 2 when inputting information of the subject 2, the examiner may give an instruction as to whether or not to perform position input of step S220 from the beginning.

According to the embodiment described by reference to the flowcharts of FIG. 3 and FIG. 6, a measurement position computed in step S114 or step S310; that is, contents of the measurement position information 1102 shown in FIG. 1 can be modified by setting the position input 362. The position input 362 inputted in step S220 indicates a characteristic position of a target tissue, and does not need to directly indicate a measurement position and identify an accurate position. Even so, it can improve the accuracy of computation about measurement positions. Therefore, the present embodiment has an effect that even if a tissue such as a heart or a vessel, whose position cannot be finely identified by an examiner because it is moving, is the measurement target tissue, its measurement position candidate region can be computed if the rough position is specified, and the measurement accuracy can be improved using the measurement position candidate region. Further, although the position input 362 is, for example, the indication line 364, which is one piece of information, this information can be used as a position of the annulus portion 341 to estimate a positional relationship with the cardiac apex portion 332. An examiner can modify measurement positions about a plurality of positions by one operation, and therefore there is a large effect to reduce a burden on the examiner in ultrasonic diagnosis whose operation is troublesome. Further, the method to display the position input 362 may be changed depending on whether the target measurement position is near or far, so that the reliability of the position input 362 can be indicated. Accordingly, operation for modifying the measurement position by the examiner is reduced, so that an ultrasonic diagnostic device having improved efficiency of ultrasound examination can be provided.

[Detailed Description of Step S220]

Details of step S220 shown in FIG. 3 and FIG. 6 will be described by reference to FIG. 7 to FIG. 10. After step S164 shown in FIG. 3 or FIG. 6 is executed and measurement positions and the measurement values 324 are displayed, if they are determined to be improper in step S210, the execution of the control unit 170 proceeds from step S210 to step S220. This is not required to come after step S164; step S220 may be started in a case where, as illustrated in step S295 of FIG. 7, operation is performed on the remeasurement instruction field 326 for position input while the other operation is being performed, and the operation of step S298 is considered to be performed considering the input as the input of the indication point 363, or in a case where, as described below, step S297 of FIG. 8 is executed and is determined to be "N," which in step S210 means improper. The start step of a series of procedures of step S220 is described as step S300.

In step S302, information of the position of the indication point 363 of FIG. 4 or FIG. 5, for example, which is a position inputted from a pointing device such as a mouse, is captured from the operation unit 108. Information of the position of the indication point 363 is, for example, coordinates. In step S312, a direction of the position of the indication point 363 is determined in relation to the ultrasonic image 330 or the target tissue of a measurement item, and if the indication point 363 is on the left side, the indication line 364 is generated to the right of the indication point 363 so as to extend toward the ultrasonic image 330 or the tissue. Similarly, when the indication point 363 is to the right of, above, or under the ultrasonic image 330 or the target tissue of the measurement item, the indication line 364 is generated leftward, downward, or upward, respectively. Further, if the position of the indication point 363 is inside the target tissue of the measurement item, the indication line 364 is generated so as to extend in the upward, downward, leftward, and rightward directions from the indication point 363. In step S314, the position input 362 generated in step S312 and having the indication point 363 and the indication line 364 is superimposed and displayed on the ultrasonic image 330.

Figure 9:
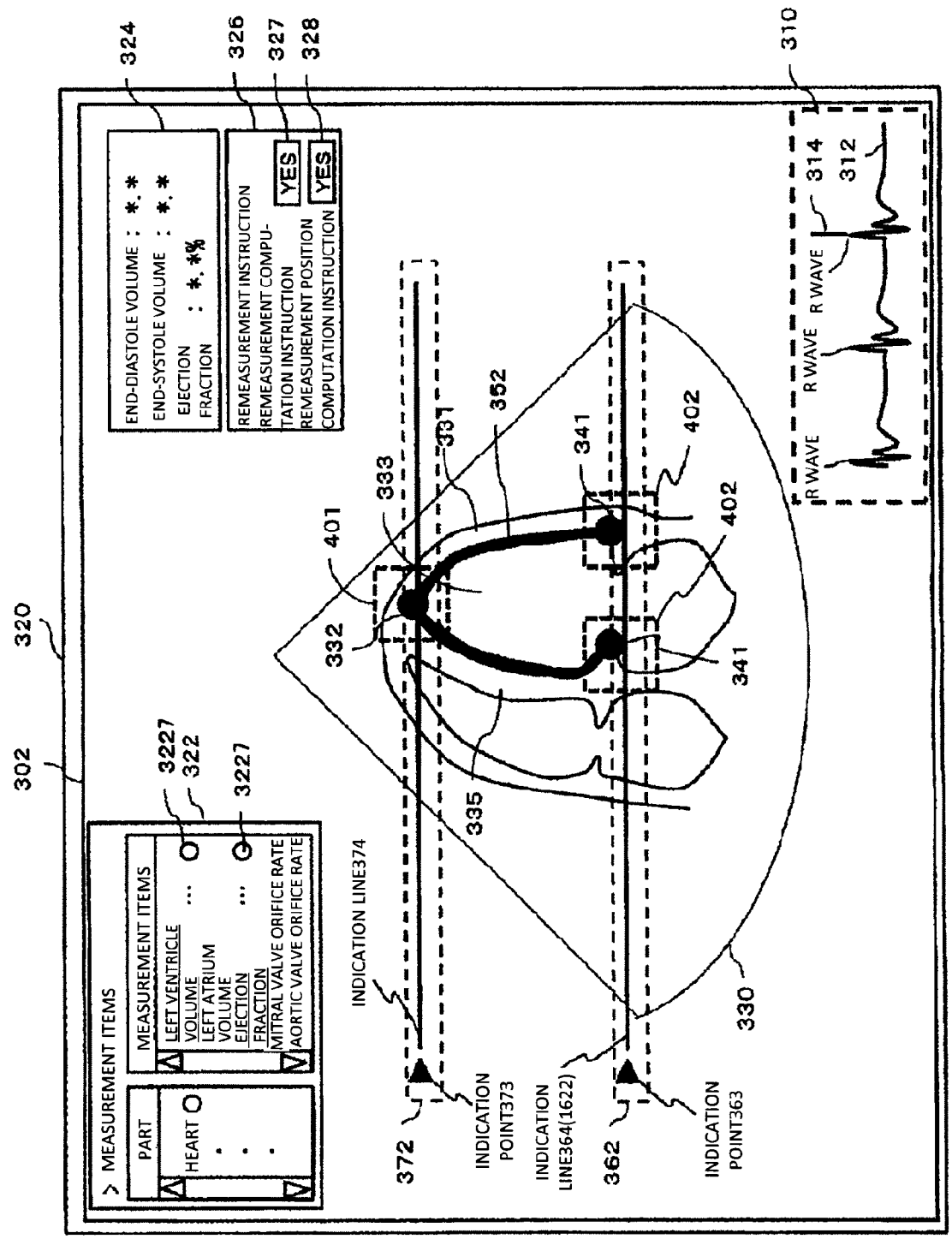
FIG. 9 is an illustrative diagram illustrating an image displayed by another scheme different from the scheme of FIG. 3.

In step S322, a determination is made as to whether or not the indication point 363 is further added. FIG. 9 shows a state where the position input 362 illustrated in FIG. 4 or FIG. 5 is performed multiple times, and a position input 372 which functions similarly to the position input 362 is displayed in addition to the position input 362. If it is determined that the indication point 363 is further added in step S322, step S302 and step S312 are executed with respect to the newly added point. An indication point 373 shown in FIG. 9 is a point which represents the newly added position, and an indication line 374 is generated on the basis of the indication point 373 in step S312 to form the position input 372.

In the embodiment illustrated in FIG. 5, using one position input 362, a plurality of measurement position candidate regions such as the annulus portion 341 and the cardiac apex portion 332 are estimated and computed. In the embodiment shown in FIG. 9, using two position inputs, which are the position input 362 and the position input 372, measurement position candidate regions corresponding to the annulus portion 341 and the cardiac apex portion 332 serving as key tissues are computationally calculated. Specifically, the position of the annulus portion 341 which is a key tissue is estimated from the indication line 364 of the position input 362, and the auxiliary information generation unit 164 calculates a measurement position candidate region of the annulus portion 341 using the measurement condition 1522 on the basis of the estimated position. In addition, the position of the cardiac apex portion 332 which is a key tissue is estimated from the indication line 374 of the position input 372, and the auxiliary information generation unit 164 calculates a measurement position candidate region of the cardiac apex portion 332 which is a key tissue using the measurement condition 1522 on the basis of the estimated position. The method illustrated in FIG. 9 can be applied in a case where more accurate position is desired to be set, or a case where the examiner can afford to operate two bars during examination.

By reference to the measurement position candidate region of the annulus portion 341 and the measurement position candidate region of the cardiac apex portion 332 calculated using the two position inputs, which are the position input 362 and the position input 372, to identify the positions of the annulus portion 341 and the cardiac apex portion 332 which are key tissues for measurement items to be measured in step S312, the contour line 352 is determined so as to be along key positions of the annulus portion 341 and the cardiac apex portion 332 which are key tissues, thereby identifying a measurement position in step S316, so that the measurement position can be accurately computed, or the reliability of the computed measurement position can be improved. With reference to FIG. 9, a usage example of a plurality of position inputs such as the position input 362 and the position input 372 has been described. For example, as described using the electrocardiographic waveform 312, if the indication point 363 is positioned inside the heart 331, two indication lines; that is, vertical and horizontal lines passing through the indication point 363, can be generated. The horizontal line may indicate a region in which the annulus portion 341 exists, and the vertical line may indicate a position of the cardiac apex portion 332. This method allows the examiner to specify positions of a plurality of key tissues by means of a few times of operations.

Figure 7:
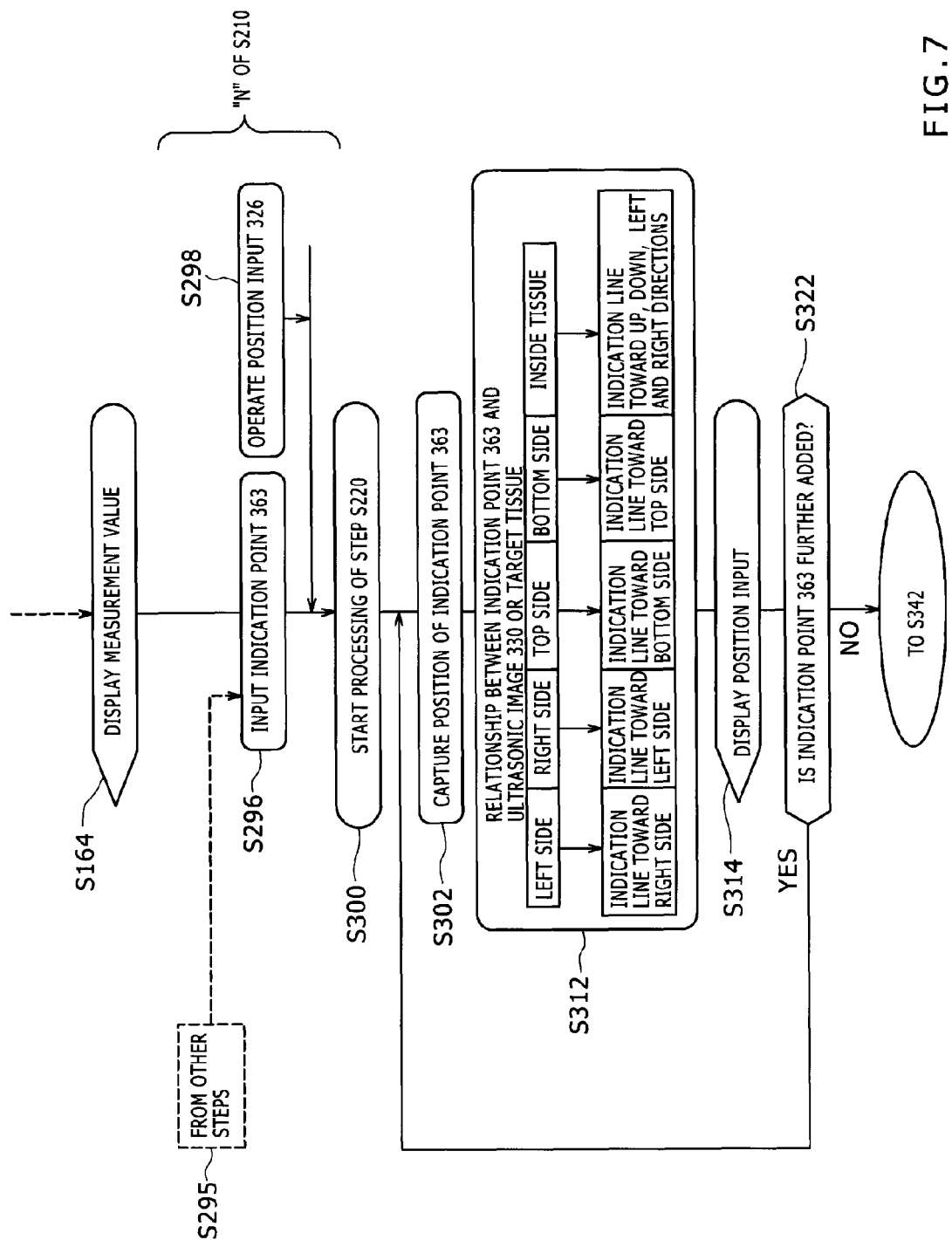
FIG. 7 is an illustrative diagram illustrating details of step S220 of the flowchart as shown in FIG. 3 or FIG. 6.
Figure 8:
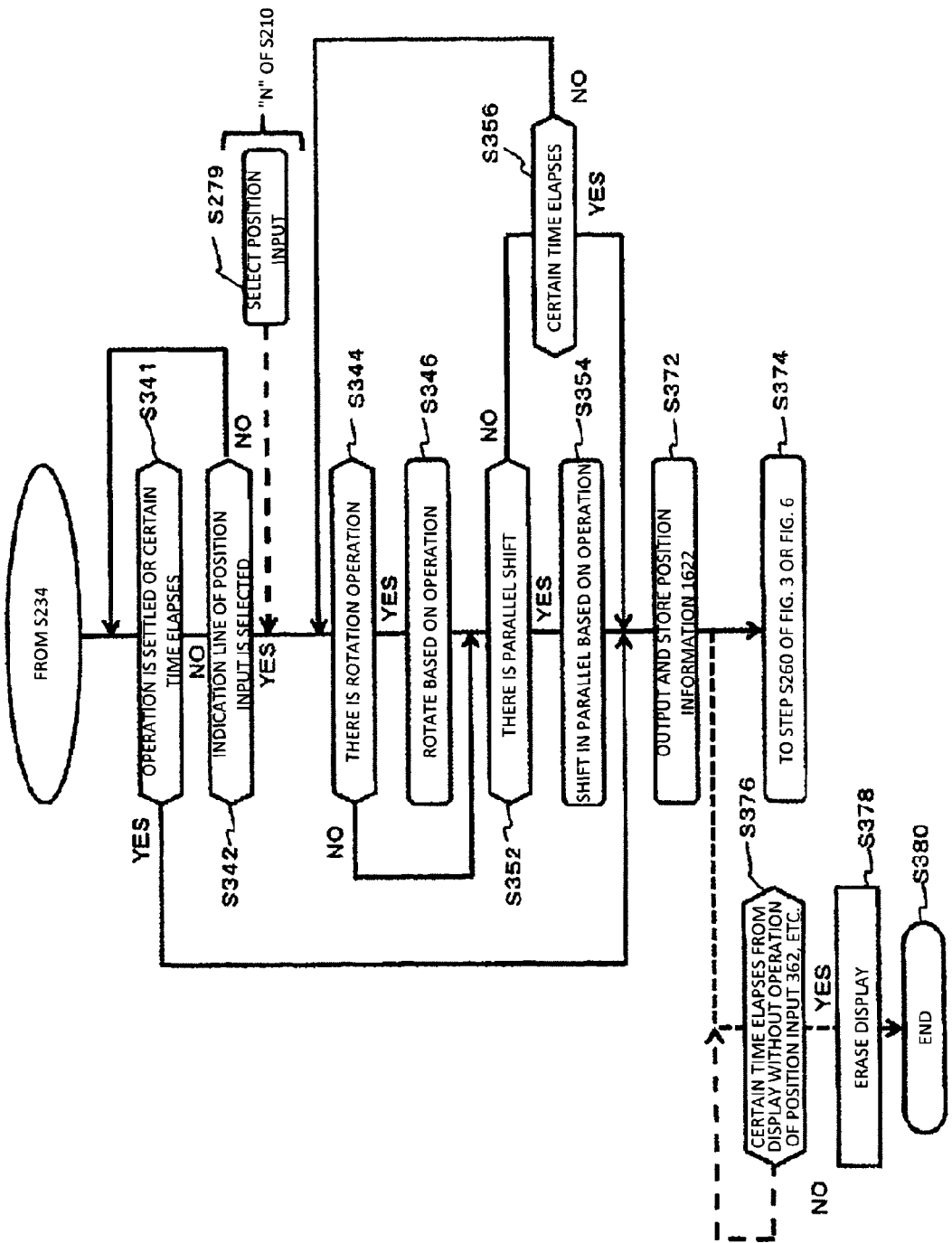
FIG. 8 is an illustrative diagram illustrating details of step S220 of the flowchart as shown in FIG. 3 or FIG. 6, as in FIG. 7.

Next to step S322 of FIG. 7, the execution of the control unit 170 proceeds to step S279 of FIG. 8. If there is performed an operation for settlement of the position input 362 or position input 372 inputted in FIG. 7, or if it is determined that a certain period of time has elapsed in step S341, the execution of the control unit 170 proceeds from step S341 to step S372, and the inputted contents of the position input 362 or the position input 372 are stored as the position information 1622 in the storage area 1474 of the recording unit 140. Then, the execution of the control unit 170 proceeds to step S260 of FIG. 3 or FIG. 6, and processing is performed as shown in FIG. 3 or FIG. 6 as described above. Not only the execution of the control unit 170 proceeds to a step of FIG. 8 after FIG. 7, but also it is always possible that displayed position inputs such as the already displayed position input 362 or position input 372 can be specified using the operation unit 108, and when an operation for specifying a displayed position input is performed (step S279), the control unit 170 executes step S344 of FIG. 8.

Figure 10:
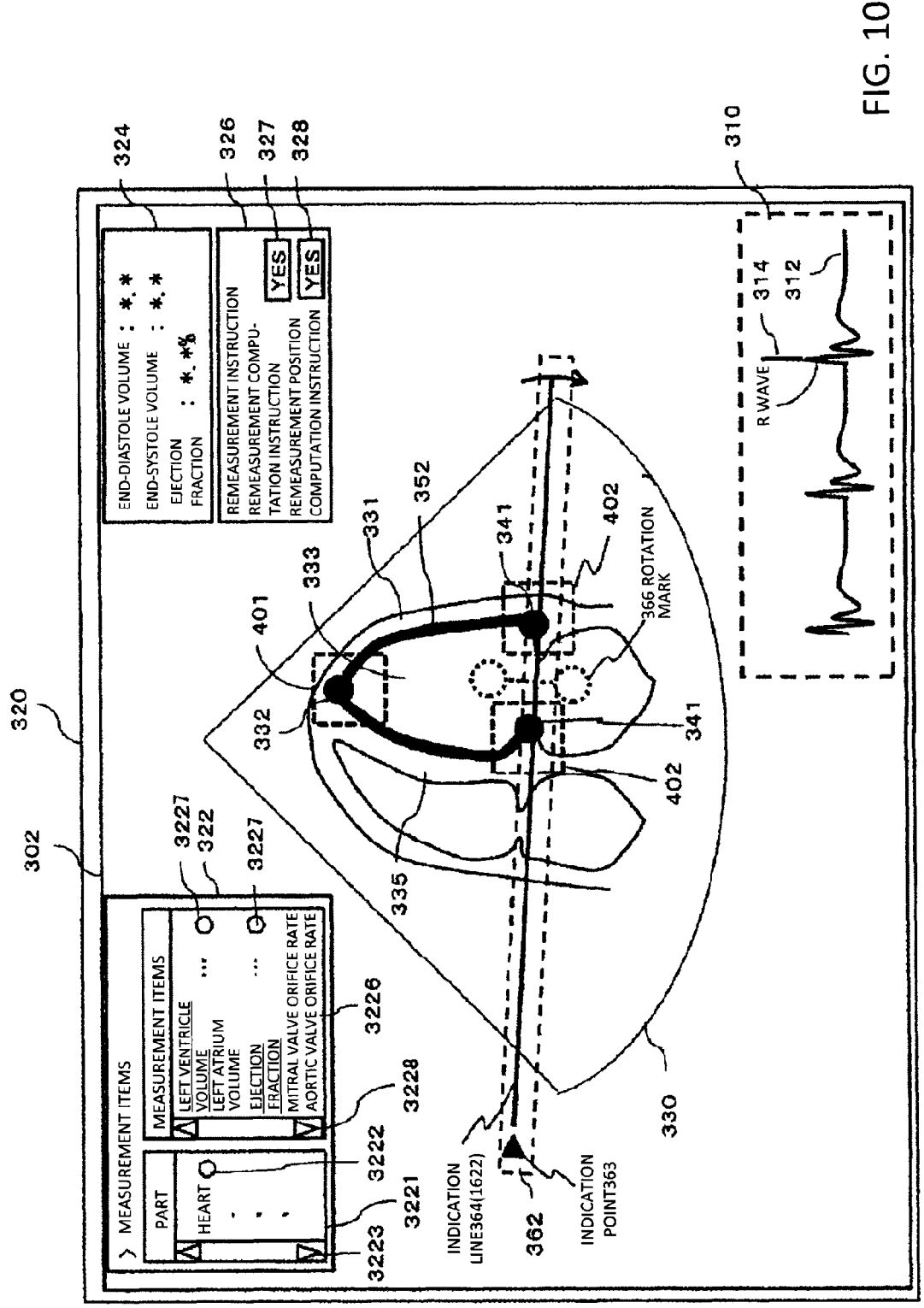
FIG. 10 is an illustrative diagram illustrating an image displayed by still another scheme different from the scheme of FIG. 3.

In step S342, a determination is made as to whether or not the already displayed position input 362 or position input 372 is selected. If a certain period of time elapses in a state where the already displayed position input 362 or position input 372 has not been selected, the execution of the control unit 170 proceeds from step S341 to step S372 as described above. If the already displayed position input 362 or position input 372 is selected, step S344 is executed. For example, as shown in FIG. 10, when the examiner places a cursor on the indication line 364 of the position input 362 to select the indication line 364, the indication line 364 can be rotated and moved. As one example, when the indication line 364 is selected, a rotation mark 366 for assisting rotation is displayed, and the whole position input 362 is rotated by rotating the rotation mark 366. In this way, the position input 362 can be rotated in step S346.

In FIG. 10, for a normal rendering method in, for example, ultrasonic examination of the heart, the two annulus portions 341 are preferably aligned horizontally with respect to the screen. However, in some cases, normal rendering of the heart cannot be performed because of a disease or body shape of the subject. Particularly, the positions of the annulus portions 341 on the respective sides may be shown in positions at heights different from each other. In this case, it is desirable that the indication line 364 indicating the position input 362 is set such that the indication line 364 is tilted corresponding to the image. The indication line 364 may be rotated using the rotation mark 366 for performing rotation operation, which is displayed when the indication line 364 is selected as described above. Alternatively, for example, by selecting the indication line 364, and operating an input mechanism with a rotating structure such as a rotary switch or a track ball provided on the operation unit 108, the indication line 364 may be tilted clockwise or counterclockwise according to the operation. Information indicating that the annulus portions 341 on the respective sides exist at different depths can be provided by tilting the indication line 364 such that it fits key tissue positions, and the auxiliary information generation unit 164 can provide more accurate measurement position candidate regions as the auxiliary information 1642 in consideration of the difference in depth direction. By this method, even if a plurality of key tissues or measurement positions are not positioned horizontally, measurement position candidate regions can be set in positions that are different in depth direction. Even if the cardiac apex portion 332 and the annulus portions 341 are different in depth direction, the measurement position candidate regions 401 and 402 can be computationally calculated.

When the position input 362 shown in FIG. 10 is selected or specified, or the indication line 364 is selected or specified in step S352, the whole position input 362 can be moved upward, downward, rightward, and leftward, and further in an oblique direction in step S354. Since the already inputted position input 362 can be finely adjusted, input of more accurate position information suited to the subject 2 is allowed. In addition, each time the position input 362 or the position input 372 shown in FIG. 9 or FIG. 10 is specified, the execution of the control unit 170 proceeds from step S279 to step S344 so that fine adjustment can be repeatedly performed. In step S372, the position input 362 or position input 372, whose position or rotation angle has been adjusted, is stored and held in the storage area 1474 of the recording unit 140.

After step S372, step S260 shown in FIG. 3 or FIG. 6 illustrated as step S374 is executed, and step S280 is executed. Descriptions of these steps are the same as those using FIG. 3 and FIG. 6, and are omitted. Although step S260 shown in FIG. 3 or FIG. 6 is executed from step S372, step S376 operates aside from step S260, and detects that a certain period of time elapses in a state where the displayed position input 362 or position input 372 have not been operated. On the basis of the detection in step S376; that is, if the certain period of time elapses in the state where there is no operation or use, the display of the target position input 362 or position input 372 is erased in step S378. A step including step S376 and step S378 may be implemented by, for example, being repeatedly executed for each certain period of time aside from the other programs. Because the display is erased after the elapse of a certain period of time, the ultrasonic image 330 is prevented from being difficult to see due to the display of the position input 362 and the position input 372.

[Method for Inputting the Position Input 362 Having the Indication Line 364 on the Center Portion of a Plurality of Key Tissues]

Figure 12:
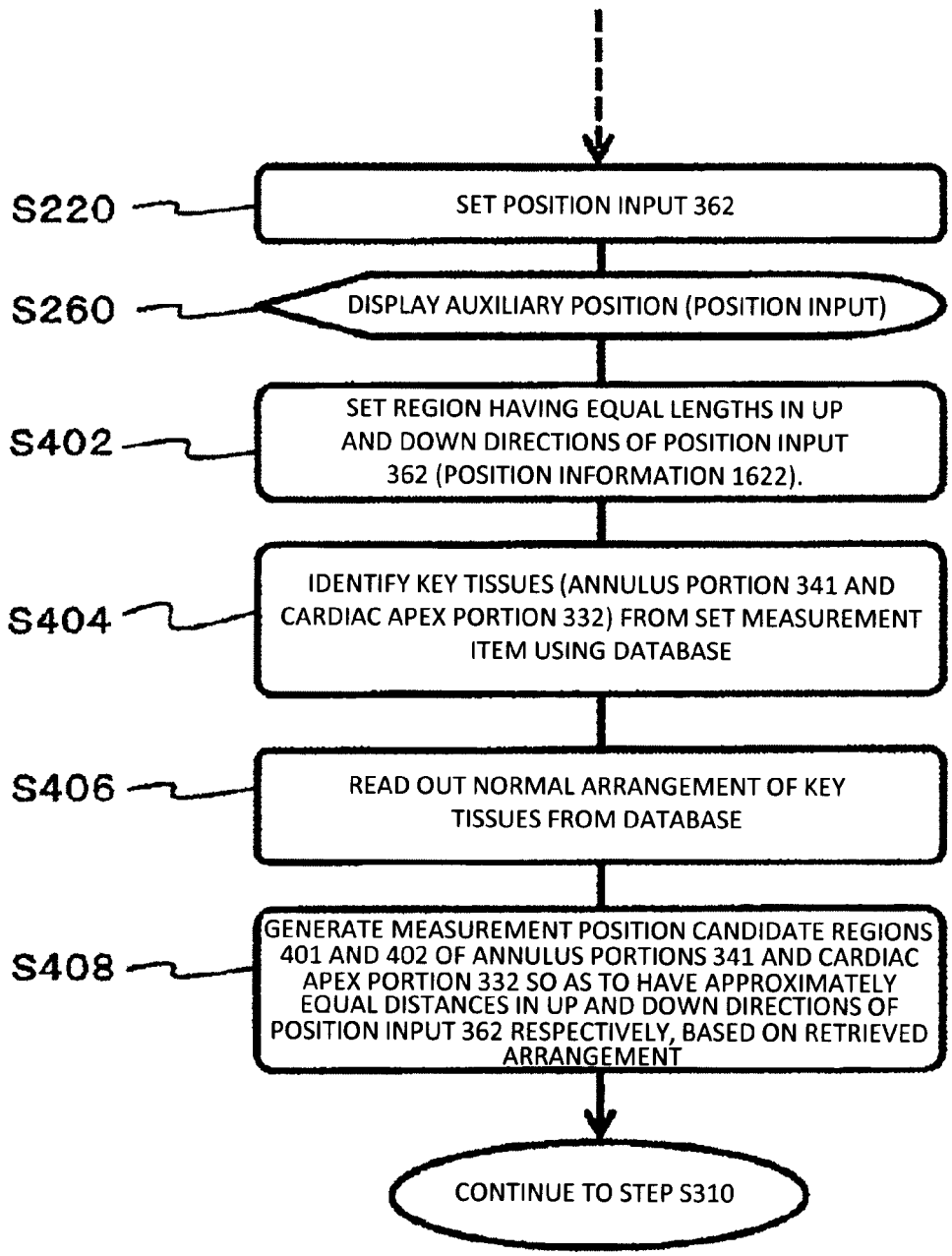
FIG. 12 is a flowchart illustrating the scheme illustrated in FIG. 11.

The examiner performs the position input 362 for measurement position computation in step S220. In a case where there are a plurality of tissues as keys for measurement, the annulus portions 341 and the cardiac apex portion 332 shown in FIG. 5, FIG. 9, or FIG. 10 become key tissues as described above in an example where the left ventricle volume of a heart is measured. By positioning the position input 362 near the center portion among the annulus portions 341 and the cardiac apex portion 332, the annulus portions 341 and the cardiac apex portion 332 which are a plurality of key tissues can be specified. FIG. 12 illustrates the flowchart for this. This is another embodiment of step S280 shown in FIG. 3 or FIG. 6. In ultrasonic examination of the heart, there may be a case where, because the annulus portion 341 or the cardiac apex portion 332 is low in image quality or moved actively due to a disease or a body shape of the subject, it is difficult to set the position input 362 directly in their positions. This case can be addressed by setting the position input 362 near the center among the annulus portions and the cardiac apex portion, which is approximately the center of the heart.

Figure 11:
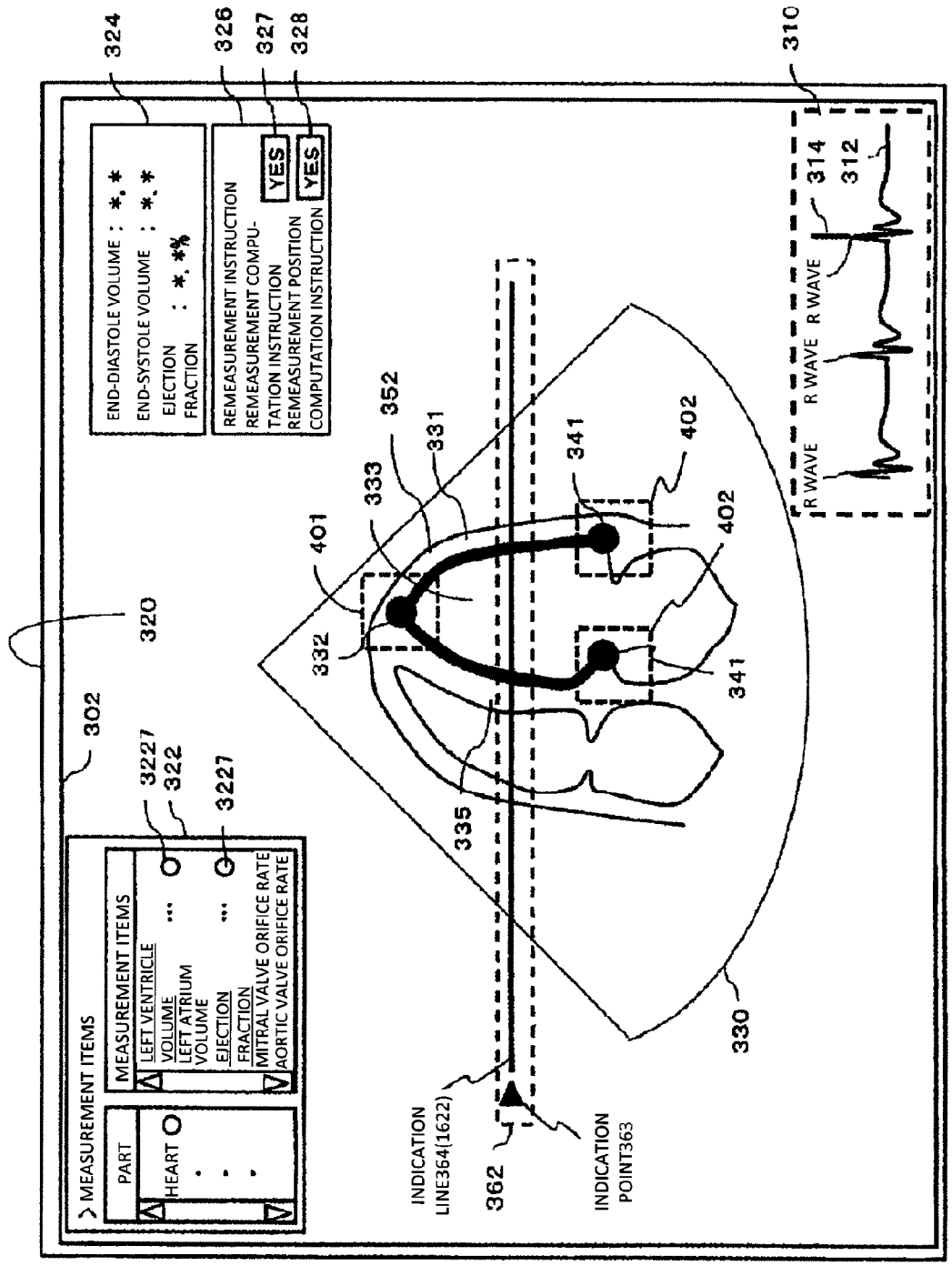
FIG. 11 is an illustrative diagram illustrating an image displayed by still another scheme different from the scheme of FIG. 3.

A description will be given by reference to FIG. 11 and the flowchart of FIG. 12. The flowchart of FIG. 12 shows a section corresponding to step S220 to step S280 of the flowchart of FIG. 3 or FIG. 6. A description of the other sections will be omitted. In step S220, the examiner inputs and sets the position input 362 such that it passes through the vicinity of an approximate center among the cardiac apex portion 332 and the annulus portions 341 as shown in FIG. 11. A state displayed in step S260 is shown as FIG. 11. However, the measurement position candidate regions 401 and 402 are processing results of step S310 and are not displayed in step S260. Step S402 to step S408 are steps corresponding to step S280 of FIG. 3 or FIG. 6. In step S402, a region having approximately equal lengths in the up and down directions of the position input 362 is set. Further, in step S404, the database is searched using a set measurement item "measurement of left ventricle volume" to identify that key tissues are the annulus portions 341 and the cardiac apex portion 332. Further, the database is searched for an arrangement relationship of key tissues. The positions of the annulus portions 341 and the cardiac apex portion 332 are predicted so as to have approximately equal distances in the up and down directions of the position input 362 respectively in the arrangement relationship retrieved in step S408, and the measurement position candidate regions 402 of the annulus portions 341 and the measurement position candidate region 401 of the cardiac apex portion 332 are identified and set. In this way, by inputting one position input 362, a plurality of measurement position candidate regions corresponding to a plurality of key tissues can be set. There are effects that the reliability of measurement accuracy can be improved, and the complexity of the examiner's operation can be reduced.

[Method for Inputting a Position Input 450 at the Center Portion of a Heart which is a Part]

Figure 13:
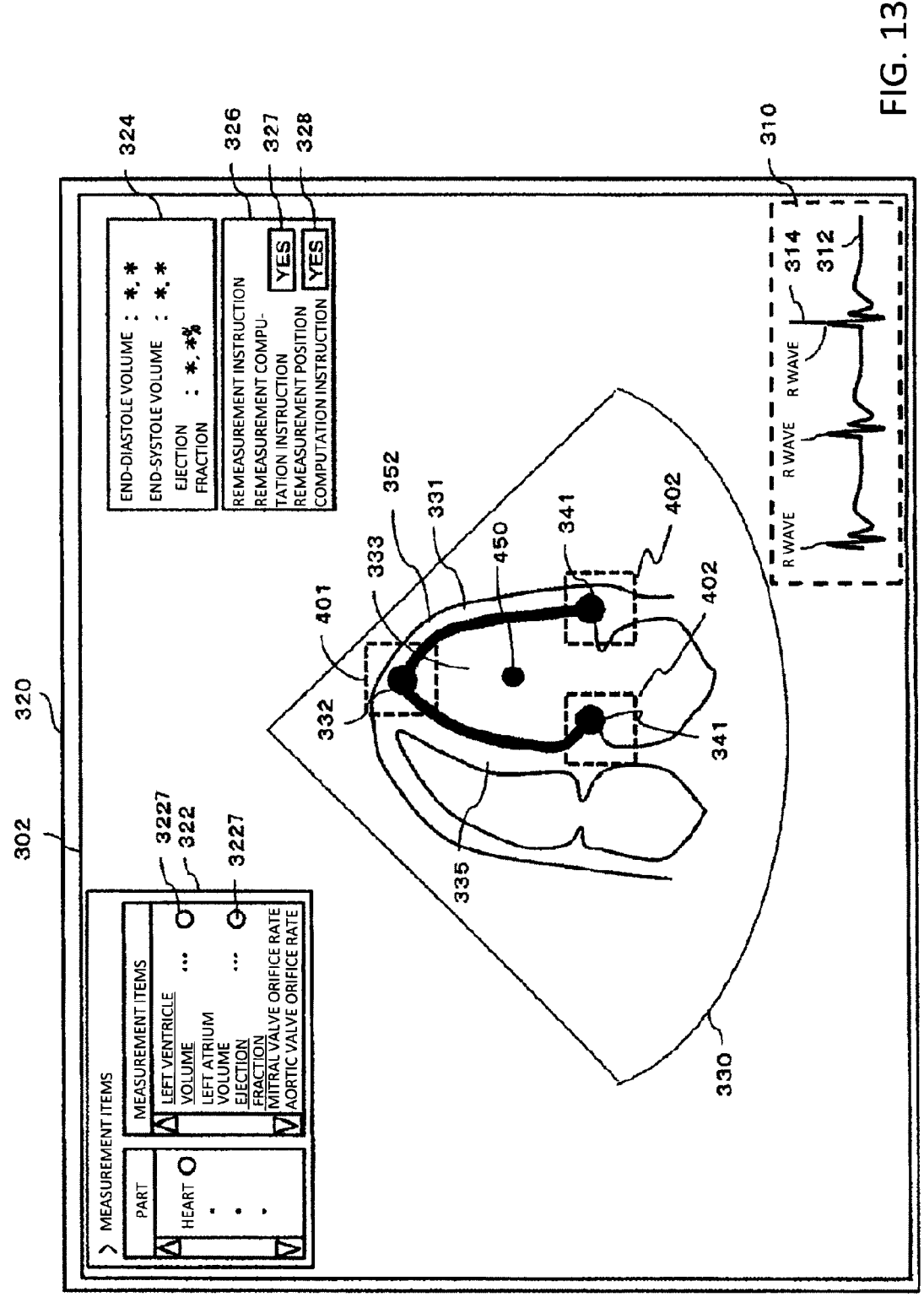
FIG. 13 is an illustrative diagram illustrating an image displayed by still another scheme different from the scheme of FIG. 3.
Figure 14:
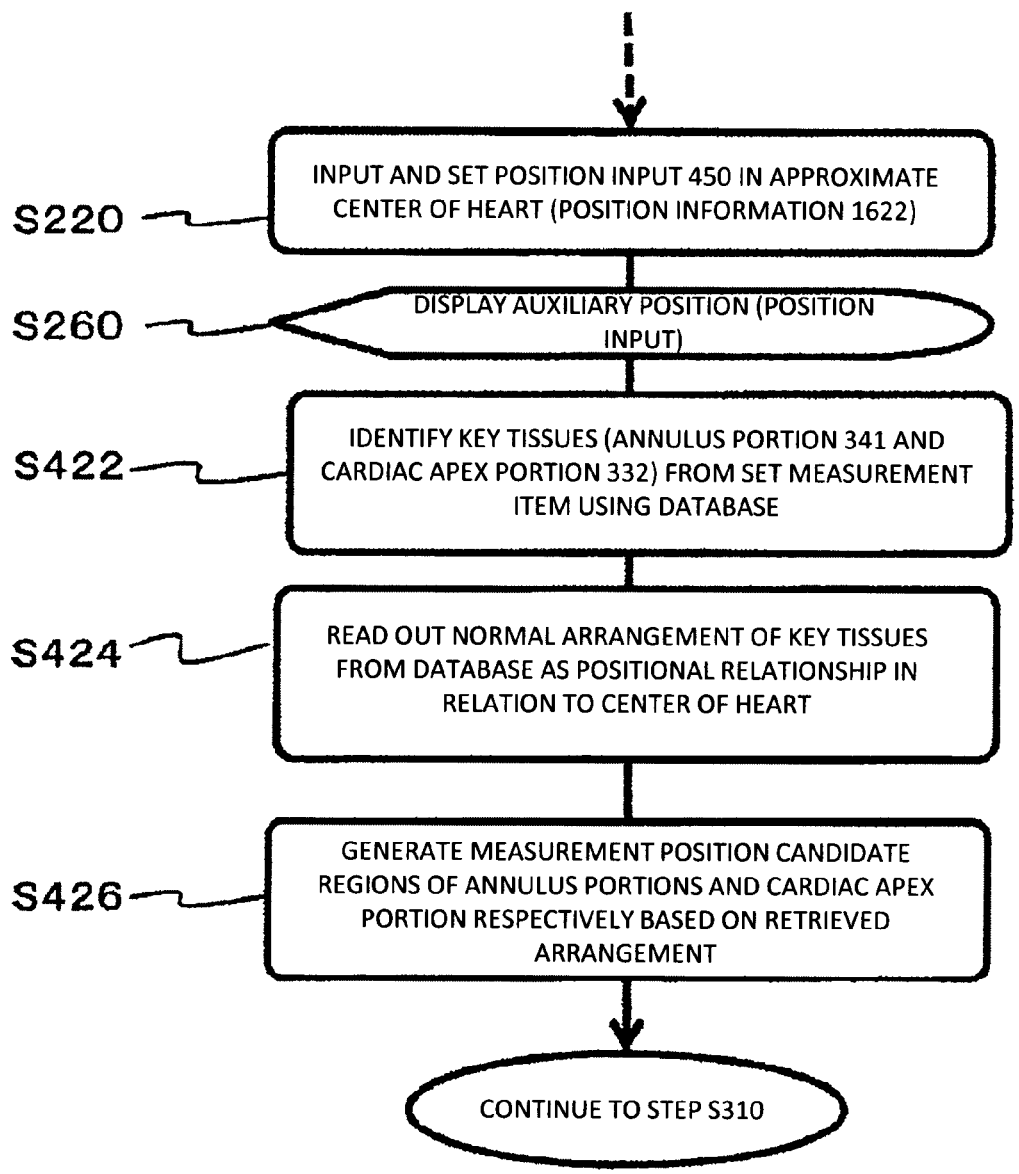
FIG. 14 is a flowchart illustrating the scheme illustrated in FIG. 13.

In the embodiment illustrated in FIG. 11, the method has been described which positions can be used for the position input 362 having the indication line 364 near the center among the annulus portions 341 and the cardiac apex portion 332 which are a plurality of key tissues. However, instead of positioning the position input 362 having the indication line 364 with respect to the annulus portions 341 and the cardiac apex portion 332 which are a plurality of key tissues, a point may be inputted as the position input. A description will be given using an image displayed on the display unit 132 shown in FIG. 13 and a flowchart shown in FIG. 14. The flowchart shown in FIG. 14 illustrates a section corresponding to step S220 to step S280 of the flowchart of FIG. 3 or FIG. 6 as in the description using FIG. 12. A description of the other sections will be omitted.

In step S220 of FIG. 14, the examiner inputs the position input 450, for example, having a dot shape that indicates an approximate center portion of the heart 331, near the approximate center of the heart 331 which is a part. In step S260, the position input 450 is displayed as an image superimposed on the ultrasonic image 330 on the display screen 320 of the display unit 132 as shown in FIG. 13. However, the measurement position candidate regions 401 and 402 have not yet been displayed in step S260.

Next, in step S422, on the basis of a set measurement item which is a measurement condition, the annulus portions 341 and the cardiac apex portion 332 are identified as key tissues by computation processing such as database search. In step S424, a positional relationship of the annulus portions 341 and the cardiac apex portion 332 in relation to the center portion of the heart 331 indicated by the inputted position input 450 is identified by the information retrieved from the database. In step S426, estimated positions of the annulus portions 341 and the cardiac apex portion 332 in a state where the center portion of the heart 331 is specified by the position input 450 are computationally calculated to calculate the measurement position candidate regions 402 for the annulus portions 341 and the measurement position candidate region 401 for the cardiac apex portion 332. The calculated measurement position candidate region 401 and measurement position candidate regions 402 are shown by dashed lines in FIG. 13.

In the scheme illustrated in FIG. 13 and FIG. 14, since the position input 450 is assumed to be the approximately central position of the heart 331, position information in the depth direction and position information in the horizontal direction are given, and on the basis of these, the measurement position candidate region 401 and the measurement position candidate regions 402 are computed. Therefore, measurement position candidate regions can be computed more accurately, and the reliability of measurement processing is improved.

Next, an embodiment will be described by reference to FIG. 15 and FIG. 16 in which the central portion of the heart 331 which is a part is specified in step S220 as in the scheme described by reference to FIG. 13 and FIG. 14, but the measurement position candidate region 401 and the measurement position candidate regions 402 are computed from the specified position input 450 by a slightly different method. The same reference numerals refer to components or steps having the same functions. A description of them will be omitted.

Figure 15:
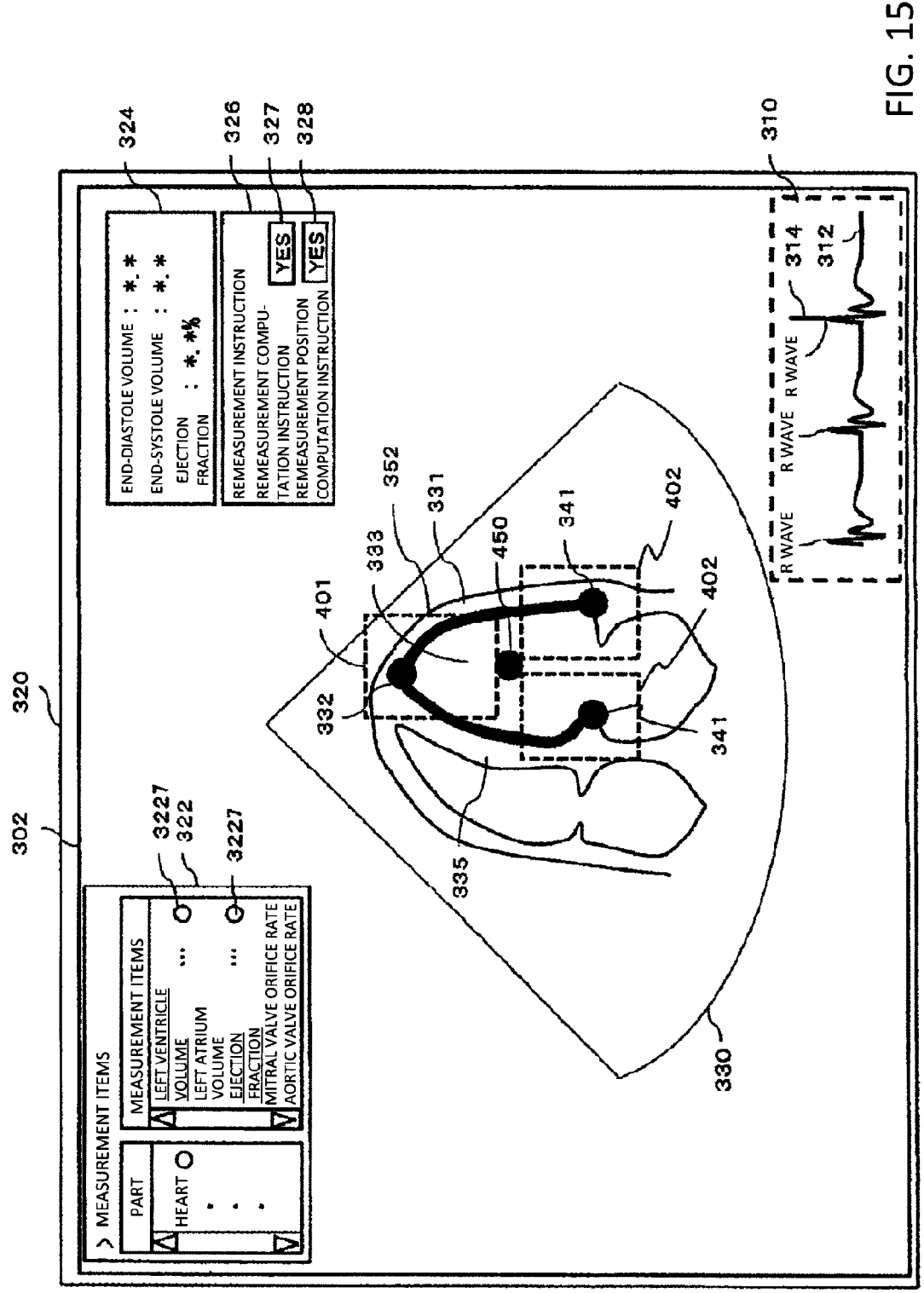
FIG. 15 is an illustrative diagram illustrating an image displayed by still another scheme different from the scheme of FIG. 3.
Figure 16:
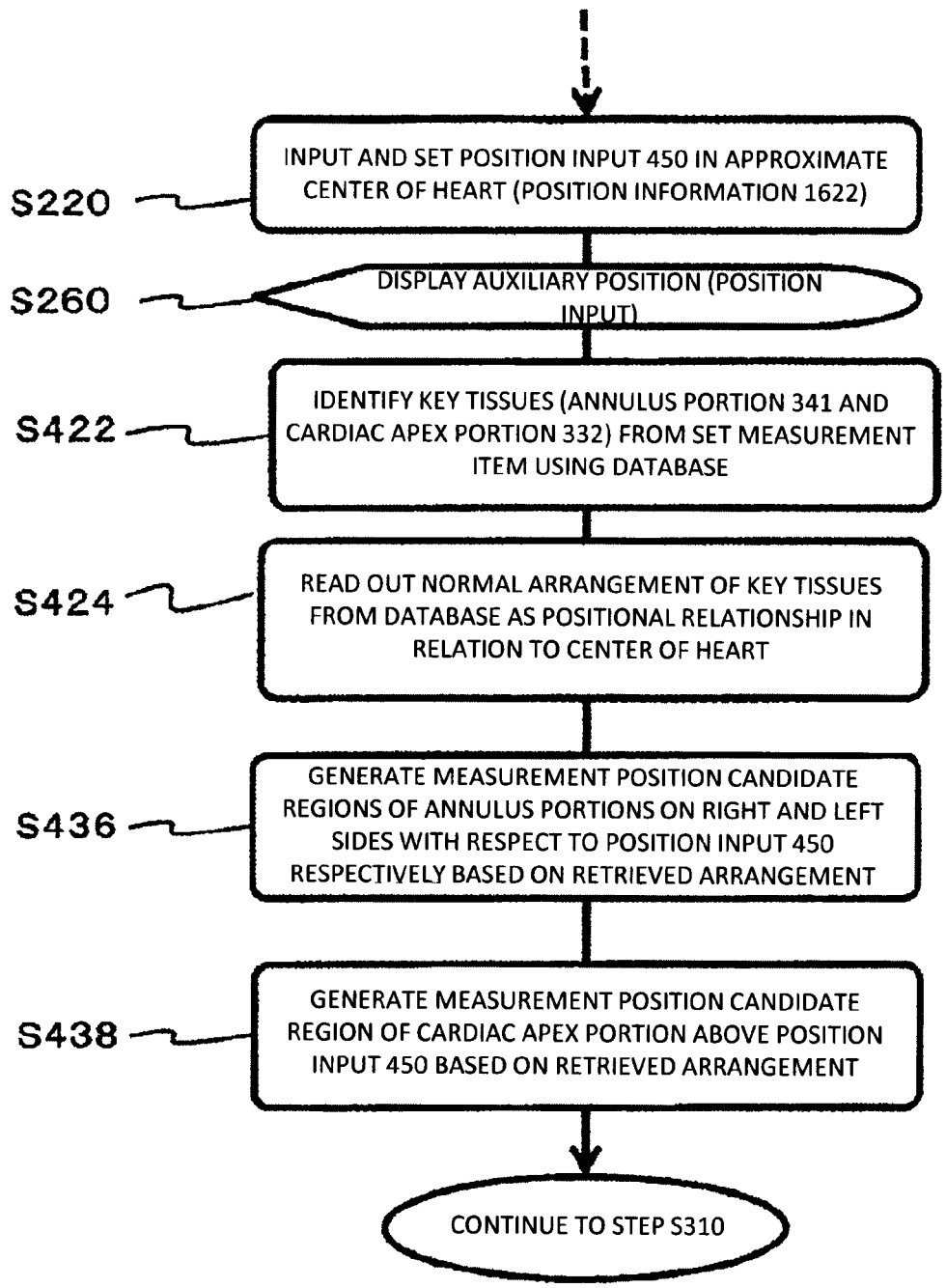
FIG. 16 is a flowchart illustrating the scheme illustrated in FIG. 15.

In step S220, as with FIG. 14, the examiner inputs the position input 450 that indicates an approximate center portion of the heart 331, near the approximate center of the heart 331 which is a part, and in step S260, the ultrasonic image 330 having the position input 450 superimposed thereon is displayed in FIG. 15. However, the measurement position candidate regions 401 and 402 have not yet been displayed in step S260. In step S422, on the basis of a set measurement item which is a measurement condition, the annulus portions 341 and the cardiac apex portion 332 are identified as key tissues by computation processing such as database search. In step S424, positional relationships of the annulus portions 341 and the cardiac apex portion 332 in relation to the center portion of the heart 331 indicated by the inputted position input 450 are identified by the information retrieved from the database.

In step S436 and step S438, computation processing slightly different from step that of S426 of FIG. 14 is performed by the auxiliary information generation unit 164. In step S436, it is determine that the annulus portions 341 exists on both right and left sides with respect to the position input 450, on the basis of the positional relationship of the search result in step S424 and the central portion of the heart 331, and accordingly the measurement position candidate regions 402 are set on both the right and left sides with respect to the inputted position input 450.

Further, in step S438, it is determined that the cardiac apex portion 332 exists above the inputted position input 450, on the basis of the positional relationship of the search result in step S424 and the central portion of the heart 331, and the measurement position candidate region 401 is set accordingly. The measurement position candidate regions 402 set in step S436 and the measurement position candidate region 401 set in step S438 are shown by dashed lines in FIG. 15. The scheme described by reference to FIG. 15 and FIG. 16 can limit the position of a measurement position candidate region by position information indicated by the position input 450 inputted by the examiner, and therefore can set the measurement position candidate region more accurately.

A further scheme will be described by reference to FIG. 17 and FIG. 18. This scheme is a scheme very close to the scheme described by reference to FIG. 15 and FIG. 16. Also, this scheme is close to the method illustrated in FIG. 7 in which the position input 362 is set in the upward, downward, leftward, and rightward directions of the indication point 363 if the indication point 363 is inside a key tissue.

Figure 18:
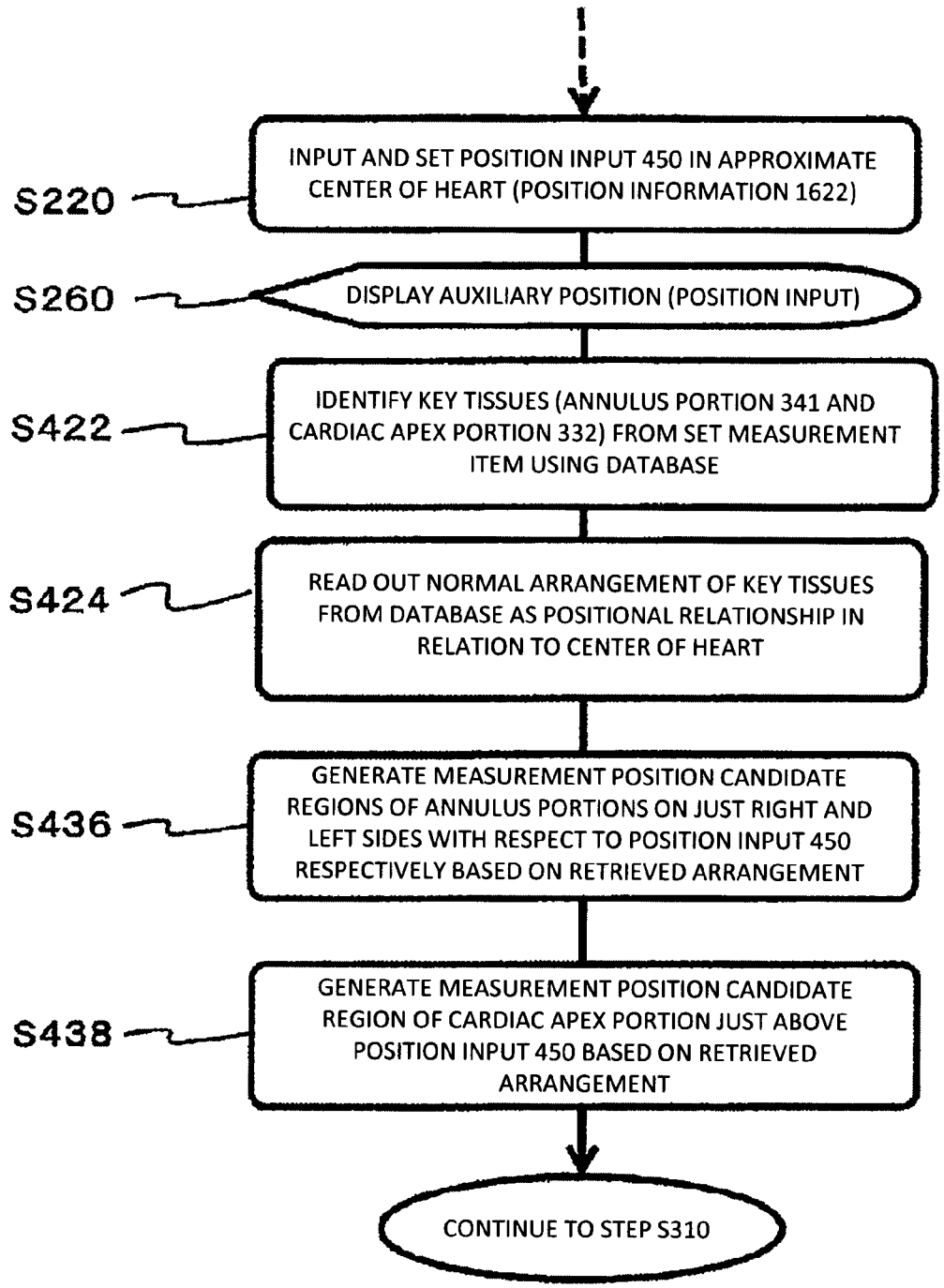
FIG. 18 is a flowchart illustrating the scheme illustrated in FIG. 17.

In step S220 of FIG. 18, the examiner sets the position input 450 between the annulus portions 341 which are key tissues. Step S260, step S422, and step S424 processed by the auxiliary information generation unit 164 are the same as the previously described processing operations shown in FIG. 16 and FIG. 14, and a description thereof will be omitted.

In step S436, assuming that the annulus portions 341 on the respective sides are just beside the position input 450, measurement position candidate regions are set on both sides of and just beside the position input 450. In other words, the measurement position candidate region 402 for the left annulus portions 341 is set approximately just to the left of the position input 450, and the measurement position candidate region 402 for the left annulus portions 341 is set approximately just to the right of the position input 450. Further, in step S438, it is determined that the cardiac apex portion 332 exists just above the position input 450, and the measurement position candidate region 401 for the cardiac apex portion 332 is set just above the position input 450.

Figure 17:
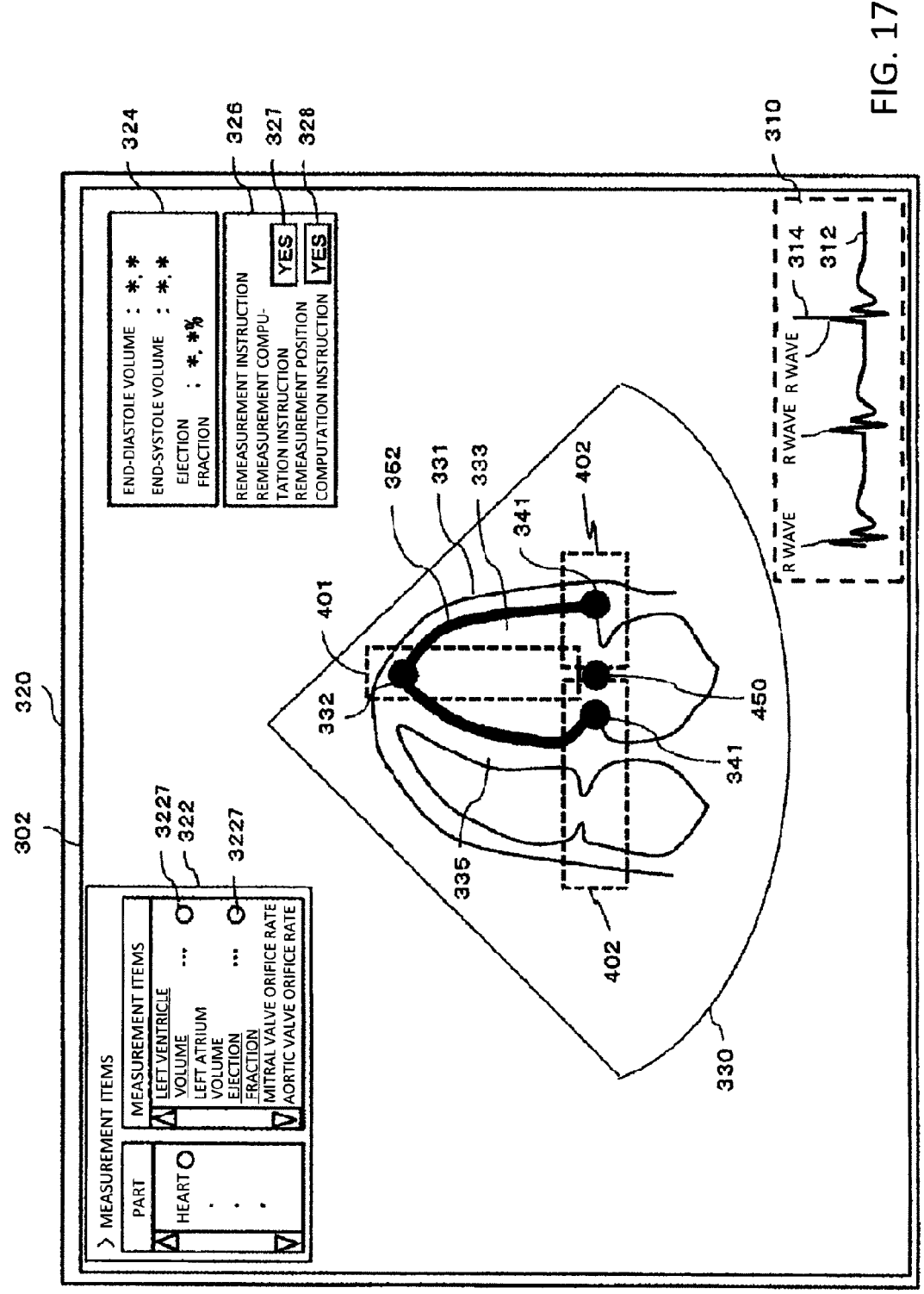
FIG. 17 is an illustrative diagram illustrating an image displayed by still another scheme different from the scheme of FIG. 3.

The scheme illustrated in FIG. 17 and FIG. 18 has an effect that in a case where the measurement position candidate region 402 for the annulus portion 341 is set, the width in the height direction of the measurement position candidate regions 402 can be narrowed, and therefore the accuracy and the reliability of computation of the measurement position computation unit B 114 are improved. Further, in a case where the measurement position candidate region 401 for the cardiac apex portion 332 is set, the width in the horizontal direction of the measurement position candidate region 401 can be narrowed, and therefore the accuracy and the reliability of computation of the measurement position computation unit B 114 are improved as well. Finally, as a result, the accuracy and the reliability of measurement positions are improved, and the accuracy and the reliability of computed measurement values are improved.

[Detailed Description of Step S220]

Details of step S220 illustrated in FIG. 12, FIG. 14, FIG. 16, and FIG. 18 will be described below by reference to a flowchart of FIG. 19. Operation of FIG. 19 is very similar to that of the method described by reference to FIG. 7 and FIG. 8, and the operation of FIG. 19 described below may be applied to the method of FIG. 7 and FIG. 8, and conversely the method of FIG. 7 and FIG. 8 may be applied to the method of FIG. 19.

Figure 19:
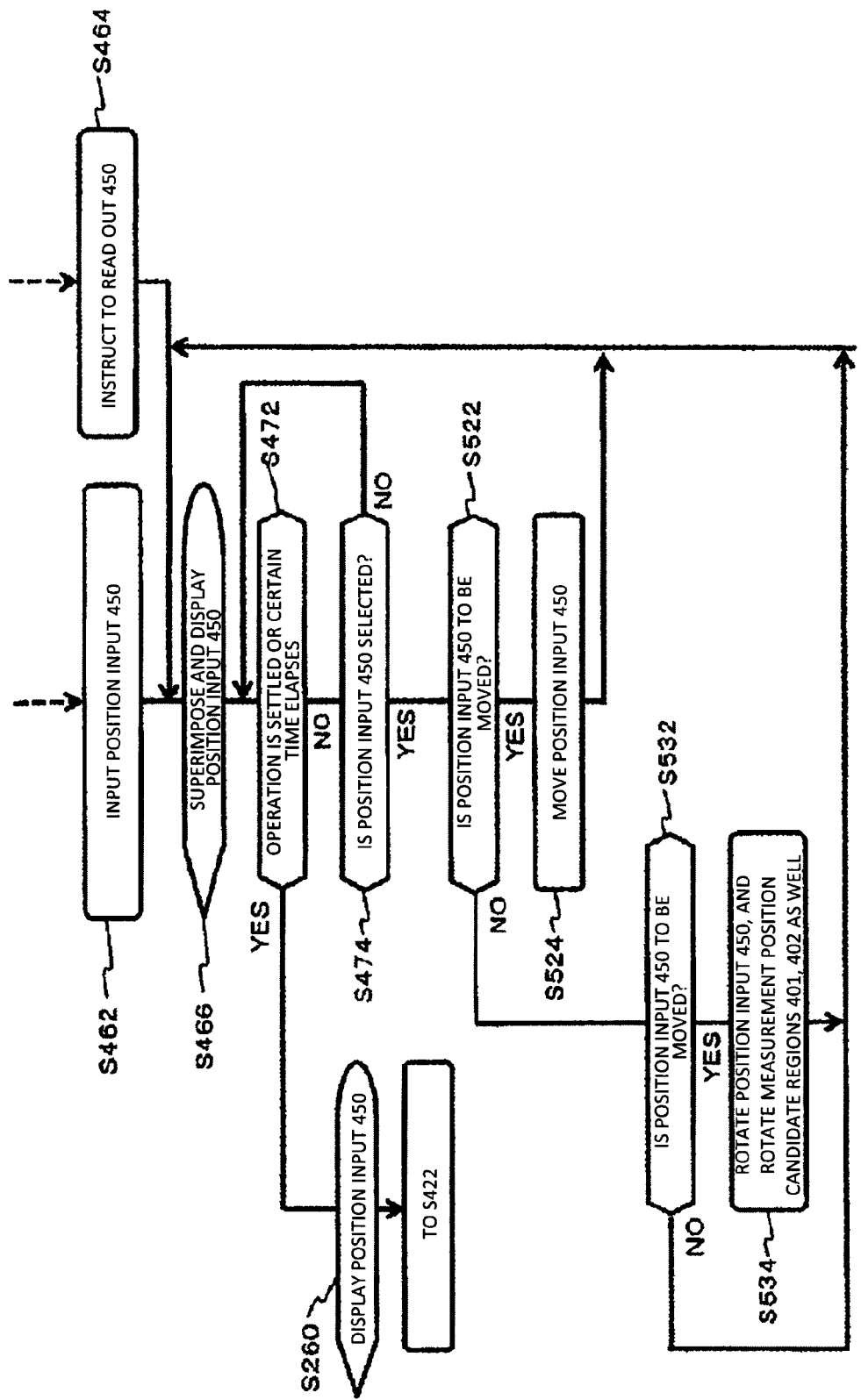
FIG. 19 is a flowchart illustrating a detailed processing operation of step S220.

In step S462 of FIG. 19, when the position input 450 is inputted by the examiner, the position input 450 inputted in step S466 is superimposed and displayed on the ultrasonic image 330. In step S462, if the examiner wants not only to input the position input 450, but also to use or display the position input 450 used before; for example, the examiner wants to read out and display again the position input 450 inputted for obtaining a measurement value displayed as the measurement values 324 on the image 302, and modify the position of the displayed position input 450 to recompute the measurement value, the examiner can read out the position input 450 inputted in the past by performing readout operation. For example, if "end-diastole volume" displayed as the measurement values 324 is selected, the position input 450 used at this time can be read out in step S464 and displayed in step S466. The operation of reading out and displaying the position input 450 used in the past in this way can be, of course, applied also to the flowchart shown in FIG. 3.

In step S472, a determination is made as to whether to settle the displayed position input 450 or further modify its display position and the like. If the examiner performs operation for settlement, the position input 450 becomes in a set state, and is displayed in step S260 as already described, and the execution of the control unit 170 proceeds to the already described step S422. Further, even if the examiner does not perform operation for settlement particularly, the set state occurs after the elapse of a certain period of time, and then step S260 and step S422 are executed. These processing contents have been previously described, and a description thereof will be omitted here.

If setting is not made in step S472, the execution of the control unit 170 proceeds to step S474, and determines whether or not the position input 450 is selected. If the position input 450 is not selected, the execution returns to step S472, and it is determined that whether the certain period of time elapses and whether the settlement operation is performed, and if the condition is satisfied, the set state occurs since the position input 450 is settled as described above, and the execution of the control unit 170 proceeds to step S260. If the position input 450 is selected, a determination is made in step S522 as to whether the position is moved, and if the position input 450 is to be moved, the position of the position input 450 is moved on the basis of operation in step S524. If the position input 450 is not to be moved, the execution of the control unit 170 proceeds from step S522 to step S532, and it is determined whether there is an instruction for rotation. In the case of a rotation instruction, input of rotation operation is performed in step S534. When the operation for rotation is performed in step S534, measurement position candidate regions such as the measurement position candidate region 401 and the measurement position candidate regions 402 illustrated in FIG. 13, FIG. 15, or FIG. 17 can be rotated with respect to the position input 450.

Further, if there is no rotation operation in step S532, the execution of processing returns again to step S466 assuming that the position input 450 is in a selected state but in the process of operation. Also, after the operation of step S524 or step S534 is performed, the execution of processing again returns to step S466, and display based on the operation is performed. In the processing operation described by reference to the flowchart shown in FIG. 19, since the position input 450 inputted once or the position input 450 inputted in the past can be finely adjusted and used again, the position input 450 can be more accurately set with respect to an image of the ultrasonic image 330 in which input is difficult.

[Description of Another Embodiment for Setting of a Position Input 410 and Setting of a Measurement Position Candidate Region]

Figure 20:
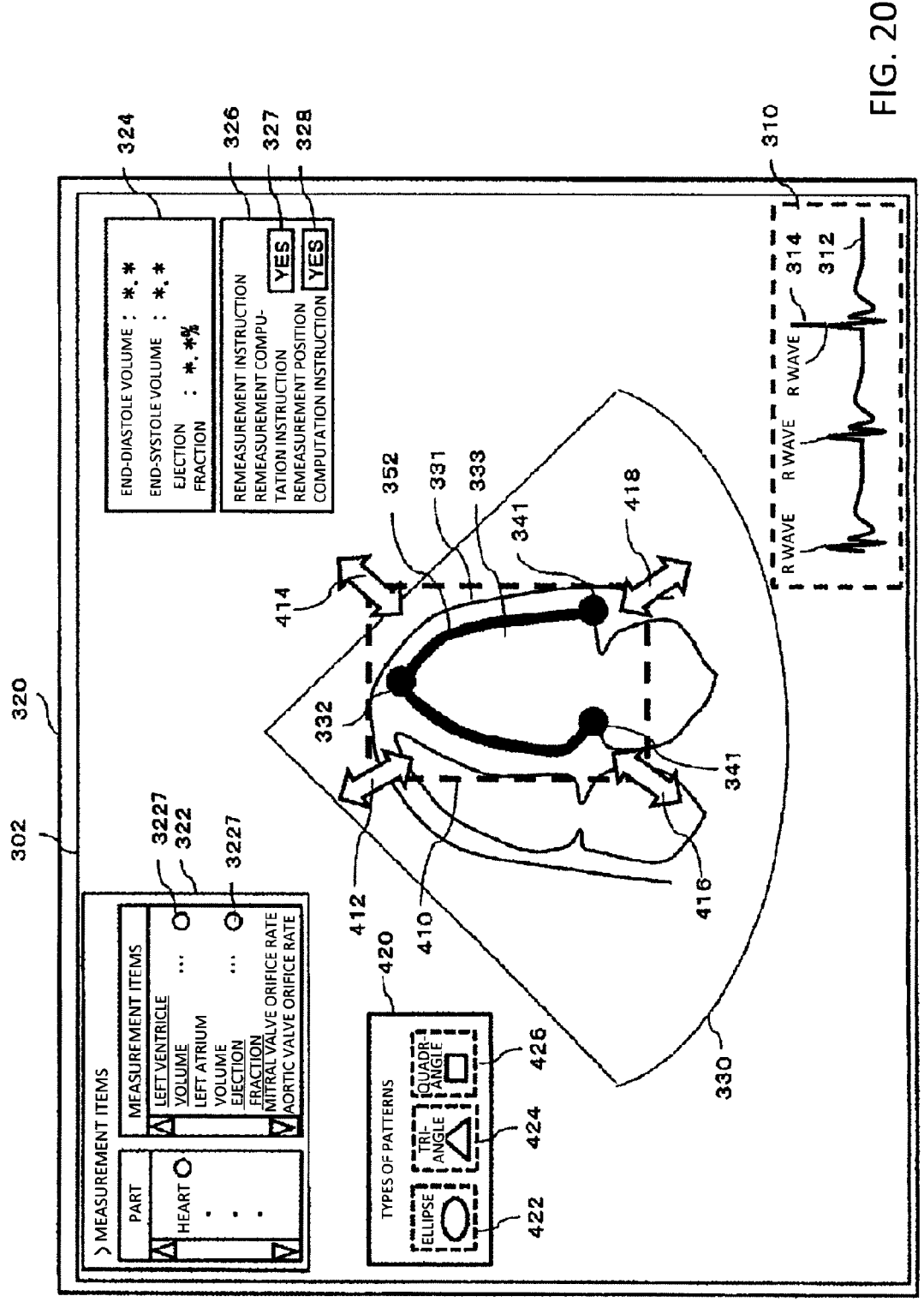
FIG. 20 is an illustrative diagram illustrating an image displayed by still another scheme different from the scheme of FIG. 3.
Figure 21:
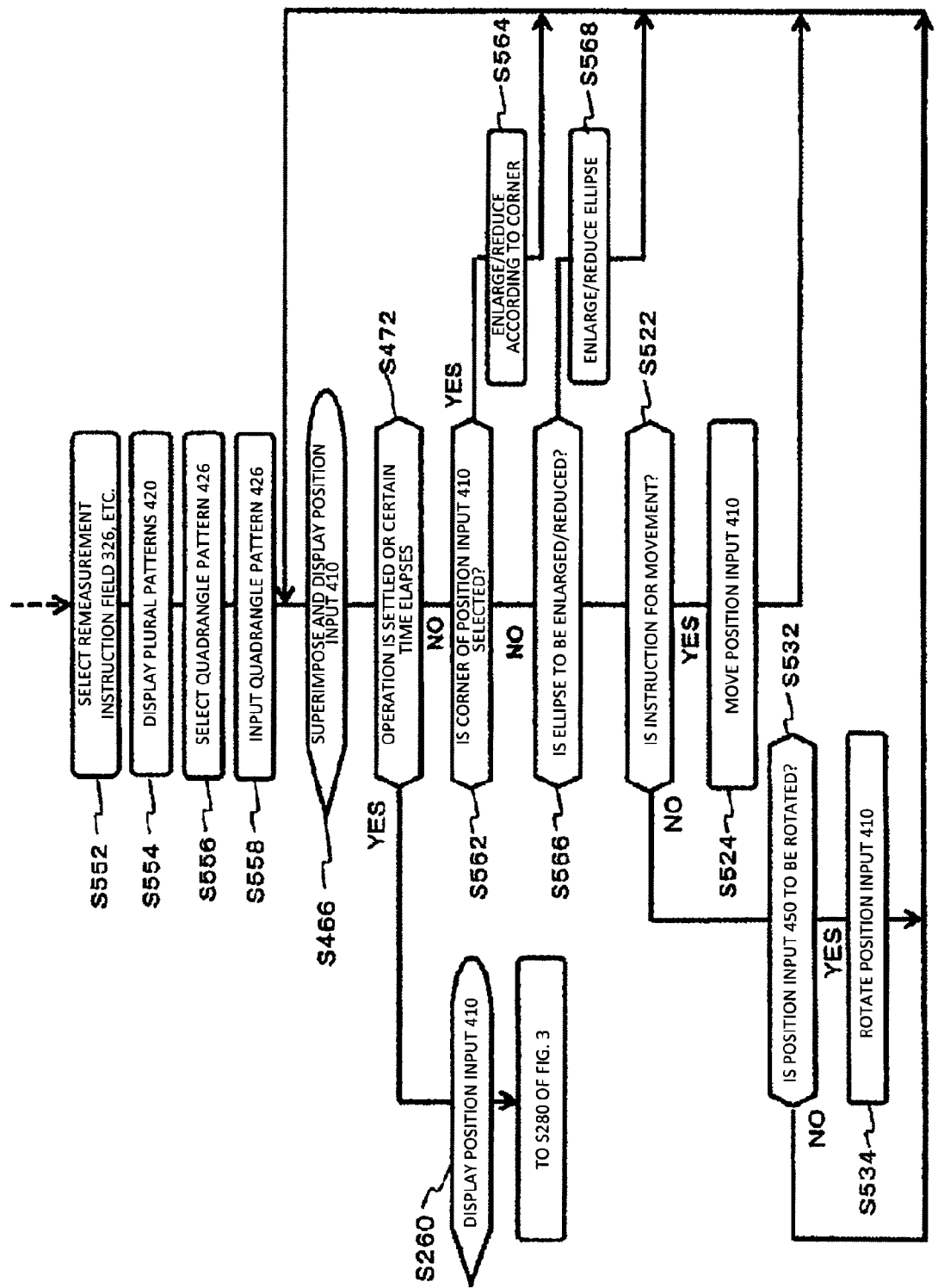
FIG. 21 is a flowchart illustrating the scheme illustrated in FIG. 20.

Next, another embodiment of the position input 410 will be described by reference to FIG. 20 and FIG. 21. The basic operation of the flowchart shown in FIG. 21 is similar to that of the flowchart shown in FIG. 19. Steps given the same reference numerals as in the flowchart of FIG. 19 perform the same processes, and a description thereof will be omitted. In the flowchart shown in FIG. 3, when the examiner determines that a measurement position, a measurement position candidate region, and a measurement value which are displayed in step S164 are not proper, the position input 450 is inputted in step S462 of FIG. 19. In the flowchart shown in FIG. 21 as described below, instead of the position input 450, a pattern, for example, a quadrangle 426 is selected from a plurality of patterns 420 and inputted as the position input 410. A specific description will be given below by reference to the flowchart shown in FIG. 21.

When the remeasurement instruction field 326 is selected in step S552, it means that the examiner determines improperness in step S210 of FIG. 3, and step S554 is executed as a detailed procedure in step S220. In step S554, the plurality of patterns 420 are superimposed and displayed on the image 302. The plurality of patterns 420 include patterns, such as an ellipse pattern 422 and a triangle pattern 424, from which a proper pattern can be selected. In the following description, it is assumed that the quadrangle pattern 426 as an example is selected in step S556. In step S558, the selected quadrangle pattern 426 is inputted. In step S466, the inputted pattern is superimposed and displayed on the ultrasonic image 330. FIG. 20 shows a state where the quadrangle pattern 426 is inputted, and the position input 410 is a pattern inputted on the basis of the quadrangle pattern 426.

As described by reference to FIG. 21, if it is determined that setting is made in step S472, the execution of the control unit 170 proceeds to step S260, and the set state is displayed as the image 302. Subsequently, step S280 of FIG. 3 is executed. On the other hand, if the inputted quadrangle pattern 426 is not settled and is to be further modified, the execution of the control unit 170 proceeds from step S472 to step S562. For example, in the case where the triangle pattern 424 or the quadrangle pattern 426 is selected in step S556, the pattern inputted by selecting a corner in step S562 can be enlarged and reduced. It is determined whether or not a corner is selected in step S562, and if the corner is selected, the inputted pattern is enlarged or reduced on the basis of movement of the selected corner in step S564. As shown in FIG. 20, by moving each corner of the position input 410 along respective moving directions 412, 414, 416, 418, the position input 410 can be enlarged or reduced.

In step S564, the size of the position input 410 is adjusted to a size within which the right and left annulus portions 341 and the cardiac apex portion 332 which become key tissues in measurement items are assumed to be put. The above-described quadrangle can be moved using, for example, a pointing device of the operation unit 108. Its result is displayed as the image 302 in step S466. If the ellipse pattern 422 is selected in step S556, and it is determined in step S566 whether or not to perform enlargement or reduction of the selected ellipse pattern 422, and if enlargement or reduction is to be performed, the enlargement or reduction of the displayed ellipse pattern 422 is performed in a specified direction in step S568. Its result is displayed as the image 302 in step S466.

Further, by step S522 and step S524, a displayed pattern itself can be moved. Details of the operations of these steps have already been described by reference to FIG. 19. Further, by step S532 and step S534, the angle of a displayed pattern itself can be changed. If positions of the right and left annulus portions 341 are different in not the horizontal but the vertical direction with respect to the display screen 320, the position input 410 which is a displayed pattern can be rotated in step S534 so that the angle of the displayed pattern matches the tilt of the right and left annulus portions 341. Accordingly, there is an effect that tissues in various states, such as a part different from that of a healthy person, can be handled.

The inputted position input 410 becomes in a state where a key tissue is placed within the position input 410, by adjustment such as enlargement or reduction of its area. Therefore, as a measurement position candidate region which is obtained by processing of generating the auxiliary information 1642 by the auxiliary information generation unit 164 in step S280 of FIG. 3, a pattern set in FIG. 21 can be used. For example, within the area of a quadrangle indicated by the position input 410 shown in FIG. 20, there are the right and left annulus portions 341 and further the cardiac apex portion 332. Therefore, the measurement position computation unit B 114 can search an area defined by setting of the position input 410 to detect the right and left annulus portions 341 and the cardiac apex portion 332 which are key tissues. In this way, a pattern having an appropriate shape is selected in step S56, the size of the selected pattern is adjusted, an angle is further adjusted, and the area indicated by the obtained pattern is used as a measurement position candidate region, so that processing of the auxiliary information generation unit 164 is simplified, and input operation of the position input 410 is also simplified, and therefore this method is very effective.

[Description of a Further Embodiment for Setting of a Measurement Position Candidate Region]

Figure 22:
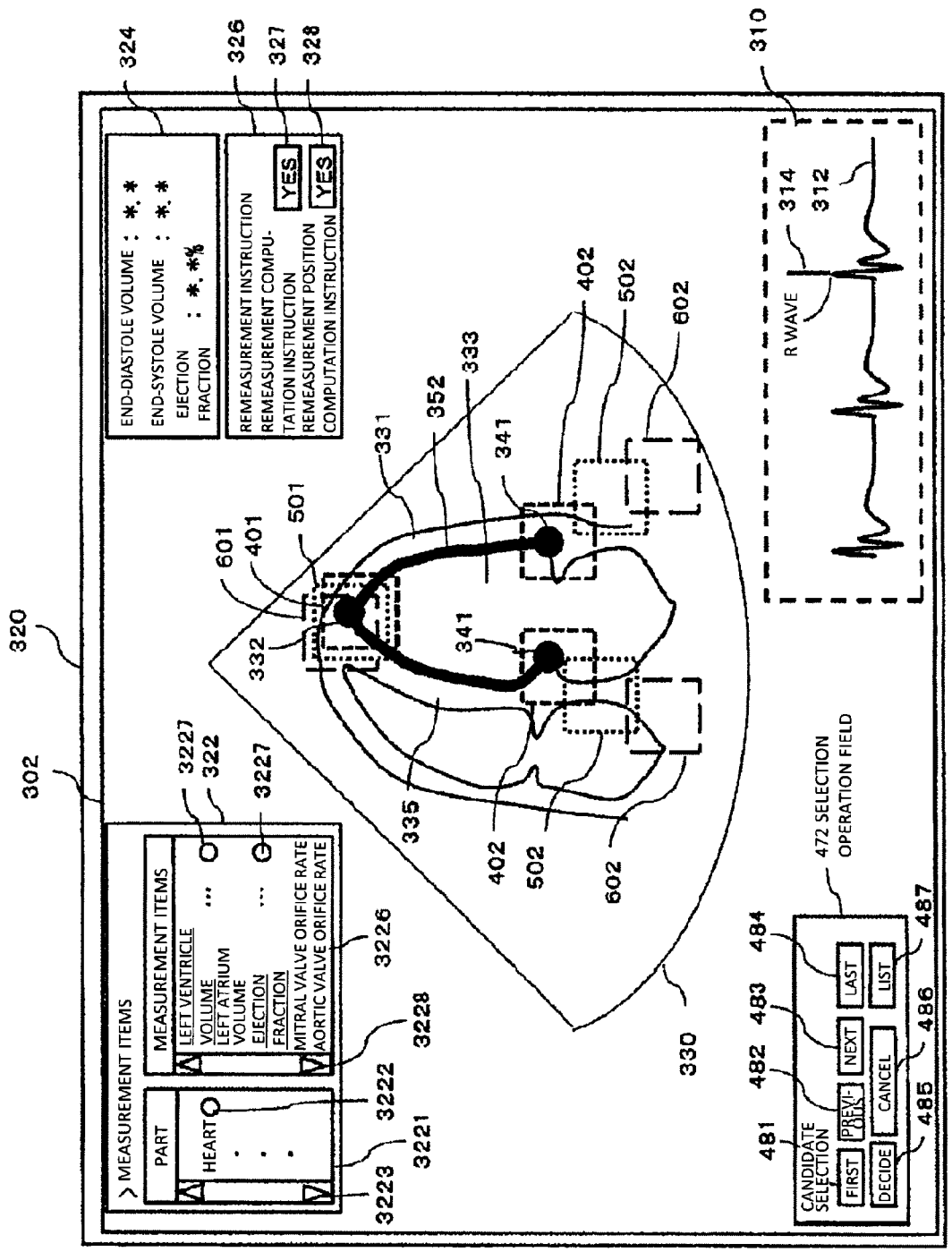
FIG. 22 is an illustrative diagram illustrating an image displayed by still another scheme different from the scheme of FIG. 3.
Figure 23:
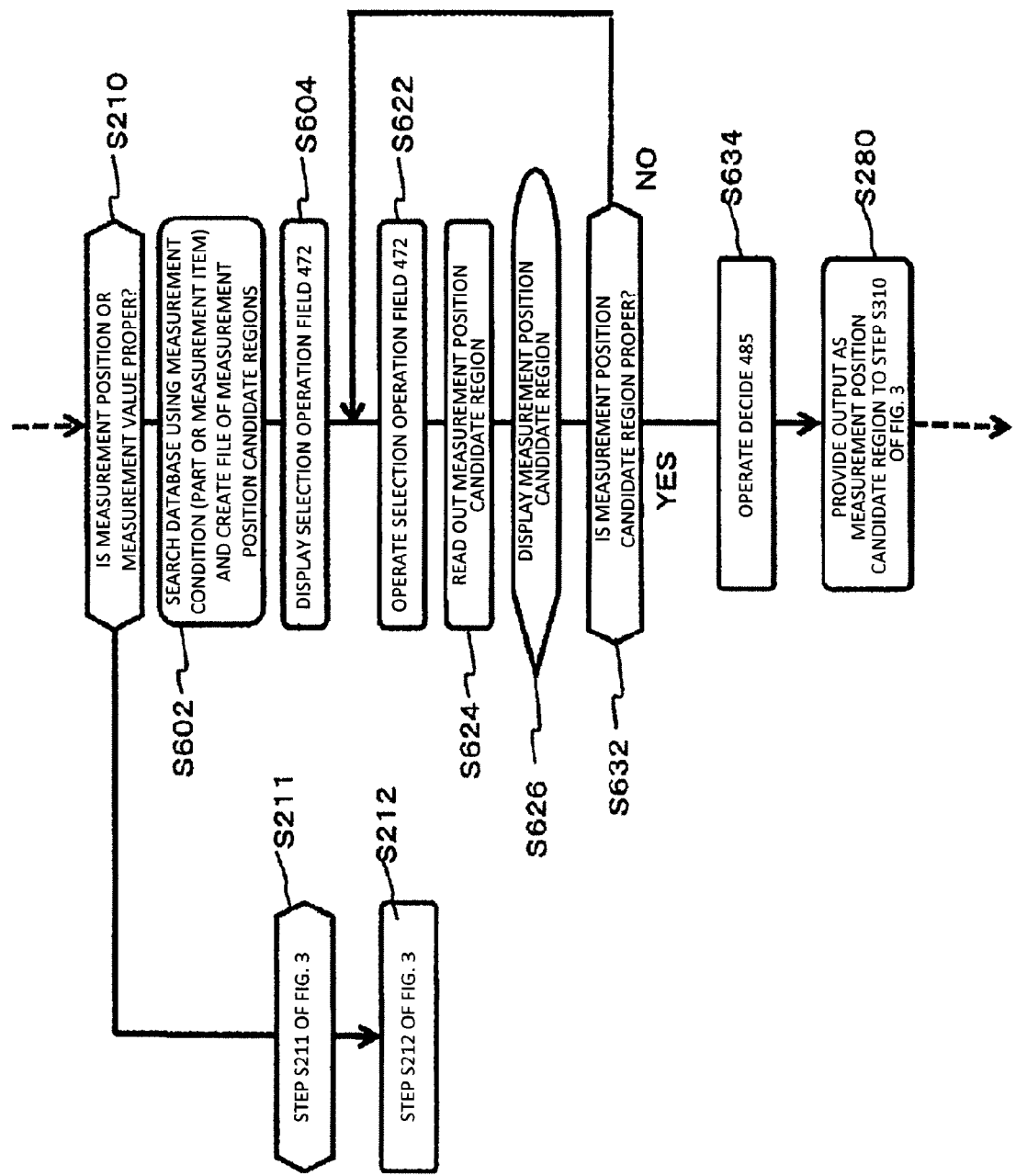
FIG. 23 is a flowchart illustrating the scheme illustrated in FIG. 22.

A further embodiment will be described by reference to FIG. 22 and FIG. 23. In this embodiment, after a part or a measurement item is set using the part display field 3221 or the measurement item display field 3226 of the measurement items 322 of FIG. 22, the database of the recording unit 140 which stores measurement position candidate regions is searched using such information so that data about corresponding measurement position candidate regions can be extracted and its file can be created. Using the file by the examiner, a measurement position candidate region can be easily set.

Step S210 of FIG. 23 has already been described by reference to FIG. 3, and if the examiner determines a measurement position and a measurement value to be proper in step S210, then step S211 and step S212 are executed. If the examiner determines the measurement position and the measurement value to be improper in step S210, then step S602 is executed by an operation on the remeasurement instruction field 326 or the like. A measurement condition is previously determined by the measurement condition setting unit 152 in step S110 by setting of parts and measurement items indicated in the measurement items 322, and the previously determined measurement condition is stored in the storage area 1472 of the recording unit 140. In step S602, the measurement condition is read out from the storage area 1472 of the recording unit 140, and the database is searched on the basis of the measurement condition to create a file of the relevant measurement position candidate regions. In step S604, a selection operation field 472 is displayed together with the ultrasonic image 330 as shown in FIG. 22 on the basis of the creation of the file.

In step S622, the examiner operates the selection operation field 472. For example, if an indication "First" 481 is selected, the first measurement position candidate region in the file created in step S602 is read out in step S624, and the measurement position candidate region read out in step S626 is superimposed and displayed on the ultrasonic image 330. In step S632, the examiner determines whether the displayed measurement position candidate region is proper, and for example, if the examiner operates the selection operation field 472 again, the control unit 170 determines that the region is improper in step S632, and the execution of the control unit 170 proceeds to step S622. If the examiner operates an indication "Next" 483, the next measurement position candidate region in the file created in step S602 is selected. If an indication "Previous" 482 is operated, the previous measurement position candidate region in the file is selected, and if an indication "Last" 484 is operated, the last measurement position candidate region in the file is selected. If an indication "Decide" 485 is operated, the displayed measurement position candidate region is fixed. If an indication "Cancel" 486 is operated, fixing by the indication "decide" 485 can be cancelled. If an indication "List" 487 is operated, a list of titles of measurement position candidate regions constituting the file is displayed.

For example, if the indication "First" 481 is operated, measurement position candidate regions 601 and 602 are displayed in step S626, measurement position candidate regions 501 and 502 are further displayed by execution of the next step S622, and the examiner determines whether any of them is improper, and further performs operation of step S624. When the measurement position candidate regions 401 and 402 are displayed by the operation of step S624, the examiner determines that they are proper, and operates the indication "Decide" 485. Due to the operation of the indication "Decide" 485, the execution of the control unit 170 proceeds from step S632 to step S634, and further executes step S280.

In the execution of step S280, the measurement position candidate regions 401 and 402 determined and set by the operation of the indication "Decide" 485 are stored and held as the auxiliary information 1642 which is the measurement position candidate region in the storage area 1476 of the recording unit 140. According to these measurement position candidate regions 401 and 402, the measurement position computation unit B 114 performs measurement position computation (step S310 of FIG. 3), and the measurement value computation unit 122 computes measurement values (step S150 of FIG. 3).

In this scheme, a measurement position candidate region can be set by merely a simple operation performed by an examiner such as operation of a displayed button. Although the present embodiment has been described about the scheme for setting a cardiac apex portion and an annulus portion which are key tissues of the heart, it may operate as a mechanism for setting a characteristic position of a body tissue, such as for setting a Doppler cursor position for blood flow measurement or setting the position of a tumor.

[Description of an Embodiment which Sets the Position Input 362 Using an M-Mode Image]

Figure 24:
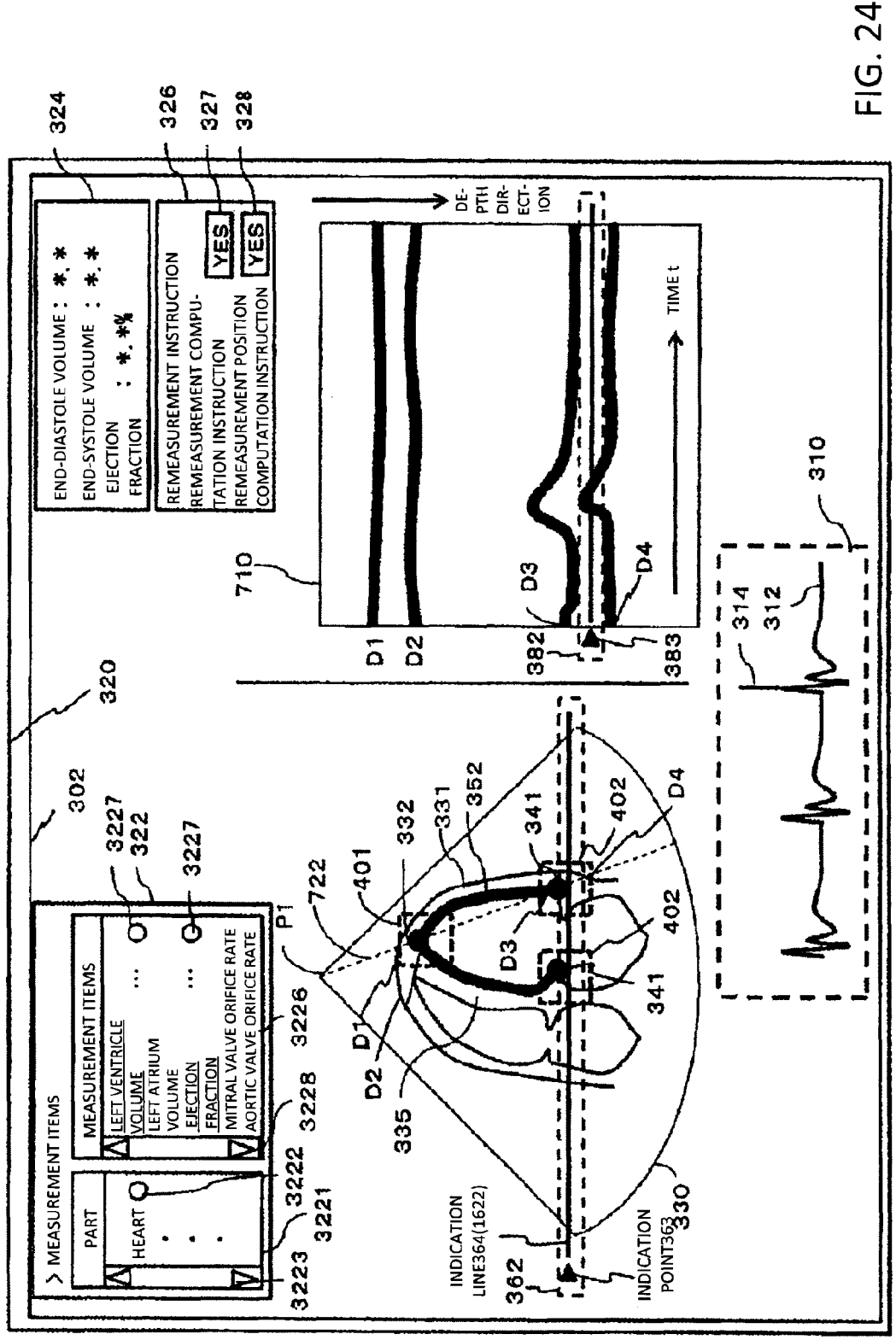
FIG. 24 is an illustrative diagram illustrating a display image in a scheme using an M-mode image, which is still another scheme.
Figure 25:
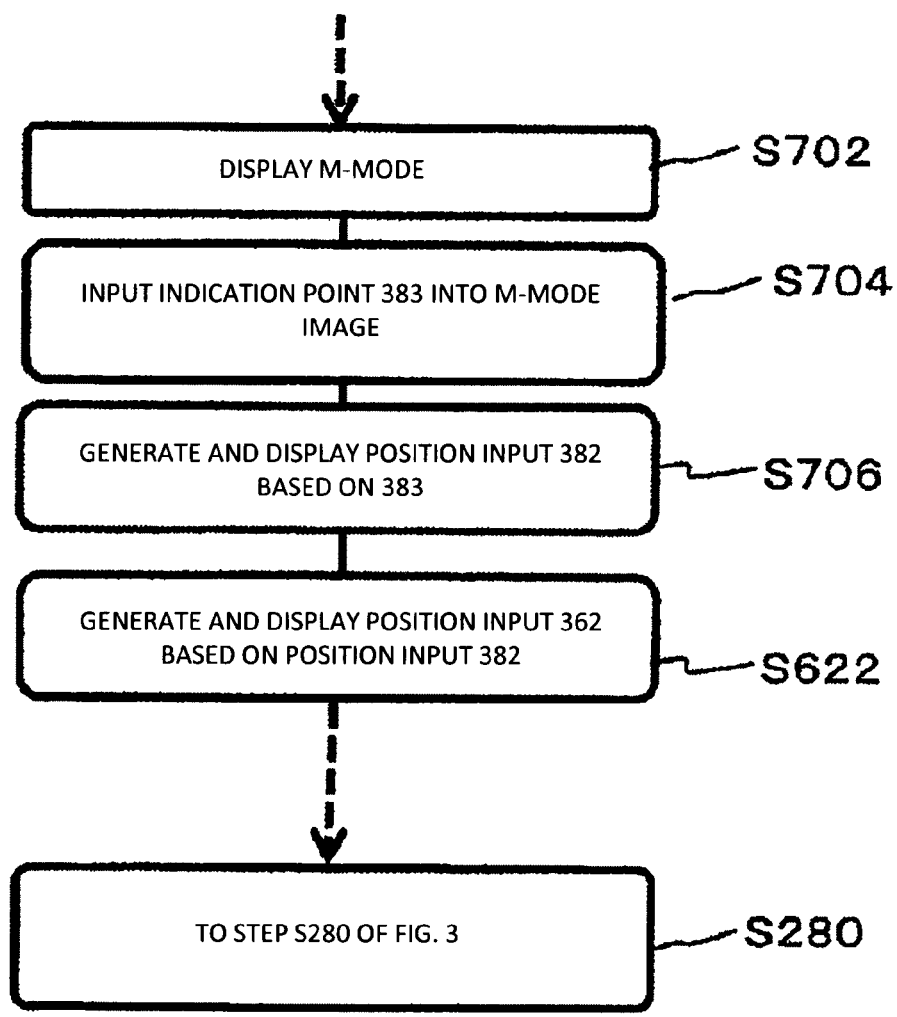
FIG. 25 is a flowchart illustrating the scheme illustrated in FIG. 24.

A method for setting the position input 362 using an M-mode image will be described by reference to FIG. 24 and FIG. 25. In the above-described embodiment, there has been described the method which inputs the position input 362 so as to be superimposed on the ultrasonic image 330, in the image 302 having the ultrasonic image 330 displayed therein. The present embodiment provides a method which inputs the position input 362 using an M (Motion)-mode image 710. FIG. 24 illustrates a display state of the M-mode image 710. The change of brightness over time is shown in the M-mode image 710, in which the brightness in a depth direction along an M-mode line 722 of ultrasonic waves emitted from a point P1 is displayed in a depth direction which is a vertical axis of the M-mode image 710, and an elapsed time t is indicated on a horizontal axis.

In the M-mode image 710, motions of tissues at depth D1, depth D2, depth D3, depth D4 along the M-mode line 722 are displayed along the elapsed time. While the annulus portions 341 are a tissue whose motion is most active, the annulus portions 341 can be easily identified in the M-mode image 710 even if an image of the ultrasonic image 330 is faint or if it is difficult to identify a position because of an active motion of the image. Portions of depth D3 and depth D4 which vary greatly can be determined to be the annulus portions 341.

In step S704, positions of the annulus portions 341 are estimated, and the indication point 383 is inputted and set between depth D3 and depth D4. In step S706, the control unit 170 obtains the position input 382 on the basis of the indication point 383, and superimposes and displays the position input 382 on the M-mode image 710. Further, the control unit 170 executes step S622 to generate the position input 362 by computation on the basis of the indication point 383 or the position input 382 and superimpose and display the position input 362 on the ultrasonic image 330. Incidentally, the ultrasonic image 330 is, for example, a B (Brightness) mode image. Further, step S280 shown in FIG. 3 is subsequently executed, and measurement position candidate regions about the annulus portions 341 and the cardiac apex portion 332 are computed and generated on the basis of the position input 362 or the position input 382. The following operation is performed as previously described.

The indication point 383 which is inputted through the operation unit 108 and superimposed and displayed on the M-mode image 710 represents a distance in the depth direction; that is, a distance from the point P which is a transmitting and receiving position of ultrasonic waves in the ultrasonic image 330. In step S280 of FIG. 25, the auxiliary information generation unit 164 shown in FIG. 1 can set the measurement position candidate regions 402 using depth information indicated by the indication point 383. For example, the auxiliary information generation unit 164 searches the database of the recording unit 140 for areas in which a key tissue is estimated to exist, based on the above-described depth information, and sets the areas as the measurement position candidate regions 402. Since the measurement position candidate regions 402 can be set using information about depth in this way, setting of the measurement position candidate regions 402 can be performed more accurately, and its reliability is improved. Although this embodiment has been described using the annulus portions 341 as a key tissue, the key tissue is not limited thereto. For example, it may be the cardiac apex portion 332 or a vessel. The technical idea of the present embodiment may be applied to measurement of various tissues of various parts; for example, measurement of a tumor.

In the present embodiment, by setting the position input 382 using the M-mode image 710 which displays motion, a tissue with motion such as the annulus portion 341 can be more accurately positioned, and the accuracy of a measurement position candidate region is improved. Although the M-mode image 710 is used as a representative example in the present embodiment, an A-mode image may be used, since the motion of a tissue can also be detected using an A (amplitude) mode.

[Description of an Embodiment which Sets the Position Input 362 Using a Focus Instruction]

Figure 26:
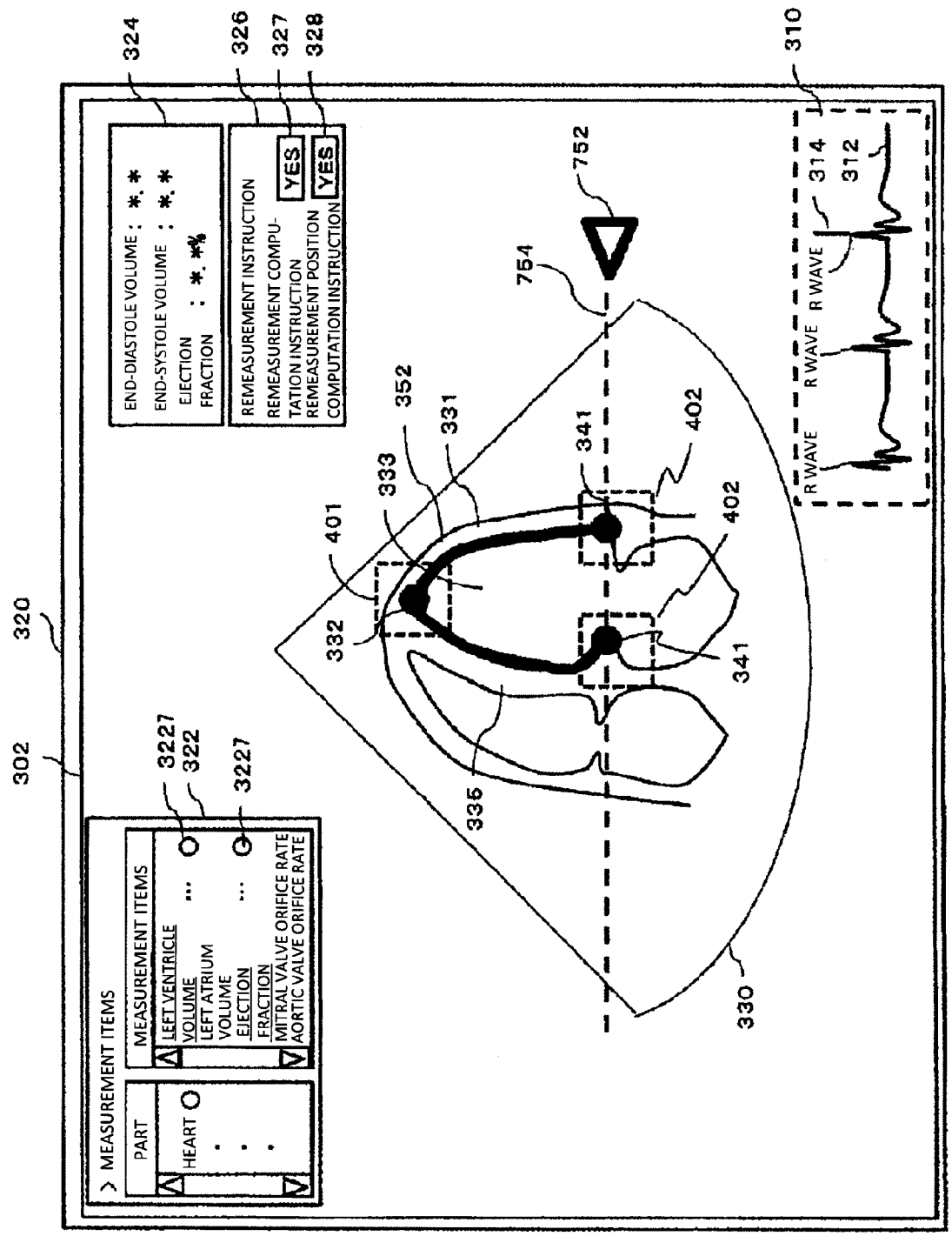
FIG. 26 is an illustrative diagram illustrating a display image in a scheme using a focus position, which is still another scheme.
Figure 27:
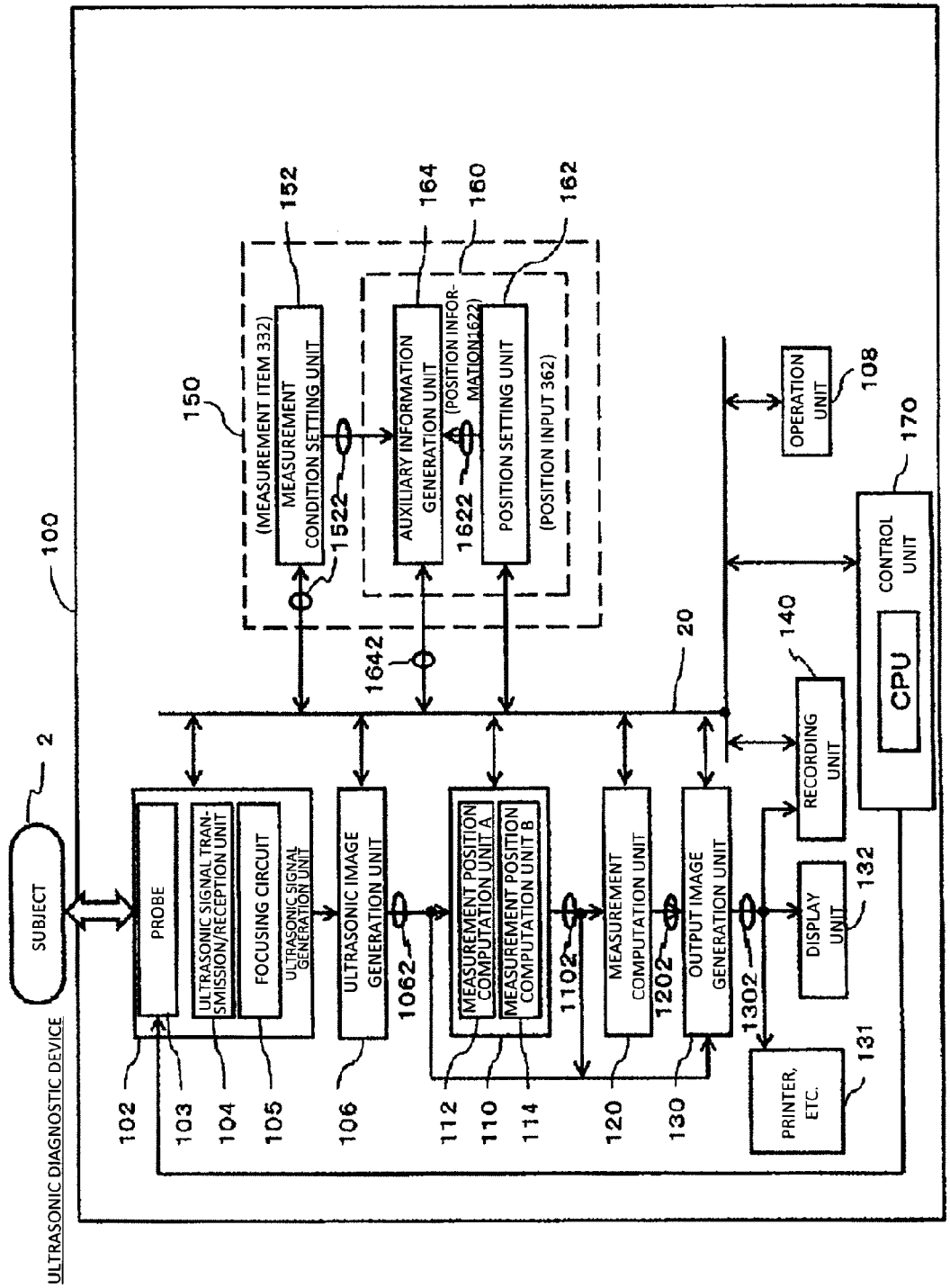
FIG. 27 is a configuration diagram illustrating the scheme illustrated in FIG. 26.
Figure 28:
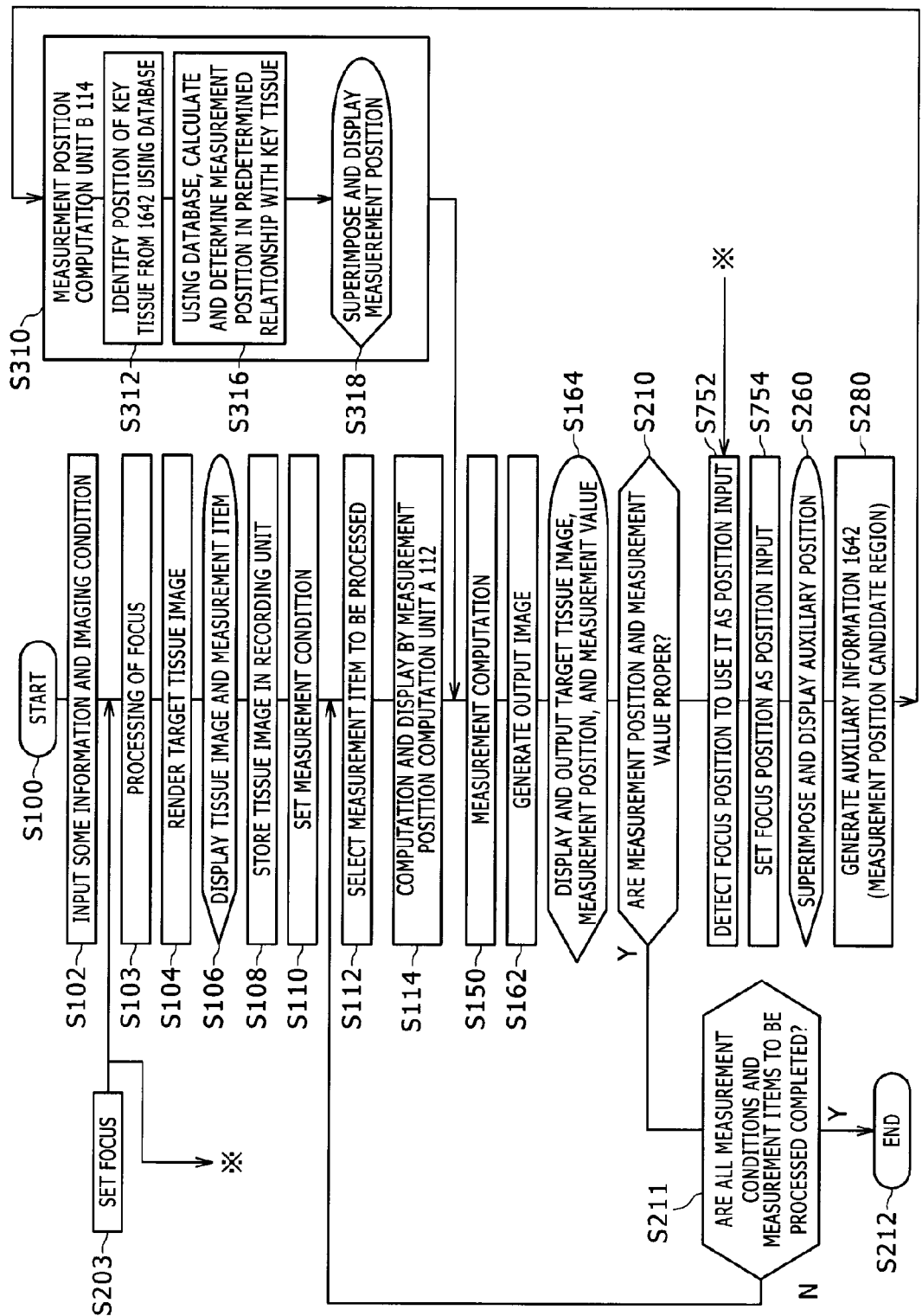
FIG. 28 is a flowchart illustrating the scheme illustrated in FIG. 26.

Next, by reference to FIG. 26, FIG. 27, and FIG. 28, there will be described a scheme which performs instruction for controlling a focus position of an ultrasonic diagnostic device, and sets the position input 362 using a focus position 752. The basic components and operation of FIG. 27 are the same as described above by reference to FIG. 1. Components given the same reference numerals as in FIG. 1 are components having the same functions, and a description thereof will be omitted. Further, the basic operation of FIG. 28 is the same as that of FIG. 3, and steps given the same reference numerals as in FIG. 3 perform the same processes. A description of the steps having the same reference numerals will be omitted.

The examiner performs setting of the focus position 752 for rendering the ultrasonic image 330. An ultrasonic beam converges at a depth in which the focus position is set, so that a high-resolution image can be obtained. By setting the focus position at a depth to which the examiner wants to pay the most attention, the most notable tissue can be rendered more vividly. By setting the focus position 752, a focusing circuit 105 having the ultrasonic signal generation unit 102 of FIG. 27 operates, ultrasonic waves which converge at the focus position 752 are applied, and the tissue image 1062 generated by the ultrasonic image generation unit 106 becomes a more vivid image at the focus position 752.

When the focus position 752 is inputted to set a focus position in step S203 of FIG. 28, focusing processing is performed in step S103, and on the basis of an ultrasonic image subjected to the focusing processing, an ultrasonic image is generated in step S104, and displayed as the ultrasonic image 330. If the focus position 752 is set at the depth of the annulus portions 341, the image quality of a tissue at the depth of the annulus portions 341 is improved.

If the remeasurement instruction field 326 is operated in step S210 because a measurement position or a measurement value is determined to be improper, the focus position 752 set in step S203 is detected in step S752, and the focus position 752 is used instead of the indication point 363 of the position input 362. In step S754, an indication line 754 is displayed on the basis of the focus position 752 in place of the indication point 363, and is set as a position input. In step S260, the indication line 754 is displayed instead of the indication line 364. Next, step S280 is executed. The following operation is performed as described above by reference to FIG. 3.

The examiner can set the focus position 752 in a portion which is a key tissue, thereby improving the quality of an image of the key tissue, and further can set a position input on which a measurement position candidate region is based with respect to the key tissue. Therefore, the operating efficiency is improved. In addition, the complexity of operation can be reduced.

Figure 29:
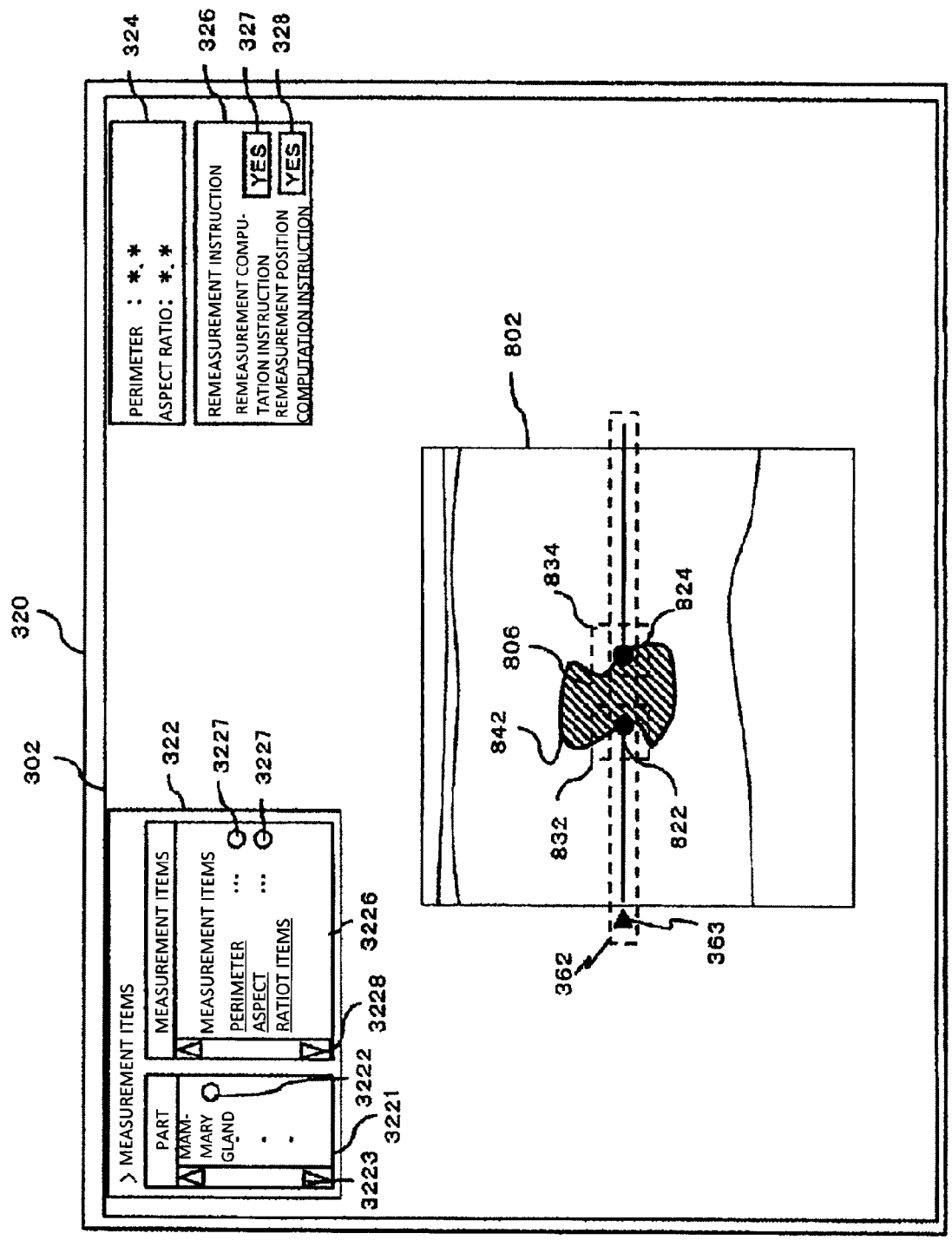
FIG. 29 is an illustrative diagram illustrating a display image in a case where the present invention is applied to measurement of a tumor of a mammary gland.

Although a heart is mainly used as an example of parts in the above description, a great effect can be obtained by applying the present invention to the other parts and tissues. FIG. 29 is an example to which the present invention is applied for measuring a state of a tumor of a mammary gland. The measurement of a tumor of a mammary gland shown in FIG. 29 can be applied to any of the above-described schemes of FIG. 3, FIG. 6 to FIG. 8, FIG. 12, FIG. 14, FIG. 16, FIG. 18, FIG. 19, FIG. 21, FIG. 23, FIG. 25, and FIG. 28, and will be described by reference to FIG. 3 as a representative of these figures.

In step S104 of FIG. 3, input and setting of a measurement condition are performed. A mammary gland is selected from the part display field 3221 shown in FIG. 29, and a perimeter and an aspect ratio are selected from the measurement item display field 3226. After these are determined, the setting marks 3222 and 3227 indicating settings are displayed. Although measurement values are not displayed in the fields of the measurement values 324 at this stage, a perimeter and an aspect ratio are displayed as measurement items. In step S104, an ultrasonic image is generated by the auxiliary information setting unit 160, and displayed as the image 302 on the display screen 320 of the display unit 132. On the display screen 320, a tumor 806 of the mammary gland is displayed as an ultrasonic image 802. In step S110, a measurement condition is captured and set by the measurement condition setting unit 152 by an instruction from the examiner on the basis of measurement items or by data searching using measurement items.

In step S114, a measurement position is computed according to the measurement condition. In FIG. 29, a circumference 842 of the tumor 806 is a measurement position in the measurement item. It is assumed here that portions of edges 822 and 824 of the tumor 806 are faint, and computation result of the measurement position is not proper. The examiner operates the remeasurement instruction field 326 of FIG. 29 or directly inputs the indication point 363, assuming that the measurement position displayed in step S164 and the measurement value computed based on this are improper. On the basis of these operations, the control unit 170 determines that there is an indication of improperness in step S210, and the execution of the control unit 170 proceeds to step S220.

Display of the position input 362 is performed on the basis of the already inputted indication point 363 or the indication point 363 inputted by the examiner in step 220 (step S260). One example of details of the step S220 and step S260 has already been described by reference to the flowcharts of FIG. 7 and FIG. 8. In step S280, measurement position candidate regions 832 and 834 are computed on the basis of the position input 362. Although in the previously described embodiment, there are the annulus portions 341 and the measurement items 322 as key tissues, and the measurement position candidate regions 402 and 401 are computed using them as key tissues, in the case of FIG. 29, the measurement position candidate regions 832 and 834 are computed considering edges 822 and 824, which are boundaries between the tumor and the normal tissue, as key tissues according to an instruction from the examiner.

The computation of the measurement position candidate regions 832 and 834 is performed on the basis of search results of the measurement condition database 1500 described in FIG. 30. In this embodiment, search is performed first on the basis of the mammary gland displayed in the part display field 3221 shown in FIG. 29 and the perimeter display in the measurement item display field 3226 to output a contour line described in FIG. 30 as the measurement position. In this case, unlike the case of the previously described left ventricle volume, a special key tissue is not outputted. However, since the examiner determines that there is improperness in step S210, and there should be a cause for it, it is assumed that there is an improper portion in the measurement position as the cause. This improper portion is treated as a key tissue, and the auxiliary information generation unit 164 performs computation to calculate the auxiliary information 1642 in step S280 assuming that a position indicated by the indication point 363 inputted by the examiner indicates the vicinity of the key tissue which is the improper measurement position.

In step S280, the measurement position candidate regions 832 and 834 are computed and sent as the auxiliary information 1642 to the measurement position computation unit B 114, and in step S310, the measurement position is computed again by the measurement position computation unit B 114. In the measurement position computation unit B 114, for determining the whole measurement position, computation is performed especially using the measurement position candidate regions 832 and 834, and respective measurement positions are used. When the circumference 842 of the tumor 806 is to be determined as a measurement position, the whole measurement position is determined so as to pass through the edges 822 and 824 which are measurement positions computed using the above-described measurement position candidate regions 832 and 834, respectively. In this way, within the whole measurement position, measurement positions supposed to have a particular problem are specifically processed using the measurement position candidate regions 832 and 834 determined for them, so that the whole measurement position can be determined more accurately, and a more accurate measurement value can be obtained.

According to the present invention, the auxiliary information 1642 such as a measurement position candidate region is set, so that a more accurate measurement position can be determined, and the accuracy of measurement is improved. In the present invention, a measurement position candidate point which is a narrowed measurement position candidate region may be inputted by an examiner and used as a measurement position, but in this case, the burden on the examiner may increase, and it is conceivable that the examiner cannot directly specify the accurate measurement position. As described above, only by the examiner inputting the position input 362 near the measurement position, the control unit 170 computes a measurement position candidate region on the basis of the position input 362, so that the burden on the examiner can be reduced. Further, instead of the examiner, the ultrasonic diagnostic device 100 sets a measurement position candidate region based on a database, and the ultrasonic diagnostic device 100 further computes a measurement position in the measurement position candidate region based on the database, and accordingly, in many cases, a more accurate measurement position than that inputted by the examiner can be set. As described above, according to the present invention, the accuracy of measurement can be improved. There is a larger effect for a subject in a state different from the normal state. Further, in the above-described embodiments, it is obvious that the burden on an examiner can be reduced, and moreover operability of imaging by the ultrasonic diagnostic device 100 is also improved. Various effects in the embodiments have been described above.

REFERENCE SIGNS LIST

2: Subject, 20: Connection line, 100: Ultrasonic diagnostic device, 102: Ultrasonic signal generation unit, 103:

Probe, 104: Ultrasonic image generation unit, 105: Focusing circuit, 106: Ultrasonic image generation unit, 108: Operation unit, 110: Measurement position computation unit, 112: Measurement position computation unit A, 114: Measurement position computation unit B, 120: Measurement computation unit, 122: Measurement value computation unit, 130: Output image generation unit, 132: Display unit, 140: Recording unit, 150: Measurement setting unit, 152: Measurement condition setting unit, 160: Auxiliary information setting unit, 162: Position setting unit, 164: Auxiliary information generation unit, 170: Control unit, 141: Image information database, 310: Electrocardiogram, 312: Electrocardiographic waveform, 314: Time phase marker, 322: Measurement items, 324: Measurement values, 326: Remeasurement instruction field, 331: Heart, 332: Cardiac apex portion, 333: Left ventricle, 336: Right atrium, 338: Left atrium, 341: Annulus portion, 362: Position input, 363: Indication point, 364: Indication line, 366: Rotation mark, 372: Position input, 373: Indication point, 374: Indication line, 382: Position input, 383: Indication point, 401: Measurement position candidate region, 402: Measurement position candidate region, 410: Position input, 450: Position input, 472: Selection operation field, 710: M-mode image, 722: M-mode line, 752: Focus position, 754: Indication line, 806: Tumor, 822: Edge, 824: Edge, 832: Measurement position candidate region, 834: Measurement position candidate region.

The invention claimed is:

1. A medical diagnosis device, comprising:
    an image generator that is configured to generate an image of a subject;
    an auxiliary information generator that is configured to generate auxiliary information on the basis of a position input;
    a measurement computator that is configured to compute a measurement position using the image of the subject generated by the image generator, the auxiliary information, and a measurement condition, and to compute a measurement value using the image of the subject and the computed measurement position; and
    a display unit that displays the image of the subject generated by the image generator, and the measurement value computed by the measurement computator,
    wherein the auxiliary information gives a refinement condition for identifying the measurement position by computation;
    wherein the measurement computator comprises:
        a first measurement position computator that is configured to compute the measurement position using the image of the subject and the measurement condition; and
        a second measurement position computator that is configured to compute the measurement position using the image of the subject, the measurement condition, and the auxiliary information, and
    wherein the measurement value is computed using the measurement position computed by the first measurement position computator or the second measurement position computator.

2. The medical diagnosis device according to claim 1, comprising:
    a probe that applies an ultrasonic wave to the subject and receives the ultrasonic wave from the subject,
    wherein the image generator is configured to generate an ultrasonic image on the basis of the ultrasonic wave received by the probe, and
    the measurement computator is configured to compute the measurement position using the ultrasonic image generated by the image generator, the measurement condition, and the auxiliary information, and to compute the measurement value using the computed measurement position and the ultrasonic image generated by the image generator.

3. The medical diagnosis device according to claim 1, wherein
    ahead of the second measurement position computator, the first measurement position computator computes a first measurement position as the measurement position using the image of the subject and the measurement condition,
    the measurement computator computes a first measurement value as the measurement value using the first measurement position, and the computed first measurement value is displayed on the display unit,
    the auxiliary information is generated by the auxiliary information generator on the basis of the position input that is further inputted,
    the second measurement position computator computes a second measurement position as the measurement position using the auxiliary information, the image of the subject, and the measurement condition, and
    the measurement computator computes a second measurement value using the second measurement position, and the computed second measurement value is displayed on the display unit.

4. The medical diagnosis device according to claim 1, further comprising:
    a measurement condition settor that is configured to set the measurement condition; and
    an operation interface,
    wherein, ahead of the second measurement position computator, the first measurement position computator computes a first measurement position as the measurement position using the image of the subject generated by the image generator and the measurement condition set by the measurement condition setting unit,
    the measurement computator computes a first measurement value as the measurement value using the first measurement position,
    the first measurement position, and the first measurement value computed using the first measurement position by the measurement computator are displayed on the display unit,
    the auxiliary information is generated by the auxiliary information generator when the position input is further inputted through the operation interface,
    the second measurement position computator computes a second measurement position as the measurement position using the auxiliary information, the image of the subject, and the measurement condition settor,
    the measurement computator computes a second measurement value as the measurement value using the second measurement position, and
    the second measurement position, and the measurement value computed using the second measurement position by the measurement computator are displayed on the display unit.

5. The medical diagnosis device according to claim 1, comprising
    a position settor that is configured to generate an indication line on the basis of an indication point which is inputted with respect to an image where the image of the subject is displayed, wherein the auxiliary information generator generates the auxiliary information based on information of the indication line.

6. The medical diagnosis device according to claim 5, comprising
a unit for changing an angle of the indication line on the basis of an input operation which rotates the indication line generated by the position settor.

7. A medical diagnosis device, comprising:
an image generator that is configured to generate an image of a subject;
an auxiliary information generator that is configured to generate auxiliary information on the basis of a position input;
a measurement computator that is configured to compute a measurement position using the image of the subject generated by the image generator, the auxiliary information, and a measurement condition, and to compute a measurement value using the image of the subject and the computed measurement position; and
a display unit that displays the image of the subject generated by the image generator, and the measurement value computed by the measurement computator,
wherein the auxiliary information gives a refinement condition for identifying the measurement position by computation,
wherein the medical diagnosis device further comprises:
a measurement condition settor for setting the measurement condition; and
an operation interface for performing the position input, and
wherein, when a plurality of position inputs are inputted from the operation interface,
the auxiliary information generator generates a plurality of measurement position candidate regions as the auxiliary information, corresponding to the plurality of position inputs, and
the measurement computator computes a plurality of key positions corresponding respectively to the plurality of measurement position candidate regions, and further computes the measurement position using a plurality of key positions, and computes the measurement value using the measurement position.

8. A medical diagnosis device, comprising:
an image generator that is configured to generate an image of a subject;
an auxiliary information generator that is configured to generate auxiliary information on the basis of a position input;
a measurement computator that is configured to compute a measurement position using the image of the subject generated by the image generator, the auxiliary information, and a measurement condition, and to compute a measurement value using the image of the subject and the computed measurement position; and
a display unit that displays the image of the subject generated by the image generator, and the measurement value computed by the measurement computator,
wherein the auxiliary information gives a refinement condition for identifying the measurement position by computation,
wherein the medical diagnosis device further comprises:
a measurement condition settor for setting the measurement condition; and
an operation interface for performing the position input,
wherein, when one position input is inputted from the operation interface, the auxiliary information generator generates a plurality of measurement position candidate regions as the auxiliary information, with respect to the one position input, and
the measurement computator computes a plurality of key positions corresponding respectively to the plurality of measurement position candidate regions, and further computes the measurement position using the plurality of key positions, and computes the measurement value using the measurement position.

9. A medical diagnosis device, comprising:
an image generator that is configured to generate an image of a subject;
an auxiliary information generator that is configured to generate auxiliary information on the basis of a position input;
a measurement computator that is configured to compute a measurement position using the image of the subject generated by the image generator, the auxiliary information, and a measurement condition, and to compute a measurement value using the image of the subject and the computed measurement position; and
a display unit that displays the image of the subject generated by the image generator, and the measurement value computed by the measurement computator,
wherein the auxiliary information gives a refinement condition for identifying the measurement position by computation,
wherein the medical diagnosis device further comprises:
a measurement condition settor for setting the measurement condition; and
an operation interface for performing the position input,
wherein, when the position input which indicates a center portion of a part is inputted from the operation interface, the auxiliary information generator generates a region in which a key tissue about the measurement condition exists as a measurement position candidate region, on the basis of data of a positional relationship between the key tissue and the center portion of the part, using the position input which indicates the center portion of the part, and sets the generated measurement position candidate region as the auxiliary information, and
the measurement computator computes the measurement position using the measurement position candidate region.

10. A medical diagnosis device, comprising:
an image generator that is configured to generate an image of a subject;
an auxiliary information generator that is configured to generate auxiliary information on the basis of a position input;
a measurement computator that is configured to compute a measurement position using the image of the subject generated by the image generator, the auxiliary information, and a measurement condition, and to compute a measurement value using the image of the subject and the computed measurement position; and
a display unit that displays the image of the subject generated by the image generator, and the measurement value computed by the measurement computator,
wherein the auxiliary information gives a refinement condition for identifying the measurement position by computation, wherein the medical diagnosis device further comprises:
an operation interface for performing the position input; and
a database that indicates a relationship between a center portion of a part and a plurality of key tissues of the part,
wherein, when the position input which indicates the center portion of the part is inputted from the operation interface, measurement position candidate regions are generated respectively in directions in which the plurality of key tissues exist with respect to the position input on the basis of the database, and are set as the auxiliary information, and
the measurement computator computes the measurement position using the measurement position candidate regions.

11. The medical diagnosis device according to claim 1, wherein
an ultrasonic image of a heart is displayed as the image of the subject,
the position input is set so as to be superimposed on the ultrasonic image of the heart,
a measurement position candidate region is set in the horizontal direction and/or depth direction with respect to the position input, as the auxiliary information,
the measurement computator computes the measurement position using the measurement position candidate region.

12. A medical diagnosis device, comprising:
an image generator that is configured to generate an image of a subject;
an auxiliary information generator that is configured to generate auxiliary information on the basis of a position input;
a measurement computator that is configured to compute a measurement position using the image of the subject generated by the image generator, the auxiliary information, and a measurement condition, and to compute a measurement value using the image of the subject and the computed measurement position; and
a display unit that displays the image of the subject generated by the image generator, and the measurement value computed by the measurement computator,
wherein the auxiliary information gives a refinement condition for identifying the measurement position by computation,
a pattern is inputted so as to be superimposed on the image of the subject such that the pattern includes a key tissue based on the measurement condition,
the auxiliary information generator sets as the auxiliary information an area defined by the pattern which includes the key tissue, and
the measurement position computator computes a measurement position of the key tissue in the area defined by the pattern, and further computes the measurement position based on the measurement condition using the measurement position of the key tissue.

13. A medical diagnosis device, comprising:
an image generator that is configured to generate an image of a subject;
an auxiliary information generator that is configured to generate auxiliary information on the basis of a position input;
a measurement computator that is configured to compute a measurement position using the image of the subject generated by the image generator, the auxiliary information, and a measurement condition, and to compute a measurement value using the image of the subject and the computed measurement position; and
a display unit that displays the image of the subject generated by the image generator, and the measurement value computed by the measurement computator,
wherein the auxiliary information gives a refinement condition for identifying the measurement position by computation,
wherein the medical diagnosis device further comprises a database that indicates a relationship between the measurement condition and a measurement position candidate,
wherein the image of the subject is displayed,
the measurement position candidate is retrieved from the database according to an input operation on the basis of the measurement condition, and is displayed so as to be superimposed on the image of the subject, and
the measurement position candidate which is appropriate according to the input operation is set as the auxiliary information.

* * * * *